(12) United States Patent
Meador et al.

(10) Patent No.: US 8,258,251 B2
(45) Date of Patent: *Sep. 4, 2012

(54) HIGHLY POROUS CERAMIC OXIDE AEROGELS HAVING IMPROVED FLEXIBILITY

(75) Inventors: Mary Ann B. Meador, Strongsville, OH (US); Baochau N. Nguyen, North Royalton, OH (US); Haiquan Guo, Avon, OH (US)

(73) Assignees: The United States of America, as represented by the Administrator of the National Aeronautics and Space Administration, Washington, DC (US); Ohio Aerospace Institute, Brook Park, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/776,088

(22) Filed: May 7, 2010

(65) Prior Publication Data

US 2010/0292428 A1 Nov. 18, 2010

Related U.S. Application Data

(63) Continuation-in-part of application No. 11/948,315, filed on Nov. 30, 2007.

(51) Int. Cl.
*C08G 77/26* (2006.01)
*C08G 77/14* (2006.01)
*C08G 77/28* (2006.01)
*C07F 7/02* (2006.01)

(52) U.S. Cl. ............... 528/28; 528/10; 528/30; 528/38; 423/335

(58) Field of Classification Search ............... 528/10, 528/28, 30, 38; 423/335
See application file for complete search history.

(56) References Cited

U.S. PATENT DOCUMENTS

| | | | |
|---|---|---|---|
| 4,374,237 A * | 2/1983 | Berger et al. | 528/28 |
| 5,266,207 A | 11/1993 | Boye et al. | |
| 5,282,955 A | 2/1994 | Leventis et al. | |
| 5,321,102 A | 6/1994 | Loy et al. | |
| 5,457,564 A | 10/1995 | Leventis et al. | |
| 5,502,082 A | 3/1996 | Unger et al. | |
| 5,541,234 A | 7/1996 | Unger et al. | |
| 5,605,983 A | 2/1997 | Dauth et al. | |
| 5,691,054 A | 11/1997 | Tennent et al. | |
| 5,710,187 A | 1/1998 | Steckle, Jr. et al. | |
| 5,818,636 A | 10/1998 | Leventis et al. | |
| 5,846,658 A | 12/1998 | Tennent et al. | |

(Continued)

FOREIGN PATENT DOCUMENTS
WO WO 2005079427 A2 * 9/2005

OTHER PUBLICATIONS

Ilhan et al. "Hydrophobic monolithic aerogels by nanocasting polystyrene on amine-modified silica" J. Mater. Chem. 2006, 16, 3046-3054.*

(Continued)

*Primary Examiner* — Robert S Loewe
(74) *Attorney, Agent, or Firm* — Pearne & Gordon LLP

(57) ABSTRACT

Ceramic oxide aerogels having improved flexibility are disclosed. Preferred embodiments exhibit high modulus and other strength properties despite their improved flexibility. The gels may be polymer cross-linked via organic polymer chains to further improve strength properties, without substantially detracting from the improved flexibility. Methods of making such aerogels are also disclosed.

51 Claims, 36 Drawing Sheets

U.S. PATENT DOCUMENTS

| | | | |
|---|---|---|---|
| 5,872,070 A | 2/1999 | Dismukes et al. | |
| 5,990,184 A | 11/1999 | Biesmans et al. | |
| 6,080,816 A * | 6/2000 | Gregorovich et al. | 525/100 |
| 6,156,812 A | 12/2000 | Lau et al. | |
| 6,284,908 B1 | 9/2001 | Loy et al. | |
| 6,300,385 B1 | 10/2001 | Hashida et al. | |
| 6,364,953 B1 | 4/2002 | Kawakami et al. | |
| 6,423,811 B1 | 7/2002 | Lau et al. | |
| 6,428,898 B1 | 8/2002 | Barsotti et al. | |
| 6,686,035 B2 * | 2/2004 | Jiang et al. | 428/304.4 |
| 7,470,636 B2 * | 12/2008 | Ko et al. | 438/790 |
| 2002/0167118 A1 | 11/2002 | Billiet et al. | |
| 2003/0106487 A1 | 6/2003 | Huang | |
| 2004/0005340 A1 * | 1/2004 | Patel et al. | 424/401 |
| 2004/0047988 A1 * | 3/2004 | Lee et al. | 427/240 |
| 2004/0132846 A1 * | 7/2004 | Leventis et al. | 521/99 |
| 2004/0144726 A1 | 7/2004 | Chmelka et al. | |
| 2004/0216641 A1 * | 11/2004 | Hamada et al. | 106/287.16 |
| 2005/0192366 A1 | 9/2005 | Ou et al. | |
| 2005/0192367 A1 * | 9/2005 | Ou et al. | 521/64 |
| 2005/0230298 A1 * | 10/2005 | Jiang et al. | 210/198.2 |
| 2006/0004121 A1 * | 1/2006 | Ding et al. | 523/115 |
| 2006/0216219 A1 | 9/2006 | DeFriend et al. | |
| 2007/0203341 A1 | 8/2007 | Shea et al. | |
| 2007/0215547 A1 * | 9/2007 | O'Gara | 210/656 |
| 2008/0081120 A1 * | 4/2008 | Van Ooij et al. | 427/387 |
| 2009/0025609 A1 * | 1/2009 | Egami et al. | 106/287.12 |
| 2009/0036646 A1 | 2/2009 | Lu et al. | |
| 2009/0206034 A1 | 8/2009 | Nakajima | |
| 2010/0003181 A1 * | 1/2010 | Egami et al. | 423/335 |

OTHER PUBLICATIONS

Wahab et al. "Periodic Mesoporous Organosilica Materials Incorporating Various Organic Functional Groups: Synthesis, Structural Characterization, and Morphology" Chem. Mater. 2005, 17, 2165-2174.*

Wahab et al. "Bridged amine-functionalized mesoporous organosilica materials from 1,2-bis(triethoxysilyl)ethane and bis[(3-trimethoxysilyl)propyl]amine" Journal of Solid State Chemistry, 2004, 177, 3439-3447.*

Moner-Girona, M. et al., "Mechanical Properties of Silica Aerogels Measured by Microindentation: Influence of Sol-Gel Processing Parameters and Carbon Addition," Journal of Non-Crystalline Solids, vol. 285, pp. 244-250, 2001.

Moner-Girona, M. et al., "Sol-Gel Route to Direct Formation of Silica Aerogel Microparticles Using Supercritical Solvents," J. Sol-Gel Sci. Technol., vol. 26, pp. 645-649, 2003.

Morris, C.A. et al., "Silica Sol as a Nanoglue: Flexible Synthesis of Composite Aerogels," Science, vol. 284, pp. 622-624, Apr. 23, 1999.

Mulik, S. et al., "Cross-Linking 3D Assemblies of Nanoparticles into Mechanically Strong Aerogels by Surface-Initiated Free-Radical Polymerization," Chem. Mater., vol. 20, pp. 5035-5046, 2008.

Mulik, S. et al., "Macroporous Electrically Conducting Carbon Networks by Pyrolysis of Isocyanate-Cross-Linked Resorcinol-Formaldehyde Aerogels," Chem. Mater., vol. 20, pp. 6985-6997, 2008.

Novak, B.M. et al., "Low-Density, Mutually Interpenetrating Organic-Inorganic Composite Materials via Supercritical Drying Techniques," Chem. Mater., vol. 6, pp. 282-286, 1994.

Nguyen, B.N. et al., "Tailoring Elastic Properties of Silica Aerogels Cross-Linked with Polystyrene," Applied Materials & Interfaces, vol. 1, No. 3, pp. 621-630, 2009.

Orndoff, E. et al., "Thermal Insulation Performance of Textile Structures for Spacesuit Application at Martian Pressure and Temperature," NASA Document No. 20000040789, 13 pages, 2000.

Pajonik, G.M., "Some Catalytic Applications of Aerogels for Environmental Purposes," Catalysis Today, 52, (1999), pp. 3-13.

Parmenter, K.E. et al., "Mechanical Properties of Silica Aerogels," Journal of Non-Crystalline Solids, vol. 223, pp. 179-189, 1998.

Paul, H.L. et al., "Comparison of Thermal Insulation Performance of Fibrous Materials for the Advanced Space Suit," J. Biomechanical Engineering, vol. 125, pp. 639-647, Oct. 2003.

Pekala, R.W. et al., "A Comparison of Mechanical Properties and Scaling Law Relationships for Silica Aerogels and Their Organic Counterparts," Mater. Res. Soc. Symp. Proc., vol. 207, pp. 197-200, 1991.

Phalippou, J. et al., "Fracture Toughness of Silica Aerogels," Revue de Physique Appliquee, Colloque C4, Supplement au No. 4, Tome 24, pp. C4-191-C4-196, Apr. 1989.

Phalippou, J. et al., "Glasses from Aerogels-Part 1. The Synthesis of Monolithic Silica Aerogels," Journal of Materials Sciences, vol. 25, No. 7, pp. 3111-3117, 1990.

Pierre, A.C. et al., "Chemistry of Aerogels and Their Applications," Chem. Rev., vol. 102, pp. 4243-4265, 2002.

Posselt, D. et al., "The Thermal Conductivity of Silica Aerogels in the Phonon, the Fracton and the Particle-Mode Regime," Europhysics Letters, vol. 16, No. 1, pp. 59-65, Sep. 1, 1991.

Rao, A.V. et al., "Synthesis of Flexible Silica Aerogels Using Methyltrimethoxysilane (MTMS) Precursor," Journal of Colloid and Interface Science, vol. 300, pp. 279-285, 2006.

Reza, S. et al., "Aerocapture Inflatable Decelerator (AID) for Planetary Entry," Paper No. AIAA 2007-2516, 19th AIAA Aerodynamic Decelerator Systems Technology Conference and Seminar, May 21-24, 2007, Williamsburg, VA.

Rogacki, G. et al., "Diffusion of Ethanol-Liquid CO2 in Silica Aerogel," Journal of Non-Crystalline Solids, vol. 186, pp. 73-77, 1995.

Schaefer, D.W. et al., "Structure and Topology of Silica Aerogels," Journal of Non-Crystalline Solids, vol. 145, pp. 105-112, 1992.

Schaefer, D.W. et al., "Structure of Arylene-Bridged Polysilsesquioxane Xerogels and Aerogels," Chem. Mater. vol. 16, pp. 1402-1410, 2004.

Shea, K.J. et al., "Aryl-Bridged Polysilsesquioxanes-New Microporous Materials," Chemistry of Materials, vol. 1, pp. 572-574, 1989.

Shea, K.J. et al., "A Mechanistic Investigation of Gelation. The Sol-Gel Polymerization of Precursors to Bridged Polysilsesquioxanes," Acc. Chem. Res., vol. 34, pp. 707-716, 2001.

Shea, K.J. et al., "Bridged Polysilsesquioxanes. Molecular-Engineered Hybrid Organic-Inorganic Materials," Chem. Mater., vol. 13, pp. 3306-3319, American Chemical Society, 2001.

Sleator, T. et al., "Low-Temperature Specific Heat and Thermal Conductivity of Silica Aerogels," Physical Review Letters, vol. 66, No. 8, pp. 1070-1073, Feb. 25, 1991.

Tao, Y. et al., "Conductive and Mesoporous Single-Wall Carbon Nanohorn/Organic Aerogel Composites," Langmuir, vol. 23, pp. 9155-9157, 2007.

Tsou, P., "Silica Aerogel Captures Cosmic Dust Intact," Journal of Non-Crystalline Solids, vol. 186, pp. 415-427, 1996.

Tullo, A.H., "Stiff Competition-Long Fiber Reinforced Thermoplastics Are Gathering Strength in Key Industries," Chem. & Eng. News, pp. 21-22, Jan. 28, 2002.

Vivod, S.L. et al., "Di-Isocyanate Cross-Linked Silica Aerogels with Hexyl Links Incorporated into the Underlying Silica Backbone," Polymer Preprints, vol. 50, No. 1, pp. 119-120, 2009.

Woigner, T. et al., "Mechanical Strength of Silica Aerogels," Journal of Non-Crystalline Solids, vol. 100, pp. 404-408, 1988.

Woigner, T. et al., "Scaling Law Variation of the Mechanical Properties of Silica Aerogels," Revue de Physique Appliquee, Colloque C4, Supplement au No. 4, Tome 24, pp. C4-179-C4-194, Apr. 1989.

Woigner, T. et al., "Glasses from Aerogels. Part 2-The Aerogel-Glass Transformation," Journal of Materials Sciences, pp. 3118-3126, 1990.

Woigner, T. et al., "Different Kinds of Fractal Structures in Silica Aerogels," Journal of Non-Crystalline Solids, vol. 121, pp. 198-201, 1990.

Woigner, T. et al., "Section 13. Rheological, Mechanical and Other Properties—Evolution of Mechanical Properties during the Alcogel-Aerogel-Glass Process," Journal of Non-Crystalline Solids, vol. 147 & 148, pp. 672-680, 1992.

Woigner, T. et al., "Different Kinds of Structure in Aerogels: Relationships with the Mechanical Properties," Journal of Non-Crystalline Solids, vol. 241, pp. 45-52, 1998.

Yim, T.J. et al., "Fabrication and Thermophysical Characterization of Nano-Porous Silica-Polyurethane Hybrid Aerogel by Sol-Gel Processing and Supercritical Solvent Drying Technique," Koren J. Chem. Eng., 19(1), (2002), pp. 159-166.

Zhang, G. et al., "Isocyanate-Crosslinked Silica Aerogel Monoliths: Preparation and Characterization," Journal of Non-Crystalline Solids, Vol. 350, pp. 152-164, 2004.

Prosecution history for U.S. Appl. No. 10/643,578, retrieved on Jun. 17, 2009.

Prosecution history for U.S. Appl. No. 11/266,025, retrieved on Jun. 17, 2009.

International Search Report and Written Opinion dated Jun. 1, 2009 from corresponding PCT Application No. PCT/US08180611 (Publication No. WO 2009/073287).

Armand, A.G. et al., "Caracterisation Acoustique et Mecanique des Aerogels de Silice [Acoustic and Mechanical Characterization of Silica Aerogels]," Journal de Physique IV, Colloque C1, supplement au Journal de Physique III, vol. 2, pp. C1-759-C1-762, Apr. 1992.

Barton, T.J. et al., "Tailored Porous Materials," Chem. Mater., vol. 11, pp. 2633-2656, 1999.

Boday, D.J. et al., "Strong, Low-Density Nanocomposites by Chemical Vapor Deposition and Polymerization of Cyanoacrylates on Aminated Silica Aerogels," Applied Materials & Interfaces, vol. 1, No. 7, pp. 1364-1369, 2009.

Braun, R.D. et al., "Mars Exploration Entry, Descent, and Landing Challenges," Journal of Spacecraft and Rockets, vol. 44, No. 2, pp. 310-323, Mar./Apr. 2007.

Brown, G.J. et al., "Inflatable Aerocapture Decelerators for Mars Orbiters," Paper No. AIAA 2007-2543, 19th AIAA Aerodynamic Decelerator Systems Technology Conference and Seminar, May 21-24, 2007, Williamsburg, VA.

Bruesch, P. et al, "Electrical and Infrared Dielectrical Properties of Silica Aerogels and of Silica-Aerogel-Based Composites," Applied Physics A—Solids and Surfaces, vol. 57, pp. 329-337, 1993.

Burchell, M.J. et al., "Capture of Hypervelocity Particles in Aerogel: In Ground Laboratory and Low Earth Orbit," Planetary and Space Science, vol. 47, pp. 189-204, 1999.

Buttner, D. et al., "Thermal Loss Coefficients of Low-Density Silica Aerogel Tiles," Solar Energy, vol. 40, No. 1, pp. 13-15, 1988.

Capadona, L.A. et al., "Flexible, Low-Density Polymer Crosslinked Silica Aerogels," Polymer, vol. 47, pp. 5754-5761, 2006.

Caps, R. et al., "Thermal Transport in Monolithic Silica Aerogel," Revue de Physique Appliquee, Colloque C4, Supplement au No. 4, Tome 24, pp. C4-113-C4-118, Apr. 1989.

Courtens, E. et al., "Structure and Dynamics of Silica Aerogels," Philosophical Magazine B, vol. 65, No. 2, pp. 347-355, 1992.

Cross, J. et al., "Mechanical Properties of SiO2-Aerogels," Revue de Physique Appliquee, Colloque C4, Supplement au No. 4, Tome 24, pp. C4-185-C4-190, Apr. 1989.

Da Silva, A. et al., "Properties of Water Absorbed in Porous Silica Aerogels," Journal of Non-Crystalline Solids, vol. 145, pp. 168-174, 1992.

Damrau, U. et al., "Si MAS-NMR Investigations of Silica Aerogels," Journal of Non-Crystalline Solids, vol. 145, pp. 164-167, 1992.

Devreux, F. et al., "NMR Determination of the Fractal Dimension in Silica Aerogels," Physical Review Letters, vol. 65, No. 5, pp. 614-617, Jul. 30, 1990.

Ehrburger-Dolle, F. et al., "Relations Between the Texture of Silica Aerogels and Their Preparation," Journal of Non-Crystalline Solids, Vol. 186, pp. 9-17, 1995.

Emmerling, A. et al., "Structural Modifications of Highly Porous Silica Aerogels upon Densification," J. Appl. Cryst., vol. 24, pp. 781-787, 1991.

Emmerling, A. et al., "Relationship Between Optical Transparency and Nanostructural Features of Silica Aerogels," Journal of Non-Crystalline Solids, Vol. 185, pp. 240-248, 1995.

Fesmire, J.E., "Aerogel Insulation Systems for Space Launch Applications," Cryogenics, vol. 46, pp. 111-117, 2006.

Gomez Alvarez-Arenas, T.E. et al., "Viscoelasticity of Silica Aerogels at Ultrasonic Frequencies," Applied Physics Letters, vol. 81, No. 7, pp. 1198-1200, Aug. 12, 2002.

Gross, J. et al., "Mechanical Properties of SiO2 Aerogels," J. Phys. D: Appl. Phys., vol. 21, pp. 1447-1451, 1988.

Gross, J. et al., "Ultrasonic Velocity Measurements in Silica, Carbon and Organic Aerogels," Journal of Non-Crystalline Solids, vol. 145, pp. 217-222, 1992.

Gross, J. et al., "Ultrasonic Evaluation of Elastic Properties of Silica Aerogels," Materials Science and Engineering, vol. A168, pp. 235-238, 1993.

Guo, H. et al., "Elastic Low Density Aerogels Derived from Bis[3-(triethoxysilyl)propyl]disulfide, Tetramethylorthosilicate and Vinyltrimethoxysilane via a Two-Step Process," J. Mater. Chem., vol. 19, pp. 9054-9062, 2009.

Hdach, H. et al., "Effect of Aging and PH on the Modulus of Aerogels," Journal of Non-Crystalline Solids, vol. 121, pp. 202-205, 1990.

Hench, L.L. et al., "The Sol-Gel Process," Chemical Reviews, vol. 90, No. 1, pp. 33-72, 1990.

Hrubesh, L.W. et al., "Thermal Properties of Organic and Inorganic Aerogels," J. Mater. Res., vol. 9, No. 3, pp. 731-738, 1994.

Hrubesh, L.W. et al., "Thin Aerogel Films for Optical, Thermal, Acoustic and Electronic Applications," UCRL-JC-117553 Preprint, International Symposium on Aerogels 4, Sep. 19-21, 1994, 17pgs, Berkley, CA.

Hund, J. F. et al., "Formation and Entrapment of Noble Metal Clusters in Silica Aerogel Monoliths by γ-Radiolysis," J. Phys. Chem. B, vol. 107, pp. 465-469, American Chemical Society, 2003.

Husing, N. et al., "Aerogels-Airy Materials: Chemistry, Structure and Properties," Angewandt Chemie International Edition, 37, (1998), pp. 22-45.

Ilhan, U.F. et al., "Hydrophobic Monolithic Aerogels by Nanocasting Polystyrene on Amine-Modified Silica," J. Mater. Chem., vol. 16, pp. 3046-3054, 2006.

Jang, K.Y. et al., "Study of Sol-Gel Processing for Fabrication of Hollow Silica-Aerogel Spheres," J. Vac. Sci. Technol. A., vol. 8, No. 3, pp. 1732-1735, May/Jun. 1990.

Jones, S.M., "Aerogel: Space Exploration Applications," J. Sol-Gel Sci. Technol., vol. 40, pp. 351-357, 2006.

Kanamori, K. et al., "New Transparent Methylsilsesquioxane Aerogels and Xerogels with Improved Mechanical Properties," Advanced Materials, vol. 19, pp. 1589-1593, 2007.

Kanamori, K. et al., "Elastic Organic-Inorganic Hybrid Aerogels and Xerogels," J. Sol-Gel Sci. Technol., vol. 48, pp. 172-181, 2008.

Katti, A. et al., "Chemical, Physical and Mechanical Characterization of Isocyanate Cross-linked Amine-Modified Silica Aerogels," Chem. Mater., vol. 18, pp. 285-296, American Chemical Society, 2006.

Kim, N.K. et al., "Fabrication of Hollow Silica Aerogel Spheres by a Droplet Generation Method and Sol-Gel Processing," J. Vac. Sci. Technol. A. 7(3), (1989), pp. 1181-1184.

Kramer, S.J. et al., "Organically Modified Silicate Aerogels, 'Aeromisils,'" Mat. Res. Soc. Symp. Proc., vol. 435, pp. 295-300, Materials Research Society, 1996.

Leventis, N. et al., "Durable Modification of Silica Aerogel Monoliths with Fluorescent 2,7-Diazapyrenium Moieties. Sensing Oxygen near the Speed of Open-Air Diffusion," Chem. Mater., vol. 11, pp. 2837-2845, American Chemical Society, 1999.

Leventis, N. et al., "Using Nanoscopic Hosts, Magnetic Guests, and Field Alignment to Create Anisotropic Composite Gels and Aerogels," Nano Letters, vol. 2, No. 1, pp. 63-67, American Chemical Society, 2002.

Leventis, N. et al., "Nanoengineering Strong Silica Aerogels," Nano Letters, vol. 2, No. 9, pp. 957-960, American Chemical Society, 2002.

Leventis, N. et al., "Nanoengineered Silica-Polymer Composite Aerogels with No Need for Supercritical Fluid Drying," Journal of Sol-Gel Science and Technology, vol. 35, pp. 99-105, Springer Science + Business Media, Inc. 2005.

Loy, D.A. et al., "Bridged Polysilsesquioxanes. Highly Porous Hybrid Organic-Inorgarnic Materials," Chem. Rev., vol. 95, pp. 1431-1442, 1995.

Loy, D.A. et al., "Alkylene-Bridged Polysilsesquioxane Aerogels: Highly Porous Hybrid Organic-Inorganic Materials," Journal of Non-Crystalline Solids, Vol. 186, pp. 44-53, 1995.

Loy, D.A. et al., "Sol-Gel Synthesis of Hybrid Organic-Inorgranic Materials. Hexylene- and Phenylene-Bridged Polysiloxanes," Chem. Mater., vol. 8, pp. 656-663, 1996.

Meador, M.A.B. et al., "Cross-Linking Amine-Modified Silica Aerogels with Epoxies: Mechanically Strong Lightweight Porous Materials," Chem. Mater., vol. 17, pp. 1085-1098, 2005.

Meador, M.A.B. et al., "Structure-Property Relationship in Porous 3D Nanostructures as a Function of Preparation Conditions: Isocyanate Cross-Linked Silica Aerogels," Chem. Mater., vol. 19, pp. 2247-2260, 2007.

Meador, M.A.B. et al., "Reinforcing Polymer Cross-Linked Aerogels with Carbon Nanofibers," J. Mater. Chem., vol. 18, pp. 1843-1852, 2008.

Meador, M.A.B. et al., "Structure-Property Relationships in Porous 3D Nanostructures: Epoxy-Cross-Linked Silica Aerogels Produced Using Ethanol as the Solvent," Applied Materials & Interfaces, Vol. 1, No. 4, pp. 894-906, 2009.

Moner-Girona, M. et al., "Micromechanical Properties of Silica Aerogels," Applied Physics Letters, vol. 75, No. 5, pp. 653-655, Aug. 2, 1999.

International Search Report and Written Opinion issued Feb. 8, 2012 in corresponding PCT Patent Application No. PCT/US2011/033774.

* cited by examiner

HIGHLY POROUS CERAMIC OXIDE AEROGELS HAVING IMPROVED FLEXIBILITY

CROSS-REFERENCE TO PRIOR-FILED APPLICATIONS

This application is a continuation-in-part of U.S. patent application Ser. No. 11/948,315 filed Nov. 30, 2007, the contents of which are incorporated herein by reference.

STATEMENT OF GOVERNMENT-SPONSORED RESEARCH

This invention was made with government support under Contract No. NNC06ZA46A awarded by NASA The government has certain rights in this invention.

BACKGROUND OF THE INVENTION

1. Field of the Invention

Ceramic aerogels are among the most highly porous and lowest density materials. Their high porosity means that 95% or greater of the total bulk volume of a ceramic aerogel is occupied by empty space (or air), producing excellent thermal as well as sound insulating qualities. In addition, their high specific surface area (e.g. on the order of 600-1000 $m^2/g$) should make them well suited for numerous applications, including as adsorbent beds for chemical separations, as catalyst supports, as platforms for solid state sensors, etc. Unfortunately, conventional ceramic aerogels are physically and hydrolytically very unstable and brittle. Their macro-structure can be completely destroyed by very minor mechanical loads or vibrations, or by exposure to moisture. In addition, over time these materials tend to produce fine particles (dusting) even under no load. Consequently, there has been little interest in ceramic aerogel monoliths for the above-mentioned as well as other applications, despite their excellent insulative properties, simply because they are not strong enough to withstand even minor or incidental mechanical stresses likely to be experienced in practical applications.

2. Description of Related Art

U.S. Patent Application Publication No. 2004/0132846, the contents of which are incorporated herein by reference, describes an improvement wherein a diisocyanate is reacted with the hydroxyl groups prevalent on the surfaces of secondary ($\phi$ 5-10 nm) particles of a silica aerogel to provide a carbamate (urethane) linkage. Additional diisocyanate monomers are further polymerized to produce a network of polyurea chains between the carbamate linkages of respective pairs of hydroxyl groups present on the secondary particles, resulting in a conformal polyurea/polyurethane coating over the silica backbone. The resulting structure was found to have only modestly greater density than the native silica gel (2-3 times greater), but more than two orders of magnitude greater mechanical strength, measured as the ultimate strength at break for comparably dimensioned monoliths.

More recent work has demonstrated that the production of such polymeric conformal coatings is not limited to diisocyanate linkages anchored from surface-native hydroxyl groups. Alternative polymeric architectures have also been shown to produce conformal coatings that dramatically improve the strength of ceramic aerogels. Specifically, non-native functional groups (e.g. amine or vinyl groups) can be incorporated into the surfaces of aerogel secondary particles and used as anchors for other polymeric cross-linking chemistries (such as epoxy and styrene). Methods and chemistries for such alternative polymeric cross-linking architectures are described herein as well as in co-pending, commonly-owned U.S. patent application Ser. No. 11/266,025 and the following publications the contents of all of which are incorporated herein by reference in their entirety:

1. Structure-Property Relationships in Porous 3D Nanostructures as a Function of Preparation Conditions: Isocyanate Cross-Linked Silica Aerogels. Meador, M. A. B.; Capadona, L. A; McCorkle, L.; Papadopoulos, D. S.; Leventis, N., *Chem. Mater.* 2007, 19, 2247-2260.
2. Flexible, low-density polymer crosslinked silica aerogels. Capadona, L. A., Meador, M. A. B., Alunni, A., Fabrizio, E. F., Vassilaras, P., and Leventis, N. *Polymer,* 2006, 47, 5754-5761;
3. Chemical, physical and mechanical characterization of isocyanate cross-linked amine modified silica aerogels. Katti, A.; Shimpi, N.; Roy, S.; Lu, H.; Fabrizio, E. F.; Dass, A.; Capadona, L. A.; Leventis, N. *Chem. Mater.* 2006, 18, 285-296.
4. Cross-linking amine modified silica aerogels with epoxies: mechanically strong lightweight porous materials. Meador, M. A. B., Fabrizio, E. F., Ilhan, F., Dass, A., Zhang, G., Vassilaras, P., Johnston, J. C., and Leventis, N., *Chem. Mater.,* 2005, 17, 1085-1098.
5. Hydrophobic monolithic aerogels by nanocasting polystyrene on amine-modified silica. Ilhan, U. F.; Fabrizio, E. F. McCorkle, L.; Scheiman, D. A.; Dass, A.; Palczer, A.; Meador, M. A. B.; Johnston, J. C. and Leventis, N., *J. Mater. Chem.,* 2006, 16 3046-3054.
6. Bridged Polysilsesquioxanes. Molecular-Engineered Hybrid Organic-Inorganic Materials. Loy, D. A.; Shea, K. J. *Chem. Mater.* 2001, 13, 3306-3319.
7. Bridged Polysilsesquioxanes. Highly Porous Hybrid Organic-Inorganic Materials. Loy, D. A.; Shea, K. J. *Chem. Rev.* 1995, 95, 1431-1442.
8. Sol-Gel Synthesis of Hybrid Organic-Inorganic Materials. Hexylene- and Phenylene-Bridged Polysiloxanes. Douglas A. Loy, Gregory M. Jamison, Brigitta M. Baugher, Sharon A. Myers, Roger A. Assink, and Kenneth J. Shea, *Chem. Mater.* 1996, 8, 656-663
9. U.S. Patent Application Publication No. 2006/021621
10. Aryl-Bridged Polysilsesquioxanes-New Microporous Materials. Kenneth J. Shea* and Douglas A. Loy, *Chemistry of Materials* 1989, 1, 572-574.
11. A Mechanistic Investigation of Gelation. The Sol-Gel Polymerization of Precursors to Bridged Polysilsesquioxanes. Kenneth J. Shea and Douglas A. Loy Acc. Chem. Res. 2001, 34, 707-716.
12. Tailored Porous Materials. Thomas J. Barton, Lucy M. Bull, Walter G. Klemperer, Douglas A. Loy, Brian McEnaney, Makoto Misono, Peter A. Monson, Guido Pez, George W. Scherer, James C. Vartuli, and Omar M. Yaghi. *Chem. Mater.* 1999, 11, 2633-2656.
13. U.S. Patent Application Publication No. 2007/0203341
14. U.S. Pat. No. 5,321,102
15. U.S. Pat. No. 6,284,908

The polymer cross-linked aerogels described and referred to above exhibit far greater strength than the corresponding native ceramic aerogels (as much as two orders of magnitude greater strength with only a two- to three-fold increase in density). However, despite their improved strength they still remain relatively inflexible and are subject to brittle failure. Consequently there are numerous applications that could benefit from the insulative and improved mechanical properties of ceramic aerogels as described in the aforementioned publications, but where additional flexibility is necessary or would be desirable. For example, space-suit insulation could benefit significantly from more flexible ceramic aerogels having the insulative properties described above.

Accordingly, it is desirable to produce ceramic oxide aerogels as above, but which exhibit a greater degree of flexibility.

SUMMARY OF THE INVENTION

A ceramic-oxide network is provided, which includes the structure -M-L-M-, wherein M is a metallic or semi-metallic element common to the ceramic oxide network, and L comprises a linkage between the opposing M atoms in the structure, L having the form $-[X(R^2)_2]_n-$, wherein: X can be C or a heteroatom, each $R^2$ independently is any side group that will not prevent reaction(s) used to synthesize said ceramic oxide network including the -M-L-M-structure, and n is a positive integer between 2 and 10.

A method of preparing a ceramic-oxide network is also provided, which includes copolymerizing a reaction mixture that includes at least one ceramic-oxide precursor species and at least one flexible-linkage precursor through one or a series of chemical reactions to produce the ceramic-oxide network. The at least one ceramic-oxide precursor species includes a metallic or semimetallic element bound to at least one moiety through a bond that is labile under conditions of the aforementioned one or a series of chemical reactions. The at least one flexible-linkage precursor has the form $(R)_y(R^1)_x\text{-M-L-M-}(R^1)_{x'}(R)_{y'}$ wherein:

M is a metallic or semi-metallic element;
each R is attached to the associated M atom via a bond that is labile under the conditions of the aforementioned reaction(s) and is individually selected to be an alkyl, alkoxy or other group that will not prevent that/those reaction(s);
each $R^1$ is attached to the associated M atom via a bond that is not labile under the conditions of the aforementioned reaction(s) and can be individually selected to be an alkyl or other group that will not prevent that/those reaction(s);
L includes a chain linkage between the opposing M atoms that has the form

$-[X(R^2)_2]_n-$ wherein X can be C or another atom in the chain between the opposing M atoms, each $R^2$ independently is any side group that will not prevent reaction(s) used to synthesize said ceramic oxide network incorporating said flexible linkage, and n is a positive integer in the range of 2-10;
x and y are both integers with y being not less than 1, wherein the sum x+y is equal to the valence of M minus 1; and
x' and y' are both integers with y' being not less than 1, wherein the sum x'+y' is equal to the valence of M minus 1.

A silica network prepared from co-polymerization of alkyl(trialkoxy)silane and bi-silyl linking groups is also provided. The bi-silyl linking groups having the form $(RO)_3-Si-R^2-Si-(OR)_3$, wherein: R is an alkyl group, and $R^2$ is selected from the group consisting of a) substituted and unsubstituted $C_{2-6}$ alkyl groups, and b) $-R^3-X-R^3-$, wherein each $R^3$ is independently selected to be a substituted or unsubstituted $C_{2-6}$ alkyl group, and X is a functional group selected from the group consisting of amines, vinyls, thiols, acrylates and halides.

A method of making a monolith is also provided, which includes combining an alkyl(trialkoxy)silane with a bi-silyl linking group in an organic solvent to form a reaction mixture, the bi-silyl linking group having the form $(RO)_3-Si-R^2-Si-(OR)_3$, wherein R is an alkyl group and $R^2$ is selected from the group consisting of substituted and unsubstituted $C_{2-6}$ alkyl groups and $-R^3-X-R^3-$, wherein each $R^3$ is independently selected to be a substituted or unsubstituted $C_{2-6}$ alkyl group, and X is a functional group selected from the group consisting of amines, vinyls, thiols, acrylates and halides; and co-polymerizing the alkyl(trialkoxy)silane and the bi-silyl linking group to form a silica wet gel.

A further silica network is also provided, which is prepared from co-polymerization of vinyl(trialkoxy)silane and bis[3-(trialkoxysilyl)alkyl]disulfide linking groups.

BRIEF DESCRIPTION OF THE DRAWINGS

FIG. 24b illustrates the same data as FIG. 24a, but for a reduced ordinate scale of 0 to 1.6.

Drawings of chemical structures are schematic in nature, are not drawn to scale and are not intended to convey any information regarding the actual number, concentration and/or arrangement of illustrated chemical chains, particles, functional groups, flexible linkages or any other species or portion of a species within a ceramic oxide network. As will be appreciated, the arrangement of these items in the chemical structure drawing figures are for illustrative purposes, and their purpose is simply to schematically illustrate the relationships between the various chemical species, groups, chains and particles as further described herein.

Summary of Sol Gel Chemistry

Aerogels are made by extracting liquid from a solvent-filled gel, to leave behind just a solid-phase three-dimensional network of ceramic oxide particles. The wet gel generally is composed of the solid-phase ceramic oxide network of particles just mentioned, whose vast pore network is filled and occupied by a liquid phase material. The liquid phase material typically comprises or constitutes the solvent, other ancillary species (water, catalyst, initiator, buffer, etc., if present) and any remaining reactant species for forming the network of ceramic oxide particles via the sol gel process. Essentially, one can think of a wet gel and its cognate aerogel as the solvent-saturated solid network of ceramic oxide particles and the dried ceramic oxide network once the solvent has been extracted, respectively.

Figure 1:
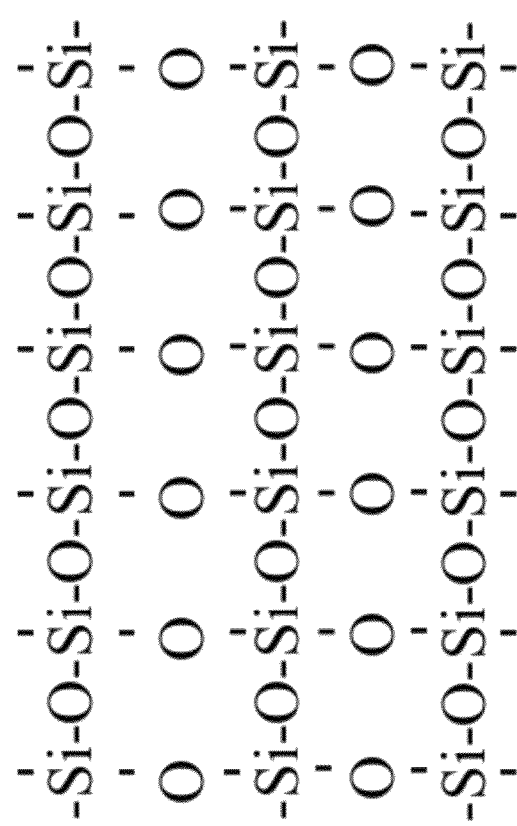
FIG. 1 is a simplified diagram of the structural formula for silica, illustrated in only two dimensions.

A ceramic oxide is an inorganic compound formed between a metallic or a semimetallic element and oxygen; e.g. silica ($SiO_2$), titania ($TiO_2$), alumina ($Al_2O_3$), etc. Generally, a network of ceramic oxide particles comprises a three-dimensional structure, with individual nanoparticles consisting of atoms of the metallic or semimetallic element(s) linked to one another via interposed oxygen atoms. For example, the network structure for silica is illustrated schematically in FIG. 1, though only in two dimensions. Because each silicon atom has four free valences, each is linked to four oxygen atoms. Correspondingly, because each oxygen atom has two donor electron pairs, each of them is linked to two silicon atoms except for oxygen at ceramic particle surfaces, which is linked to one silicon and forms a hydroxyl group. The resulting empirical chemical composition of the nanoparticles is near to $SiO_2$. It will be recognized and understood that other metallic or semimetallic elements having valences other than +4 (such as silicon) will result in correspondingly different chemical compositions in the network of nanoparticles. For example, aluminum has a valence of +3, resulting in the empirical formula $Al_2O_3$ for the corresponding ceramic oxide network. Beyond the foregoing, the only practical constraints for producing a ceramic oxide aerogel are that the metallic or semimetallic element must have a valence of at least, and preferably greater than, +2, and it must be amenable to forming a highly porous three dimensional network of nanoparticles comprising interposed oxygen bonds, e.g. via a sol gel process through reaction of appropriate ceramic oxide precursor species as hereinafter described. Alternatively, other mechanisms for producing such highly porous ceramic oxides can be used.

As evident above, a silica aerogel is prepared by extracting from the pore structure of the solid silica network of nanoparticles the solvent in which that network was made ("gelled"). The three-dimensional network of nanoparticles and the solvent within its pore structure are collectively referred to as a wet gel, also noted above. Briefly, a silica wet gel is made when an alkoxysilane (typically tetramethylorthosilicate or 'TMOS') is hydrolyzed in an appropriate solvent, typically methanol, ethanol, acetone, tetrahydrofuran or acetonitrile, to produce the resulting silica gel network and an alkyl hydroxide byproduct. The byproduct is methanol when TMOS is used. Alternatively, tetraethylorthosilicate or 'TEOS' also can be hydrolyzed to produce a silica gel network, in which case the alkyl hydroxide byproduct will be ethanol. The silica particles are formed through the linkage of silicon atoms in the solution ("sol") via oxygen radicals formed through hydrolysis and condensation. Thus, the silica gel is formed when the nanoparticles become numerous and coagulate against each other into a solid three-dimensional network. The gellation to produce the silica network is a form of cross-linking, wherein silica particles are 'cross-linked' via Si—O—Si linkages in neck regions between particles. However, the term 'cross-link' and cognates thereof are reserved herein for other polymeric linkages between particles that provide a polymeric, cross-linked conformal coating over the secondary particle structure of a ceramic gel as further described herein.

Figure 2:
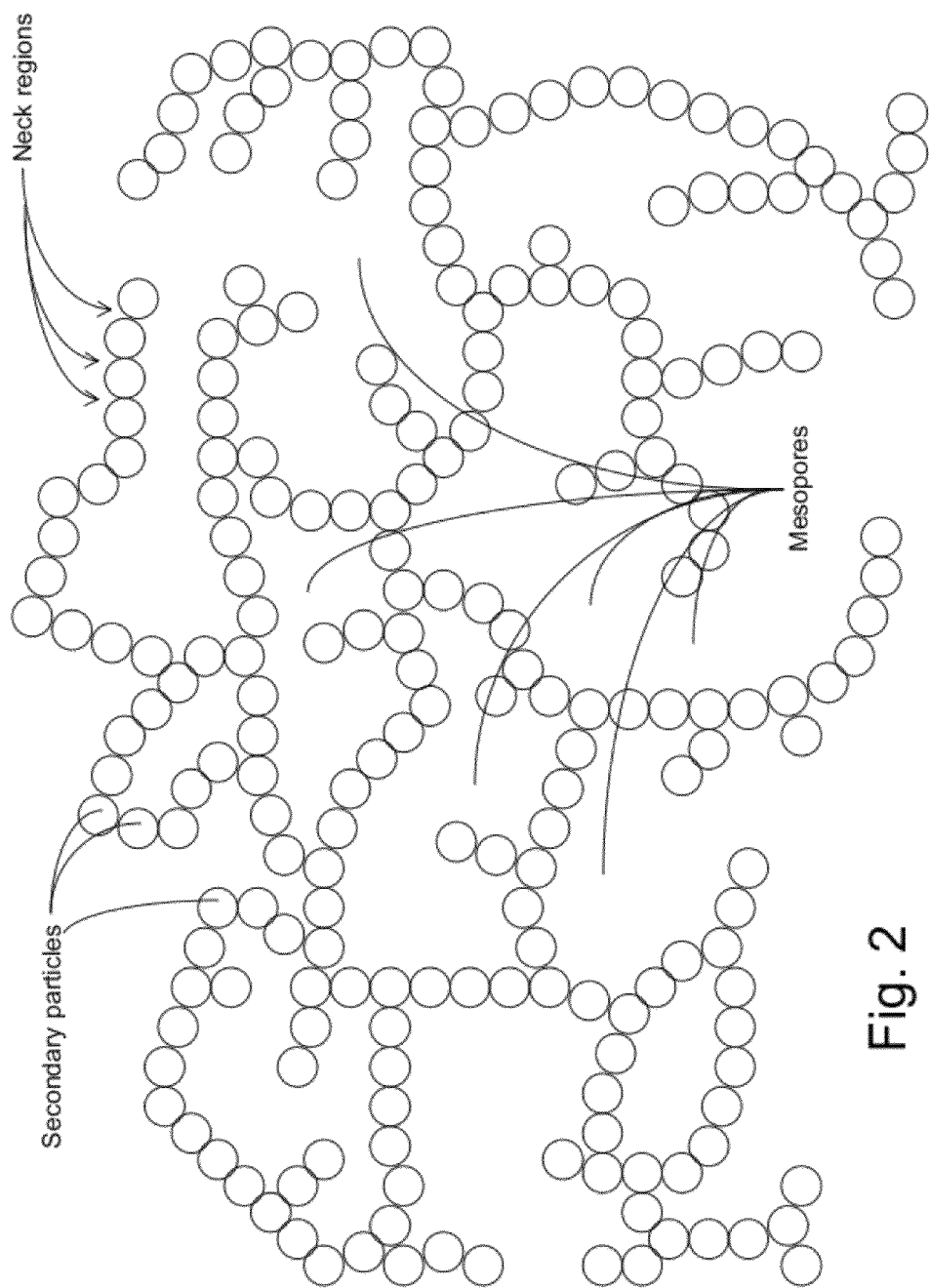
FIG. 2 is a schematic illustration of the structure of a solid silica network, composed of interconnected strands of secondary particles in pearl-necklace configuration.
Figure 3:
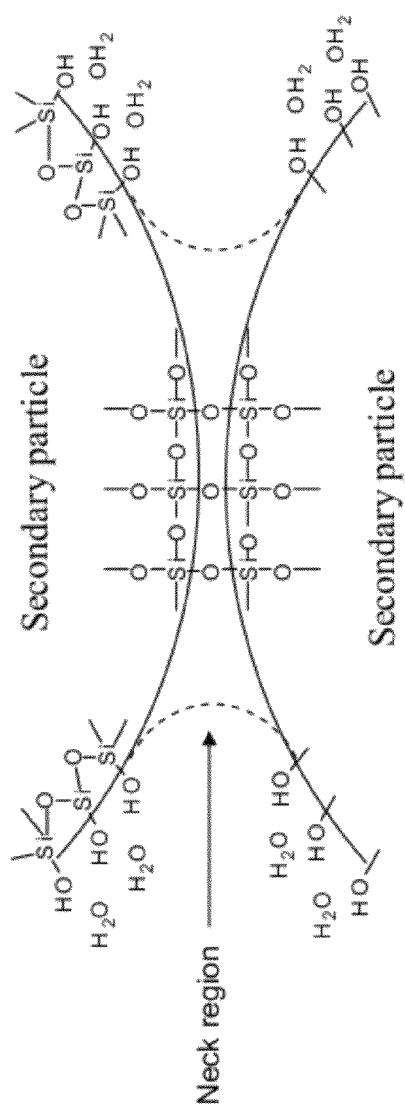
FIG. 3 illustrates two adjacent secondary silica particles linked at a neck region therebetween.

The hydrolysis reaction of the silicon alkoxide is spontaneous, but it occurs too slowly for practical applications (gellation can take days or longer to occur). Hence, it is conventional to employ an acid or a base catalyst, e.g. an amine catalyst, to accelerate the reaction to a more practical rate. On hydrolysis and condensation, the resulting solid silica network is formed having at least two distinct classes or orders of particles, namely primary particles with densities of 1.7 to 2.2 $g/cm_3$ and secondary particles with densities about half of that of the primary particles. The primary silica particles are tightly packed, fully dense solid particles having a particle size of less than 2 nm. The secondary particles have a particle size on the order of 5-10 nm (average particle size greater than 5 nm), and are nanoporous in that they are each made up of an agglomeration of the smaller primary particles. The nanopores in the secondary particles are provided as the space between the agglomerated primary particles that make up each secondary particle. The secondary particles are arranged to provide an interconnected network of long strands of the secondary particles to form a mesoporous structure as illustrated in FIG. 2. The secondary-particle strands are often referred to and known as a "pearl necklace" configuration. Within each such strand, secondary particles are linked with adjacent particles via Si—O—Si bonds across relatively narrow 'neck regions' between the particles as shown in FIG. 3. The empty space between the pearl necklace strands of secondary particles is referred to as mesoporosity and accounts for up to 95% of the total volume of the solid network's macrostructure, which is what affords these gels their desirable properties.

Once the solid silica network is formed, it is necessary to extract the solvent from the pore system (meso- and nanopores) of the solid network. Historically, this had been difficult to achieve while maintaining the structural integrity of the silica gel due to the presence of the mesopores in the solid network. The liquid-vapor interface produced on evaporation of liquid within the mesopores would exert strong surface tension forces that cause the collapse of the pore structure, causing the solid gels to fracture or shrink, often considerably compared to their initial size and form. To solve this problem, the solvent in the pore system of a silica wet gel is traditionally exchanged with liquid carbon dioxide above its vapor pressure. The resulting sol gel, now having liquid $CO_2$ in the pore system, is heated and pressurized beyond the critical temperature and pressure of $CO_2$, thus supercritically gasifying the $CO_2$ within the pore system of the solid gel network all at once. The supercritical carbon dioxide is vented, leaving behind the solid silica gel network thereby producing a dried silica aerogel whose physical structure is substantially unchanged and undamaged compared to the parent wet gel form. Converting the liquid $CO_2$ directly into supercritical $CO_2$ prior to venting results in there never being a liquid-gas interface in the mesopores of the gel; hence no surface tension forces are exerted on the pore surfaces and the solid structure remains intact. An alternative method for drying aerogels to limit shrinkage is solvent exchange with a low-surface-interactive solvent, such as pentane or fluorinated solvents. The solvent-exchange occurs progressively over several washings with increasing concentration of the low-surface-interactive exchange solvent for each washing. Once the solvent has been completely exchanged with such a low-surface-interactive solvent, the gel is removed and permitted to dry. This method should work best with aerogels that have been made somewhat hydrophobic. Styrene polymer-cross-linked gels (as described below) should be able to be dried in this way. One paper reports that this latter method can be practiced with isocyanate polymer-cross-linked gels (Leventis, Palczer, McCorkle, Zhang, Sotiriou-Leventis, *J. Sol-Gel Sci. Technol.* 2005, 35, 99-105), although it has not been found to provide very reproducible results in practice.

The supercritical. $CO_2$ or solvent-exchange drying methodologies described here (principally the $CO_2$ method) have remained necessary even for ceramic aerogels that include a conformal polymer cross-linked coating as described above in order to prevent or minimize shrinkage or collapse of the wet gels when drying to produce aerogels. As will be explained below, the introduction of a degree of flexibility into the secondary-particle skeleton of such gels may further reduce or eliminate the need for supercritical $CO_2$-mediated drying (or solvent-exchange methodologies described above, which have shown limited effectiveness) of the wet gels, which are costly and time-consuming.

DETAILED DESCRIPTION OF PREFERRED EMBODIMENTS

As used herein, whenever a range such as 5-25 (or 5 to 25) is given, this means preferably at least 5 and, separately and independently, preferably not more than 25.

A degree of additional flexibility can be imparted to ceramic aerogels via incorporation of flexible organic linkages between adjacent secondary particles in the mesoporous ceramic oxide network. This structure is illustrated schematically in FIG. 4. As can be seen in the figure, the ceramic oxide network is essentially the same as that in FIG. 2, except that flexible linkages (illustrated schematically as

)

have been interposed periodically between adjacent secondary particles, thereby segmenting the secondary-particle strands. By 'periodically,' it is meant that the flexible linkages described here redispersed throughout the secondary-particle network, not necessarily uniformly distributed or provided at regular intervals or periods, but at a relative frequency or 'concentration' based on the molar ratio of the flexible linkage precursor species relative to other ceramic oxide precursors that go into forming the ceramic oxide network, as will be further described. The interposition of these organic chains in between adjacent secondary particles in the ceramic oxide network, it is believed, has the effect of segmenting (i.e. breaking up or shortening) the 'pearl-necklace' strands of secondary particles, which are otherwise quite rigid based on their attachment within the neck regions as shown in FIG. 3. Specifically, the flexible linkages are believed to be more flexible than the direct particle-to-particle linkages that otherwise form between adjacent secondary particles in a ceramic oxide network, and to impart greater flexibility between shorter strands of pearl-necklace-configured secondary particles. The overall result is to produce a ceramic gel that exhibits a greater degree of flexibility than a native gel lacking interposed flexible linkages, whether or not the gel includes a polymeric cross-linked conformal coating as mentioned above and described more fully below.

The ceramic oxide aerogels with improved flexibility will be best understood through a description of a method by which they can be made.

A ceramic oxide network (whether or not functionalized with non-hydroxyl groups) is prepared preferably through a sol gel process. To introduce any desired non-hydroxyl functionality to the ceramic oxide, a functionalized ceramic oxide precursor that is compatible with sol gel chemistry to produce a solvent-filled gel of ceramic oxide network particles via a chemical reaction is copolymerized with an unfunctionalized ceramic oxide precursor via that reaction to produce the particle network. As used herein, an unfunctionalized ceramic oxide precursor is a species composed of a metallic or semimetallic element bound to other moieties all through bonds that are labile and subject to being broken under the conditions of the particular reaction that is or will be used to produce the ceramic oxide particle network of the wet gel (sol gel process); i.e. reaction-labile bonds. Conversely, a functionalized ceramic oxide precursor is a species composed of a metallic or semimetallic element that is bound to at least one non-hydroxyl functional group via a bond that is not labile (not subject to being broken) under those reaction conditions (i.e. non-reaction-labile), in addition to at least one, preferably more than one, other moiety via a bond that is labile under those conditions. As the particular chemical reaction proceeds, the solid network of nanoparticles is formed through copolymerization of both the unfunctionalized and any functionalized (if present) precursor species to produce a ceramic oxide wet gel having the desired non-hydroxyl functional groups (if any) attached to the network, in addition to the surface-bound hydroxyl groups that are native to ceramic oxides. As will be seen, at least a portion (probably a significant proportion) of the non-hydroxyl functional groups are surface-bound on the secondary ceramic oxide particles, probably displacing (taking the place of) a proportionate number or quantity of hydroxyl groups. Methods and species to introduce such non-hydroxyl functional groups will be more fully described below.

To provide flexibility to the resulting ceramic oxide gels, both wet and in the dried aerogel form, a precursor for a flexible linking species (sometimes referred to herein as a "flex link") precursor having the following general structure is incorporated into the reaction mixture prior to the gel-synthesis reaction described above:

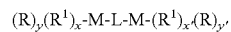

wherein:
M is a metallic or semi-metallic element common to the ceramic oxide network (e.g. Si for an $SiO_2$ network, Al for an $Al_2O_3$ network, etc.);
each R is attached to the associated M atom via a bond that is labile under the conditions of the reaction(s) that is or will be used to produce the ceramic oxide particle network from the ceramic oxide precursors (functionalized or unfunctionalized), and wherein each R can be individually selected to be any alkyl, alkoxy or other group that will not impermissibly interfere with or prevent the aforesaid reaction(s);
each $R^1$ is attached to the associated M atom via a bond that is not labile under the above-mentioned reaction conditions and can be individually selected to be an alkyl group or any other group that will not impermissibly interfere with or prevent the aforesaid reaction(s);
L is a flexible linkage between the opposing M atoms that can have any suitable form that is stable under the network-synthesis reaction conditions;
x and y are both integers with y being not less than 1, wherein the sum x+y is equal to the valence of M minus 1; and
x' and y' are both integers with y' being not less than 1, wherein the sum x'+y' is equal to the valence of M minus 1.

The R groups described above are termed leaving groups because they leave the associated M atom once the reaction-labile bond therebetween is severed; i.e. under the reaction conditions for synthesizing the network. The $R^1$ groups (if present) are retained with the associated M atoms, and therefore in the resulting network, because the bonds therebetween are not labile and thus not broken under the reaction conditions. During the reaction that forms the ceramic oxide network from the ceramic oxide precursor species, the reaction-labile bonds between the R (leaving) groups and M atoms in the flex link precursor are severed, and the resulting {-M-L-M-} linking species (with $R^1$s if present) is incorporated into the forming ceramic oxide network. It is to be noted that each such M may be linked to the ceramic oxide network via multiple bonds; i.e. up to y or y' bonds depending on the particular M atom.

In one embodiment, x and x' are both zero, and the formula for the flexible-linkage precursor reduces to $(R)_y$-M-L-M-$(R)_{y'}$, wherein y is between 1 and the valence of M minus 1. As described more fully below, it has been found that ceramic oxide aerogels prepared according to this methodology and using such exhibit a surprising degree of flexibility, both in the wet gel and dried aerogel states, and provide improved green strength for wet gels prior to polymer cross-linking via surface-bound functional groups as more fully described below.

The ceramic gels (wet gels and dried aerogels) with improved flexibility and processes for making them, described above in summary, will now be more fully described primarily with respect to the preparation of a flexible silica aerogel. However, it will be understood by persons of ordinary skill in the art that other ceramic oxides can be used based on selection of appropriate ceramic oxide precursor species, as well as flex link precursors, that can be reacted to produce a corresponding flexible ceramic oxide network based on another metallic or semimetallic atom, e.g. Al, V, Ti, Zr, etc.

To prepare a flexible silica aerogel, first the corresponding silica wet gel is prepared. Silica wet gels are prepared by hydrolyzing an alkoxysilane such as TMOS and TEOS to produce the wet gel having a solid silica particle network similarly as described above. TMOS or TEOS are unfunctionalized ceramic oxide ($SiO_2$) precursors, wherein all moieties attached to the central Si atom (methoxy for TMOS, ethoxy for TEOS) are attached via a reaction-labile bond, i.e. a hydrolysable bond based on the reaction mechanism by which $SiO_2$ gels are prepared. As used herein, a hydrolysable bond is one that is labile and subject to being broken under hydrolysis conditions employed to produce the solid silica network in the presence of water as a reactant, and a suitable catalyst if appropriate, so that the atoms linked by the hydrolysable bond become dissociated from one another. The moieties linked to the silicon (or other metallic or nonmetallic) atom via hydrolysable (labile) bonds are referred to as leaving groups, because following hydrolysis (or whatever the particular sol gel reaction used) they will be dissociated from (they will 'leave') the silicon or other metallic or semimetallic atom, and consequently will not be part of the resulting network.

To incorporate non-native (non-hydroxyl) functional groups to support polymer cross-linking as further described below, a functionalized silica precursor species is included in the hydrolysis reaction. To incorporate flexible linkages or 'flex links' into the ceramic oxide network, a flexible linking precursor of the form $(R)_{y'}(R^1)_{x'}$-M-L-M-$(R^1)_{x'}(R)_{y'}$, is incorporated into the network-synthesis reaction as mentioned above, wherein R, $R^1$x, x', y, y' M and L are all defined as above. The flexible linkage, L, is selected to provide a desired degree of flexibility to the resulting solid gel network and can take any suitable form. Throughout the remainder of this description, for brevity the case will be assumed where x and x' are both zero, meaning that only leaving groups, Rs, are attached to the M atoms in the flexible-linkage precursor. It will, of course, be appreciated that retained groups, $R^1$s, can be incorporated into any of the following methods to achieve desirable results, i.e. the incorporation of $R^1$ groups into the finished ceramic-oxide network in a concentration that is function of the concentration of flexible-linkages also incorporated.

In one embodiment, L can be a straight-chain hydrocarbon linkage (branched or unbranched), in which case the flex link precursor would have the form

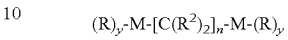

wherein:
M, R and y are as described above;
$R^2$ can be H or any substituted or unsubstituted alkyl, aryl or other group that will not impermissibly interfere with the reaction(s) that is or will be used to produce the ceramic oxide particle network from the ceramic oxide precursors (functionalized or unfunctionalized), and wherein each $R^2$ can be the same as or different from other Rs or $R^2$s; and
is a positive integer, preferably not more than 50, preferably not more than 40, preferably not more than 25, and most preferably is in the range of 2-25 or 2-20, and most particularly in the range of 2-10, 2-6 or 2-4.

The value of n in the above formula is most preferably 2-25 as mentioned above. Historically, shorter oligomers such as $(RO)_3Si(R^2)_{2-4}Si(OR)_3$ wherein M is selected to be silicon, were considered undesirable because they were known to produce ring structures that can prevent gelation. However, surprisingly and unexpectedly it has been discovered that values of n=2-6 produce flex link precursors that are suitable for use in silica aerogels. In particular, it has been found that properties of aerogels using flex-link precursors from 2-6 have produce aerogels with similar properties (density, strength, etc). Conversely, strands longer than n=25 may interfere with gelation through steric hindrance and/or by keeping the silica particles in solution.

To achieve maximum flexibility, it may be desirable that all $R^2$s in the above formula are hydrogens instead of branched side-chains or other moieties that may introduce steric or other hindrances to the flexing of the C-chain backbone of the flexible linkage. In an alternative to the embodiment shown above, the straight-chain hydrocarbon flexible linkage may include one or a number of unsaturated bonds so long as the overall flexible linkage remains sufficiently flexible. However, it is desirable to avoid unsaturated bonds in the flexible linkage to provide maximum flexibility, particularly for flexible linkages having a chain length, n, below 25 and more particularly for values of n equal to or lower than 10 or 6.

The flex link precursor is incorporated into the reaction mixture together with the alkoxysilane used to produce the ceramic oxide network. Specifically, in the case of a silica network that is to use a straight-chain flexible linkage to provide flexibility, the reaction mixture can include an alkoxysilane such as TMOS or TEOS and a flex-link precursor that can be in the form of a bi-siloxyl-terminal flex link precursor having the following form:

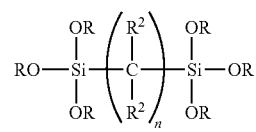

wherein R, $R^2$ and n are defined as above and Si, O and C each represent the respective atoms. The above structure assumes no retained (R¹) groups are attached to the Si atoms. Of course, such groups also can be provided, for example as reactive sites to anchor polymer-based cross-linking as described further below. In the embodiment now being discussed, no such retained groups are included in the flexible-linkage precursor.

The alkoxysilane and bi-siloxyl-terminal flex link precursor are combined and reacted with water under appropriate hydrolysis conditions to copolymerize them and produce a gelled network of silica particles comprising silicon atoms from the alkoxysilanes and the flex link precursor. Specifically, as the hydrolysis and condensation reactions proceed a silica network is formed consisting of silicon atoms from the alkoxysilane and the bi-siloxyl-terminal flex link precursor molecules that were originally present, wherein adjacent silicons are joined to one another via a —O— linkage to produce a solid network having the nominal empirical formula $SiO_2$ as mentioned above. Because the $-[CR^2{}_2]_n-$ linkage is stable (non-labile) under hydrolysis conditions, only the three —OR groups (with reaction-labile Si—O bonds) are removed from the bi-siloxyl-terminal flex link precursor during the synthesis reactions. Consequently, the Si atoms in that precursor remain linked to one another via the flexible $-[CR^2{}_2]_n-$ linkage, and are integrated into the network via Si—O—Si bonds at their three other valences.

Figure 4:
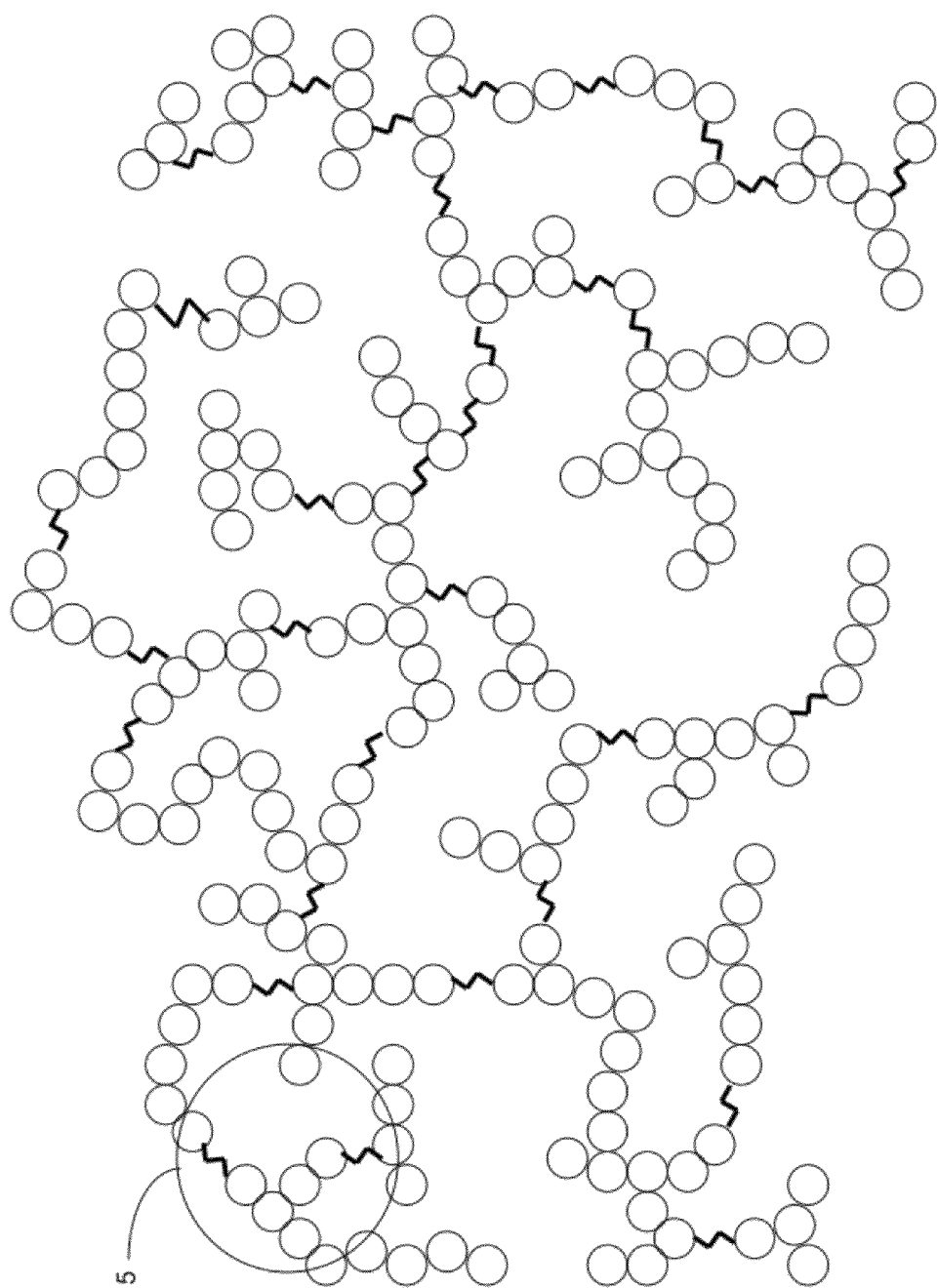
FIG. 4 is a schematic illustration of the solid silica network of FIG. 2, but incorporating flexible linkages as disclosed herein periodically dispersed throughout the network between adjacent secondary particles.

As mentioned previously, the resulting solid silica network (still a 'wet' gel because it is not yet dried of the reaction solvent) consists of secondary particles, each made of smaller and fully-dense primary particles, arranged in pearl-necklace configuration, with secondary-particle strands interlocking in three dimensions. The space defined between interlocking secondary-particle strands defines a mesoporosity of the network as illustrated in FIGS. 2 and 4, which contributes to volume void fractions of at least 80, preferably 85, more preferably 90, most preferably 95, percent, or higher as also mentioned above. In addition to the pearl-necklace strands, a silica gel prepared as above is believed to incorporate a plurality of flexible linkages consisting of the 'L' portion of the flex link precursors above (shown in FIG. 4, wherein the

segments correspond to the 'L' portion mentioned above). In the case of a silica gel made using the straight-chain flex link precursor shown above, those linkages will have the structural formula $-Si-[C(R^1)_2]_n-Si-$. It is believed the flexible linkages are primarily interposed between adjacent secondary particles periodically throughout the silica network as shown in FIG. 4, wherein they have the effect to break up the otherwise long pearl-necklace-configured chains of secondary silica particles, which are believed to be relatively rigid and inflexible.

It is believed that incorporation of large, sterically hindered species (such as the flexible linkages described herein) at the surfaces of the secondary particles of a ceramic oxide network is thermodynamically favored for a number of reasons compared to intra-particle incorporation. Without wishing to be bound by theory, the following is noted. First, the primary particles that make up secondary particles are fully dense, having substantially no porosity. Relatively bulky species such as the L groups mentioned above would be strongly sterically disfavored compared to the much more compact oxygen linkage (—O—) within and between the fully dense primary particles that make up secondary particles. In addition, the flex link precursor-source silicon atoms, having the non-hydrolysable bond to the L group, each have one less bonding site compared to the fully hydrolyzed silicon atoms from tetra-alkoxysilanes, which may tend to terminate network growth or linkage. If these silicon atoms were concentrated internally, they might be expected to disrupt gellation and the formation of a uniformly dense and fully expansive solid silica network. Such constraints are not present at the surfaces of the secondary particles. The secondary particle surfaces define a vast network of relatively large mesopores that can easily accommodate the steric bulk (compared to compact Si atoms) of flexible L groups concentrated at and extending from those surfaces. Furthermore, because the secondary particles are linked to one another only in relatively narrow neck regions to form the above-mentioned pearl necklace structure, silica network propagation above the secondary particle surfaces for the most part does not occur, and there is less need for a fourth Si-bonding site. For all these reasons the incorporation of the flexible linkages at and between adjacent secondary-particle surfaces within the silica network may be thermodynamically favored compared to intra-particle integration.

The observed behavior of wet gels and their corresponding aerogels prepared with flexible linkages also supports the conclusion that those linkages are incorporated between secondary-particle surfaces as illustrated in FIG. 4. Specifically, as seen in Example 3 below, wet gels have been produced that are highly flexible in that they can be bent into various configurations without breaking or fracture. As also seen below, wet gels can be dried to produce dry aerogels through simple air drying, without the need for supercritical $CO_2$-mediated drying or multiple solvent exchange steps, with no or negligible shrinkage and no perceptible fracture. These observed behaviors are explained by our theory that the flexible linkages described herein are incorporated primarily in between adjacent secondary particles dispersed throughout the network as shown in FIG. 4, thereby segmenting those strands. The incorporation of such flexible linkages, it is believed, has the dual effects of shortening the relatively rigid secondary-particle strands (by segmenting them) and enabling the resulting shorter strands to bend or flex relative to one another via the flexible linkages between them.

In addition to the straight-chain flexible linkages described above, the linkage, L, may also incorporate intermediate atoms other than C, for example nitrogen, so long as none of the bonds in that linkage are susceptible to hydrolysis under the network-synthesis conditions. In that case, the degree of polymerization, n, from above preferably corresponds to the total number of atoms in the chain, including C and non-C atoms. Several examples of flex link precursors that may be suitable to produce flexible linkages in a silica aerogel are listed below, which list is provided by way of example only and not limitation:

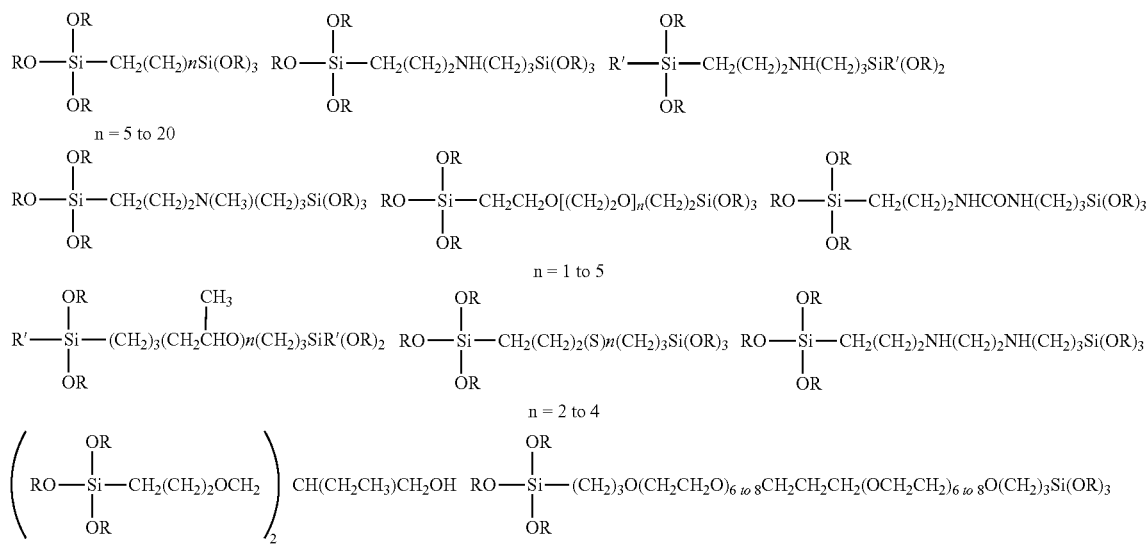

wherein Rs in each of the above can be individually selected as hydrogen, alkyl or other moieties but preferably are selected to be the same as one another in the same molecule, and R's above preferably are different from Rs attached to the same atom therewith.

In addition, the flexible linkage may also incorporate intermediate aromatic functionality or unsaturated side chains, for example:

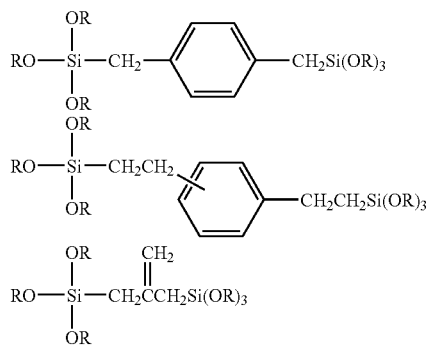

The flexible linkage portion, L, of the flex link precursor, and correspondingly the flexible linkage integrated into the silica network, may optionally include reactive side chains or other moieties to support a further cross-linking reaction. Specifically, as described in detail below it may be desirable to polymer cross-link the ceramic oxide network, and reactive moieties compatible with the polymer cross-linking chemistry that is used may be incorporated into the flexible linkages; provided that such moieties do not interfere with the network-synthesis reactions. Still further, the flexible linkages may also be provided or designed to impart additional desirable characteristics to the resulting flexibility-improved aerogel, such as groups that promote or increase fire retardance, polarity or charge-carrying characteristics or other desirable properties.

By interposing the flex, links into the secondary-particle strands, thereby reducing the effective length of the rigid particle-to-particle strands and providing flexible linkages in between them, the observed flexibility of the aerogels is increased. As will become evident below, the incorporation of flex-links into certain compositions of silica aerogel has been effective to eliminate the need for supercritical $CO_2$-mediated drying, with no apparent shrinkage or pore-structure collapse between the wet and dried-aerogel states. Without wishing to be bound by theory, it is believed that the flex links incorporated periodically throughout the ceramic network of interlocked strands of secondary particles increase the flexibility of the backbone network, thus permitting it to adapt more easily and to accommodate oppositely- or differently-acting forces that result from surface-tension effects as the solvent evaporates from the pore network. Specifically, by shortening the effective length of those strands, and introducing a flexible linkage in between the shorter strands, the whole network is believed to be made more flexible or malleable, and capable to adapt and flex in response to counteracting forces that otherwise may have caused brittle failure of a rigidly-constrained network. In other words, the rigid network is made more flexible by shortening its rigid members (the pearl necklace strands of secondary particles), and by introducing a flexible linkage periodically between adjacent ones of those strands.

Several examples of particular flex-link species have been discussed above. However, it will be evident that the selection or design of a particular flex-link species can be undertaken in each specific case to achieve an appropriate or desirable degree of flexibility as well as other physical characteristics. Such selection and/or design will be a matter of routine based on the present disclosure. For example, the degree of flexibility of the flexible linkages will depend on, among other things, the, length of that linkage, whether it is a straight-chain or branched, as well as other recognizable factors such as the prevalence of rotatable bonds. Much rotation is possible for carbon-carbon or carbon-heteroatom single bonds in a polymer chain. Alternatively, higher order (double or triple) carbon-carbon bonds as well as aromatic rings in the flexible linkages will restrict rotation, and may inhibit flexibility. Flexible linkages incorporating a high degree of these groups and/or unsaturated bonds may be expected to produce a lower degree of flexibility in the resulting aerogel for a given amount of the flex-link precursor introduced in the synthesis reaction.

Conversely, flex links having numerous ether linkages, which permit a high degree of rotation, will be substantially more flexible. The resulting flexibility of the overall aerogel may depend on the proportion of ether linkages in the flex links. At this point, it should be evident that a person having ordinary skill in the art will be able to design a wide variety of flexible-linkage architectures, based on a variety of structures, additive functional groups, other structural linkages and moieties to produce aerogels having characteristics suitable to any number of potentially desirable applications. Whether the flex-links include side groups or moieties capable to be cross-linked via the polymer cross-linking architecture described below is also a factor that will impact the overall degree of flexibility of the resulting aerogels.

Some amount of routine experimentation may be required to optimize or balance the contributions of competing effects of various moieties and/or side groups present in the flex links. But such experimentation will be within the capability of a person having ordinary skill in this art. In addition, numerous (e.g. two or more) different flex-link species (and corresponding flex-link precursors) may be used having differing structure; i.e. one may have few or no rotatable bonds and/or a shorter chain length compared to the other, and their ratio tuned to achieve a desired degree of flexibility. Of course, the total range of available flexibility may be constrained within broad limits based. The Examples below demonstrate that a large degree of adjustment is possible by varying at least the concentrations of the silane species (including functionalized, unfunctionalized and flex-link precursor species) that go into gel synthesis. A degree of adjustment should also be possible by varying factors such as those described above.

As already mentioned, in addition to improving flexibility it may also be desirable to polymer cross-link the secondary-particle pearl necklace strands in the aerogel to impart greater strength. Methods of providing such a cross-linking architecture to improve aerogel strength will now be described.

To provide such a polymeric cross-linking structure, methods described in publication US 2004/0132846 can be used, which rely on providing polyurethane linkages between native OH groups at the surfaces of secondary silica particles. However, it may be desirable to incorporate different, non-native (non-OH) functionality at those secondary particle surfaces to anchor the polymer cross-linking architecture, and/or to accommodate other cross-linking chemistries other than polyurethane, that would not necessarily be compatible with (able to link to) surface-bound OH groups.

To incorporate such non-native functional groups into the secondary-particle surfaces, a functionalized ceramic oxide precursor can be incorporated into the reaction mixture for forming the gel network as mentioned above. Like the alkoxysilane species also described above, which contains a silicon atom bonded to other species via only hydrolysable bonds, a functionalized silica precursor species includes a silicon atom bound to at least one, preferably to at least two, most preferably to three, other moieties via a hydrolysable bond (i.e. a bond that is labile under the particular reaction conditions), so the silicon atom can be integrated into the silica network during the hydrolysis reaction, e.g. with TMOS or TEOS. In addition to the leaving group(s) attached to the silicon atom, the functionalized silica precursor species also has at least one non-hydroxyl functional group attached to the Si atom via a non-hydrolysable (i.e. non-labile) bond. A non-hydrolysable bond is one that is not subject to being broken under the hydrolysis conditions noted above.

In an exemplary embodiment, it is desirable to incorporate amine functionality bound to the secondary-particle surfaces. In that case, a functionalized silica precursor such as 3-aminopropyl triethylorthosilicate or 'APTES' may be incorporated into the reaction mixture for making the silica aerogel. Similar to TMOS, which has four alkoxy moieties, APTES has three alkoxy moieties (ethoxy groups) linked to the central silicon atom via a hydrolysable bond. However, unlike TMOS, APTES also includes a fourth moiety that is a 3-aminopropyl group linked to the silicon atom via a non-hydrolysable Si—C bond. Under hydrolysis conditions, the three alkoxy bonds in APTES are broken and the associated ethoxy groups converted to ethanol. This frees three bonding sites on the silicon atom that now can be linked to oxygen atoms in the silica network, while the latter, fourth bond is not broken during hydrolysis. Consequently, the APTES-source silicon atom will continue to carry the 3-aminopropyl moiety with the terminal —$NH_2$ functional group after it is integrated in the silica network. In the case of silica formed from copolymerizing an alkoxysilane and APTES, it has also been found the resulting solid network exhibits the same basic hierarchical structure described above, having nanoporous secondary particles (particle size ~5-10 nm), composed of agglomerations of smaller and highly dense primary particles (particle size ~<2 nm), linked in long interconnected strands to produce an interconnected pearl necklace structure. It has been found that a large portion of the aminopropyl-linked silicons are located at the surfaces of the secondary particles, with the aminopropyl groups decorated over the secondary particle surfaces and extending into the superjacent void space (mesopores). It is noted that when APTES is used to provide amine functionality, it is unnecessary to incorporate a separate catalyst into the hydrolysis reaction because the amino groups on APTES provide more than adequate basic character to the sol to catalyze the hydrolysis reaction. In fact, it has been necessary in experiments to cool the TMOS/APTES solution/water mixture to slow the gellation rate and permit pouring of the sol into a desired mold prior to substantial gellation. In the case where it is desired to incorporate both surface-bound amine groups into the secondary particles as well as increased flexibility to the resulting silica aerogel, TMOS, APTES and the bi-siloxyl-terminal flexible linkage precursor all can be combined into the sol reaction mixture under hydrolysis conditions to produce the silica gel. The resulting gel structure is shown schematically in FIG. 5, wherein flexible linkages are illustrated periodically between adjacent secondary silica particles, and amine groups are shown decorated over the secondary-particle surfaces. The flexible linkages impart greater flexibility to the silica gel network as described previously, whereas the amine groups provide anchors for further polymer cross-linking structure to provide a conformal polymeric coating over the secondary-particle network as explained below.

It is believed, and experimental results have suggested, that integration of the APTES-source silicon atoms at the secondary particle surfaces is favored compared to intra-particle integration within the silica network. Potential explanations for the apparent preference of the aminopropyl-linked silicon atoms to be incorporated at secondary particle surfaces are similar to the reasons it is believed that the flexible linkages are incorporated primarily between secondary-particle surfaces and not within those particles. Specifically, the primary particles are fully dense with substantially no porosity, and the relatively bulky aminopropyl group ($NH_2$—$CH_2$—$CH_2$—$CH_2$—) would be strongly sterically disfavored compared to the much more compact oxygen linkage (—O—) within the fully dense primary particles. Thus, the APTES-source silicon atoms, having the non-hydrolysable aminopropyl group and therefore one less bonding site compared to the fully hydrolyzed silicon atoms from alkoxysilane, may tend to terminate network growth or linkage. If these silicon atoms were concentrated internally, they might be expected to disrupt gellation and the formation of a uniformly dense and fully expansive solid silica network. Furthermore, experimental evidence suggests that APTES itself does not gel. Hence both steric considerations and the lack of a fourth bonding site compared to the alkoxysilane-source silicon atoms suggest the APTES-source silicons would be relatively disfavored internally, within either the primary or the secondary silica particles. However, such constraints are not present at the surfaces of the secondary particles for reasons already explained. In addition to the above, hydrolysis of the alkoxy groups of APTES is slower than that of TMOS. Therefore, the incorporation of the APTES-source silicon atoms at the surfaces of secondary particles within the silica network may be thermodynamically favored compared to intra-particle integration of these silicons.

Figure 5:
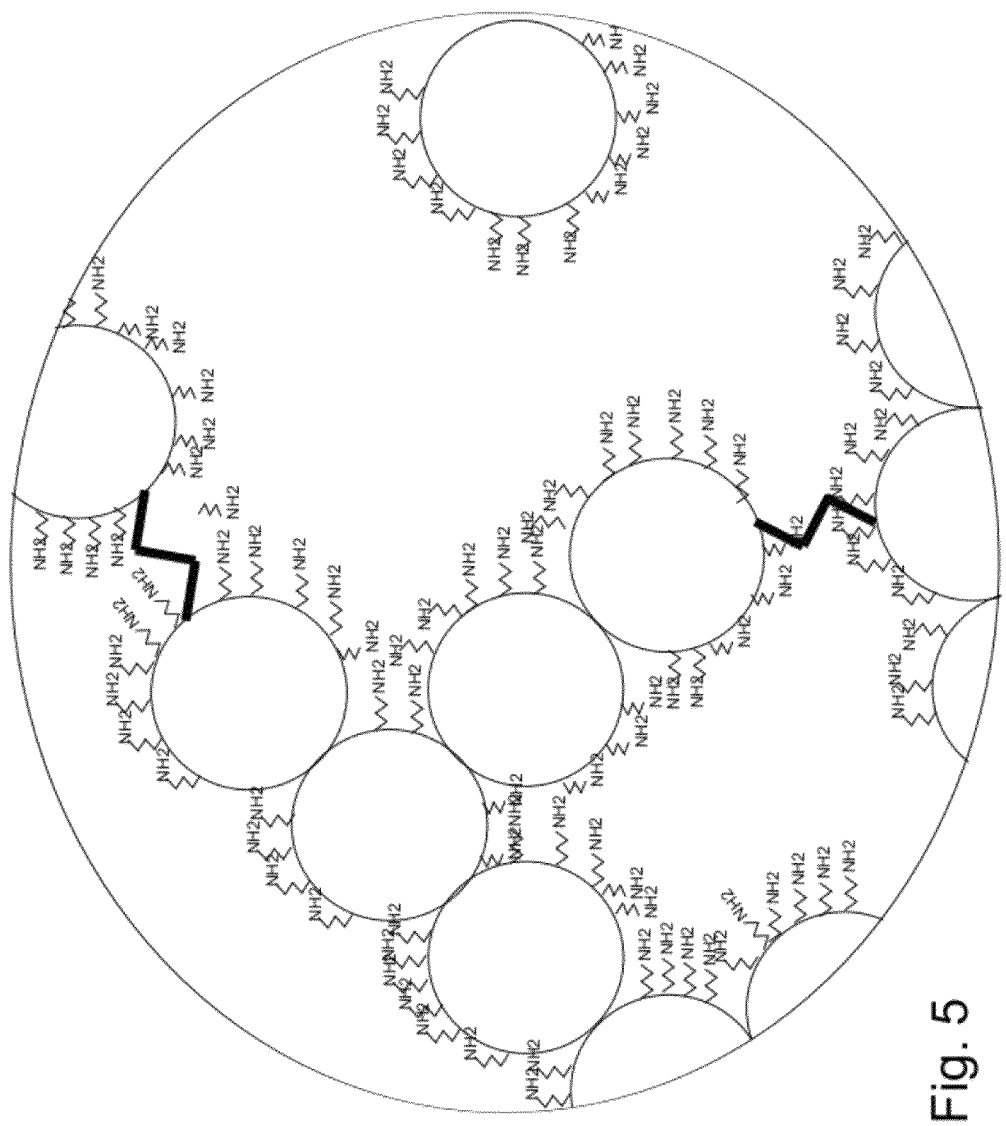
FIG. 5 is a close-up schematic illustration of the structure of the solid silica network taken at circle "5" in FIG. 4, showing interconnected strands of secondary particles having flexible linkages periodically dispersed therein between adjacent secondary particles, as well as non-native aminopropyl functionality incorporated at the surfaces of the secondary silica particles, for example by incorporation of APTES into the gel-synthesis reaction.

Following hydrolysis of TMOS, APTES and the bi-siloxyl-terminal flex link precursor species as described above, the resulting wet gel framework comprises a solid silica network having a structure illustrated schematically in FIG. 5 as noted above, wherein the

linkages will have the form —Si-L-Si—. Adjacent secondary particles in the secondary-particle strands are connected either directly to one another via —Si—O—Si— linkages between the surfaces of adjacent particles at relatively narrow neck regions (FIG. 3), or otherwise via flex links as illustrated in FIGS. 4-5. As noted previously, the flex links consist of the portion, L, of the flex link precursor species that is left once all hydrolysable bonds have been severed, leaving the terminal silicons free to interact and copolymerize during the hydrolysis/condensation reactions that propagate and form the silica network.

In FIG. 5, flex links are provided between adjacent secondary particles in conjunction with the incorporation of aminopropyl functional groups decorated over the surfaces of secondary particles. Of course, terminal hydroxyl groups also will be present on the surfaces of the secondary particles, however these are not illustrated. The surface-bound aminopropyl groups (or other non-native functional groups if so-incorporated) can be further reacted with a polymer or a polymerizable species, or other species that can serve as a base for linking or forming a polymer chain to the secondary particle surfaces as part of a polymer cross-linking structure between secondary particle strands in the solid silica network. Hence, while the flex links impart a degree of increased flexibility to the resulting aerogel, a polymer cross-linking structure (in the form of a conformal coating) can be used either to provide additional physical strength to the aerogel or enhance the flexibility depending on the nature of polymer (an elastic polymer structure, for example). It may even be possible to enhance both strength and flexibility. It is reiterated that while the solid silica network itself may be considered a 'polymer' produced from the copolymerization of TMOS, APTES (or other functionalized silica precursor) and the flex link precursor species, the term 'polymer' is reserved herein to refer to different, preferably organic, polymeric species or chains, non-native to a ceramic oxide network, that link or which are provided to cross-link that ceramic oxide network. The term 'cross-link' and cognate terms such as 'cross-linked,' 'cross-linking' and the like herein refer to linkages composed of polymeric structures non-native to the ceramic oxide network that extend between or link, or which are provided to link, different portions or points within that ceramic oxide network, either from native OH groups at the surfaces of secondary aerogel particles or from other, non-native functional groups provided at those surfaces, such as amine (e.g. aminopropyl) groups.

Whether or not it includes non-native functional groups at the secondary-particle surfaces (through incorporation of functionalized silica precursor species into the reaction mixture), the gel that is produced following the synthesis (hydrolysis and condensation) reactions is initially in the form of a sol gel or 'wet' gel whose porous structure is filled with the hydrolysis solvent, hydrolysis reaction byproducts (such as MeOH from TMOS, EtOH from the ethoxy groups of APTES as well as from TEOS if used, etc.) and other unconsumed species. If desired, at this point the wet gel can be cross-linked using a suitable polymer species or precursor (such as an appropriate monomer) to produce a conformal polymer cross-linked coating as referred to above. For example, the functional (amino) groups on the surfaces of the secondary particles can be reacted with an appropriate monomer or other species for forming or linking to a compatible polymer chain. Several different embodiments for providing such a conformal polymer cross-linked coating are described below.

In one embodiment a diisocyanate can be linked to the terminal amino groups on the surfaces of the secondary particles via a urea linkage according to equation (1) if the gel has been functionalized with amino groups.

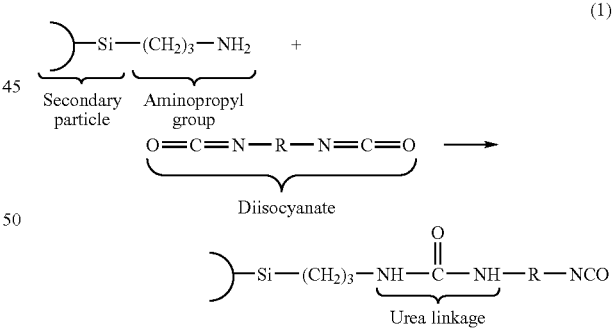

(1)

The resulting terminal isocyanate group, now attached to the secondary particle surface via the urea linkage, can be reacted (polymerized) with additional polyisocyanate groups to produce a polyurea polymer structure, e.g. as in Eq. 2.

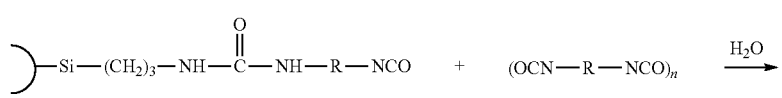

(2)

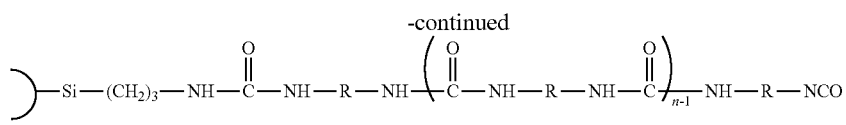

To drive this polymerization reaction water adsorbed on the silica surfaces is sufficient. The terminal isocyanate group in the product of Eq. 2 above likewise can be reacted with an amino group at the surface of the same or a different secondary particle to produce a polyurea linkage or 'cross-link' between two different secondary particles, for example between adjacent secondary particles in the neck region between them, or between different sites on the same secondary particle, Eq. 3.

In the immediately foregoing reactions, 'R' can be any group or moiety to which one or multiple —N=C=O groups can be attached, as the individual case may be. For example, 'R' can be or include a straight or branched alkyl or aryl group, aromatic group, olefinic group, or any combination of this, with or without additional functional species, so long as such additional functional species will not intolerably interfere with the formation of urea linkages between isocyanate groups on different monomers, or between an isocyanate

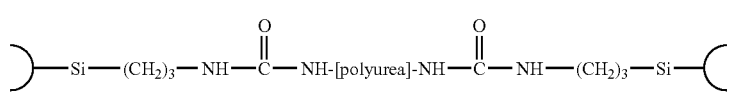

Alternatively, the above polymerization (cross-linking) reactions can be carried out with an isocyanate that is greater than 2-functional (i.e. having more than two functional NCO groups). For example, 3- and 4-functional isocyanates also can be used. It will be understood that just as in conventional polyurethane chemistry where isocyanates are prevalent, the greater the isocyanate functionality the more highly branched the resulting cross-linking polymeric structure will be, and consequently the more rigid and inflexible the resulting cross-linked ceramic oxide (silica) network may become. However, in applications where flexibility is of little concern, highly branched cross-linking structures may be desired to impart greater strength to the ultimate silica aerogel product (produced after the cross-linked sol gel is dried). This added strength will come at a cost in terms of a small increase in weight, however, because a more highly cross-linked aerogel will be more dense compared to uncross-linked aerogel. Alternatively, the degree of branching, regulated by isocyanate concentration, may be controlled in conjunction with the degree of introduced flexibility, regulated by the concentration of flex-link precursor in the network-synthesis reaction, to achieve an appropriate balance of the two effects and produce an aerogel having tunable or application-specific physical properties. Co-reactants can also be used with the 2-3- or 4-functional isocyanates to enhance flexibility. For example, OH-terminated glycols or amine-terminated ethylene oxides will co-react with the isocyanates to produce more flexible polymer cross-links.

In all of the above alternatives, polyurea chains that make up the polymer cross-linking may be linked together via branched polyurea chains, with the degree of branched linkages between the polymer chains depending in part on whether a 2-, 3- or 4-functional isocyanate is used for polymerization. Alternatively, mixtures of polyfunctional (2-, 3- and/or 4-functional) isocyanates also can be used. It will be further recognized there is the potential for additional cross-linking involving further reaction of secondary amine (—NH—) groups in polyurea to form tertiary amines (—N<) (allephanates and biurets, respectively), as is common to all polyurethanes. Still further, if appropriate side groups are provided on the flexible linkages as mentioned above, then the polyisocyanate or other cross-linking structure may be linked directly to the flexible linkages as well.

group and a surface-bound amine group in the ceramic oxide network. It is contemplated that 'R' can be provided or designed to impart additional desirable characteristics to the resulting polymer cross-linked ceramic oxide aerogel, for example incorporating additive functional groups as described more fully below.

As a further example, a polyepoxide also can be linked to a terminal amino groups on the surfaces of a secondary particles via an epoxy linkage as shown in Eq. (4).

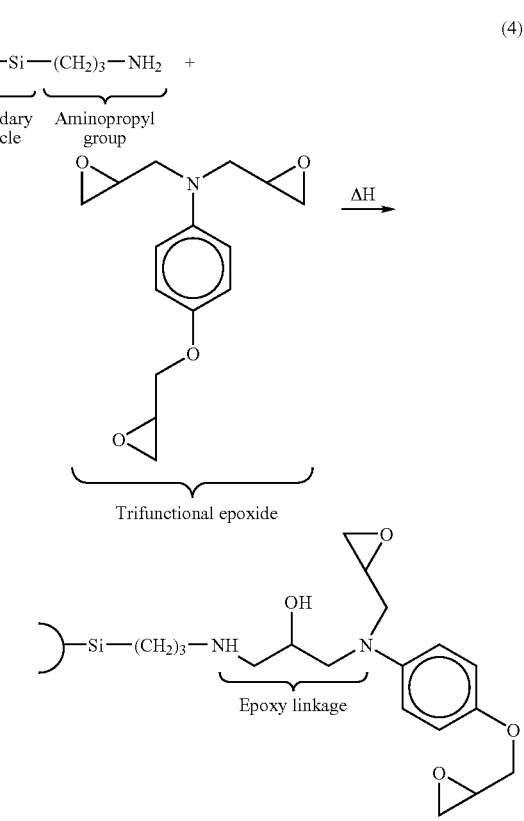

In Eq. 4, a trifunctional epoxide (N,N'-diglycidyl-4-glycidyloxyaniline) is reacted with the terminal amino group at the surface of the secondary particle. This results in a difunctional epoxide moiety attached to a secondary particle surface. Each of the epoxide groups of this difunctional epoxide moiety in the product of Eq. 4 can react (polymerize) with a) a yet-unreacted terminal amino group at the surface of the same or a different secondary particle, the latter resulting in inter-particle cross-linking, or b) at temperatures above 150° C., other epoxide groups attached to the surface of the same or a different secondary particle. An exemplary mechanism involving the difunctional epoxide product in Eq. 4 bound to each of two secondary particles, and a third secondary particle having an as-yet unreacted surface-bound amino group, is illustrated in Eq. 5.

loxybenzene as a difunctional epoxide monomer, Eq. 6, also is within the scope of the invention:

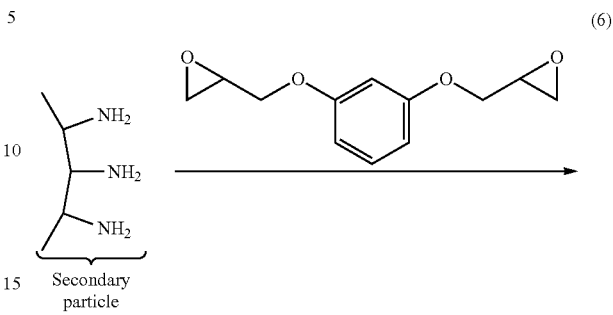

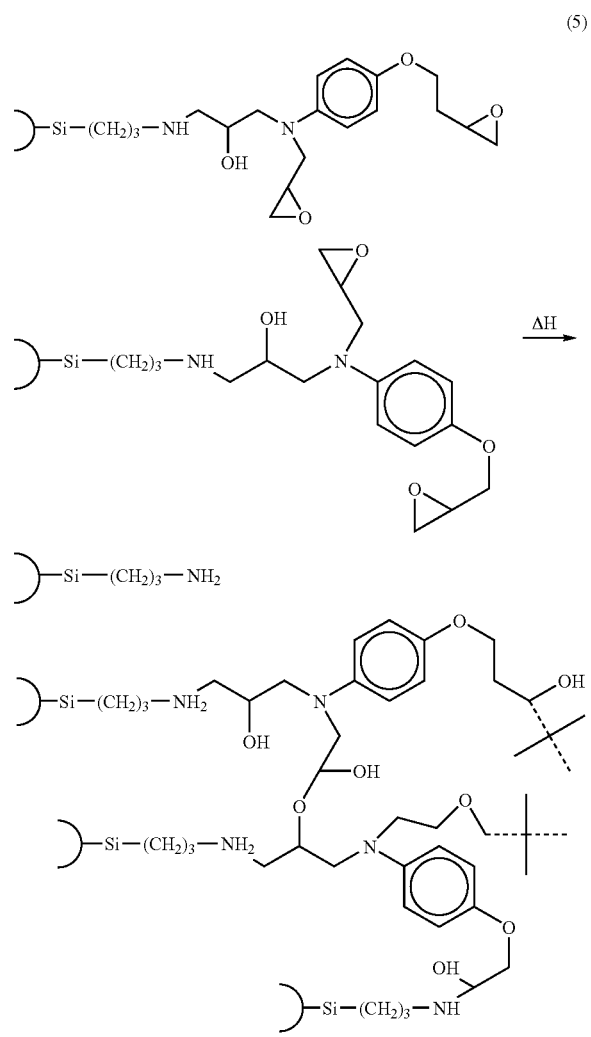

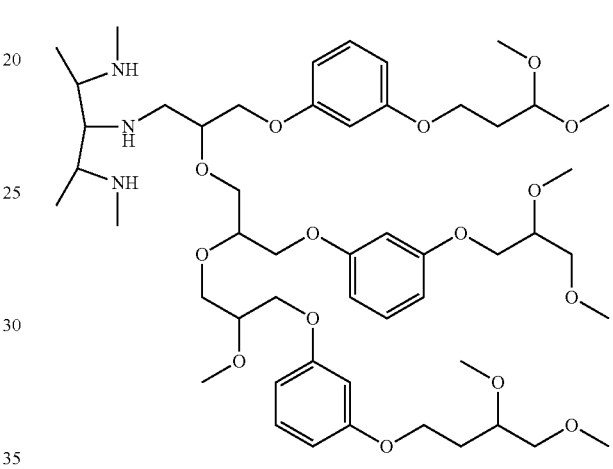

It will be understood that the exemplary mechanism shown in Eq. 5 is merely illustrative of numerous combinations of epoxide-epoxide and epoxide-amine reactions that are possible to produce a three dimensional polymeric epoxy network structure. In addition, it will be understood that di-, tetra-, or other polyfunctional epoxides also can be used, or combinations of them with each other or with tri-functional epoxides such as the one described above. For example, the following polymer network architecture using 1,3-diglycidy- A cross-linked epoxy polymeric network is produced via epoxy linkages between epoxide groups on different polyepoxide monomers (at temperatures above 150° C.), as well as between such groups and surface-bound terminal amino groups within the ceramic oxide particle network. (Epoxies also will react with SiOH surface groups, although to a much lesser extent.) The result is an epoxy cross-linked solid ceramic oxide (silica) network, in the form of a wet gel whose pore structure is saturated with the solvent used to carry out the epoxy polymerization reactions. Analogous with the polyisocyanate network discussed above, an epoxy polymeric network will provide epoxy linkages or 'cross-links' between different secondary particles, for example between adjacent secondary particles in the neck region between them, or between different sites on the same secondary particle. At elevated temperatures or in the presence of catalyst, branched epoxy linkages between epoxy polymer chains are also possible. Under conditions that have been employed to produce the epoxy cross-linked silica networks described here (no catalyst and relatively low temperatures), epoxides do not typically form large networks or chains of epoxy oligomer (monomer). Hence, under these conditions the resulting epoxy cross-linked silica network is primarily an epoxy monolayer over the surface of the secondary particle strands (pearl necklaces).

The foregoing discussion has been provided with respect to several specific di- and tri-functional polyepoxides. However, it will be understood that other polyfunctional epoxides having the general form:

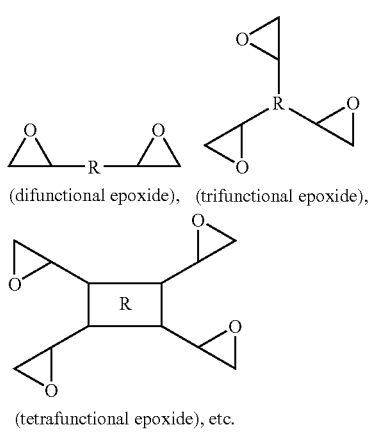

(difunctional epoxide), (trifunctional epoxide), (tetrafunctional epoxide), etc.

also could be used, where 'R' is or can be or include any structure compatible with the epoxy cross-linking chemistry, similarly as described above.

In still a further example of another polymeric cross-linking architecture, a styrene-containing species also can be linked to the terminal amino groups on the surfaces of the secondary particles via an appropriate linkage. The attached styrene group then can be reacted (polymerized) with other styrene-containing monomers to produce a polystyrene cross-linked polymeric network. For example, Eq. (7) below illustrates a reaction for attaching a styrene group to a surface-bound terminal amino group attached to a secondary particle of the ceramic oxide network.

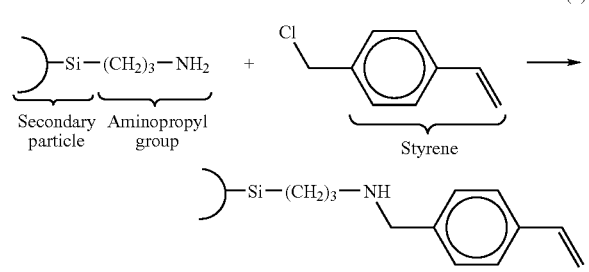

In Eq. 7, the styrene-containing species used to attach the styrene group to the terminal amine is 4-vinylbenzyl chloride, which contains a styrene moiety as shown in Eq. 7. This species is convenient because the terminal chloride reacts readily with the amine to link the amine and the residual p-methylstyrene moiety, producing HCl as a byproduct. In addition, other suitable styrene-containing species, having other functional groups that will react with the amino group to attach the styrene group to the ceramic oxide, can be used, (styrene functionalized epoxides, etc.). However, the preferred method is to co-polymerize p-trimethoxysilyl-styrene or vinyltrimethoxysilane (VTMS) (as the functionalized silica precursor) with TMOS, analogously to the copolymerization of APTES (though amine catalyst is necessary) to apply the styrene moiety directly to the surface of the nanoparticles.

Once styrene groups have been bound to internal surfaces of the solid ceramic oxide network, they can be reacted (polymerized) with other styrene monomers to produce a polystyrene cross-linked polymer network, for example as illustrated in Eq. 8. The styrene functionalized gels are placed into solutions containing the monomers of choice and AIBN as the initiator, and the polymerization occurs at elevated temperatures such as 75° C., or 75° C. to 100° C.

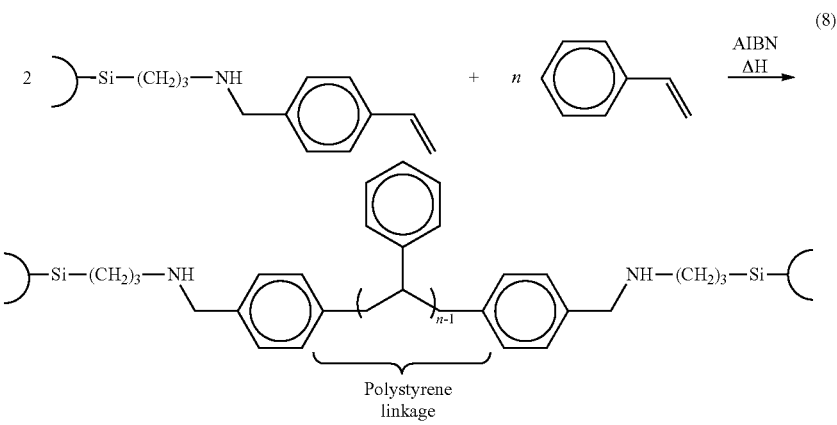

It will be understood that Eq. 8 is merely illustrative of a possible polystyrene cross-linking mechanism using native, non-functionalized styrene monomer to provide the polymeric cross-links. The actual cross-linked polystyrene network produced through polymerization of styrene monomers will include polystyrene chains of varying length depending on the concentration of additional monomer, extending between amino groups at the surfaces of different secondary particles, as well as between such groups attached to the surface of the same secondary particle. As with the previously described cross-linking species, polystyrene chains also may be provided between two adjacent secondary particles linked at a neck region in the same strand, as well as between different secondary particles in the same or in different strands. Also, alternatively to non-functionalized styrene monomer, other functionalized styrene-containing monomeric species (e.g. of the form R-[styrene], or R-[styrene]$_n$ also could be used. Similarly as before, 'R' can be or include any structure compatible with styrene polymerization to produce a polystyrene cross-linking architecture. Examples of styrene-containing monomeric species that have been successfully used to produce polystyrene cross-linked silica aerogels are 4-vinylbenzyl chloride and pentafluorostyrene, as well as mixtures thereof. It will be understood that to produce a branched polystyrene network, it may be necessary or desirable to incorporate at least some functionalized styrene-containing monomers, or otherwise monomers containing at least two styrene groups. Otherwise, pure, non-functionalized styrene may produce primarily straight and unbranched polystyrene chains as known in the art.

Also, generally it is desirable to utilize a radical initiator species to induce styrene polymerization. In the mechanism illustrated in Eq. 8, azobisisobutyronitrile (AIBN) is employed as a radical initiator. However, other suitable radical initiators can be employed, e.g. peroxy-based initiators including benzoyl peroxide can also be utilized under similar thermal conditions to obtain the polymerization.

As a further example, a polyamic acid also can be linked to terminal amino groups on the surfaces of the secondary particles via an anhydride linkage as shown in Eq. (9).

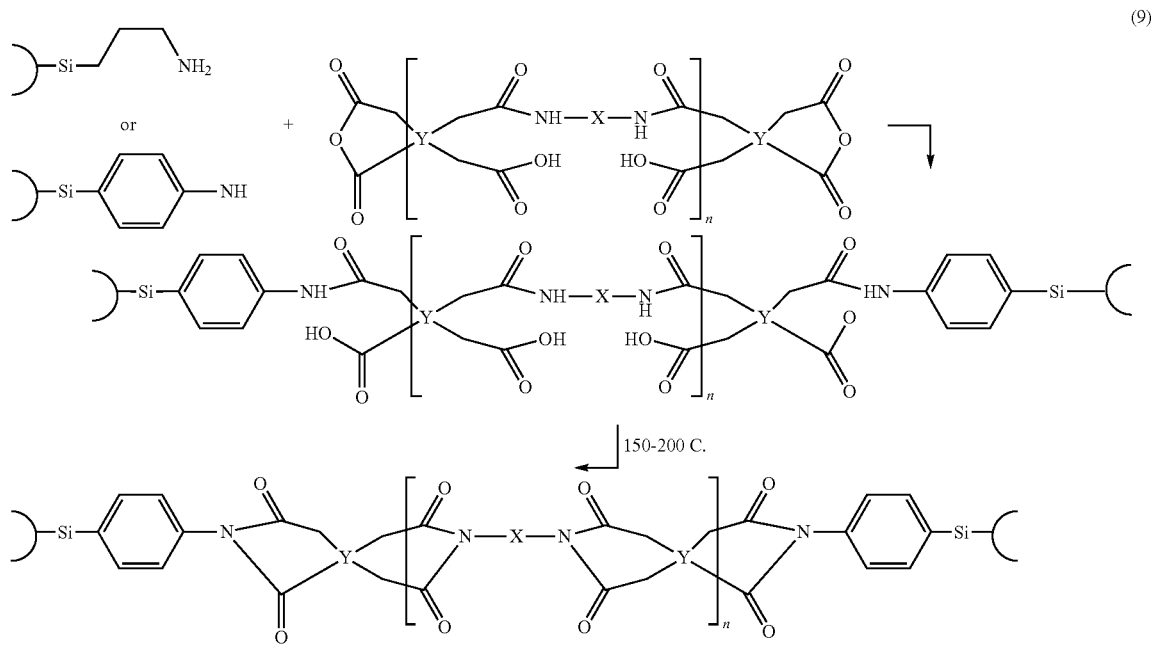

(9)

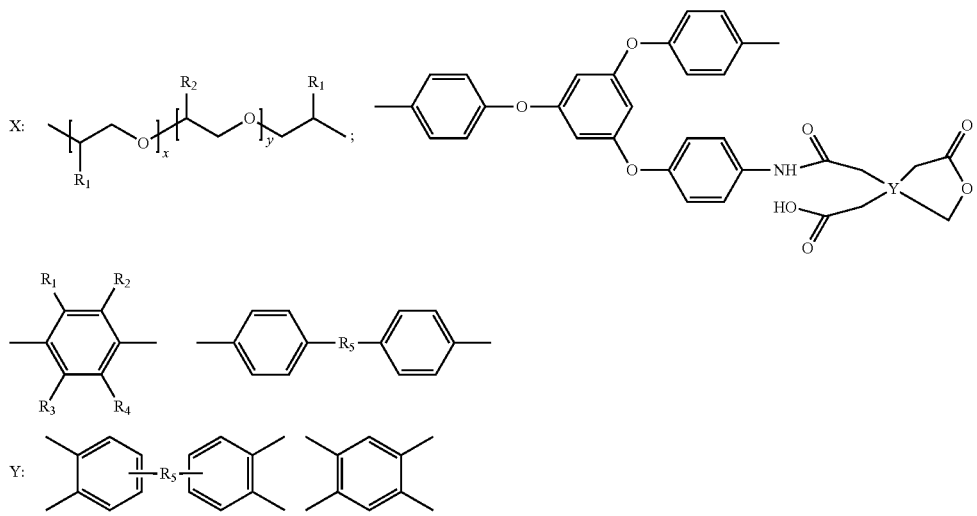

$R_1$ = H, $CH_3$, $CF_3$, alkyl, phenyl; $R_2$ = H, $CH_3$, $CF_3$, alkyl, phenyl
$R_3$ = H, $CH_3$, $CF_3$, alkyl, phenyl; $R_4$ = H, $CH_3$, $CF_3$, alkyl, phenyl
$R_5$ = nil, carbonyl, hexafluoroisopropylidene, methylene, oxygen
$R_6$ = nil, carbonyl, hexafluoroisopropylidene, methylene, oxygen In Eq. 9, a polyamic acid terminated with anhydride is reacted with terminal amino groups at the surface of the secondary particles. This results in amic acid moieties attached to secondary particle surfaces. Each of the anhydride groups shown in Eq. 9 can be reacted (polymerized) with a yet-unreacted terminal amino group at the surface of the same or a different secondary particle. Subsequent heating at temperatures of 150-200° C. promotes imidization giving a thermo-oxidatively stable cross-link. Incorporation of a tri-functional amine in the polyamic acid as shown in Eq. 10 allows n attachments of surface amines to anhydrides along oligomer backbones.

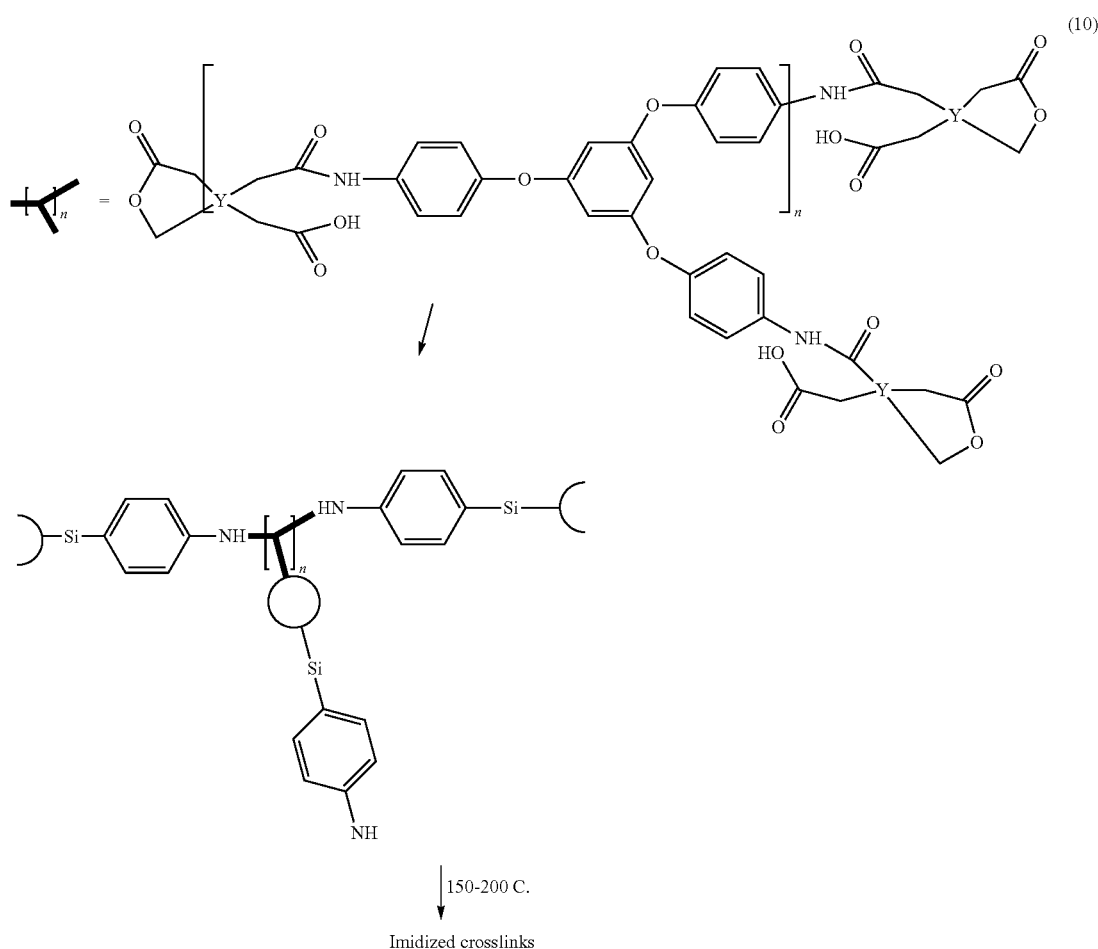

Imidized crosslinks

In addition to cross-linking the ceramic oxide via the isocyanate-, epoxy- and styrene-based polymer chains described above, other polymer architectures also could be used for cross-linking. The first step will be to select an appropriate base species or monomer to be attached to the ceramic oxide to support the desired polymer architecture. For example, a moiety including a free carboxylic acid group can be attached to the ceramic oxide if it is desired to produce a polyester cross-linking architecture. Alternatively, other functional groups also could be decorated to the ceramic oxide network, such as other olefins (polyolefin cross-linking architecture), alkyl or aryl halides (polybenzoxazole cross-linking), ketones or aldehydes (polybenzimidazole cross-linking), ethers (polyether cross-linking), etc. It should be evident that once the appropriate base or monomeric species has been decorated to the ceramic oxide network's internal surfaces, cross-linking is a matter of performing essentially the conventional cross-linking reactions, using conventional reaction conditions, associated species (such as catalysts and initiators), solvents, etc., with care taken to select conditions, solvents, etc. compatible with the solid ceramic oxide network. However, except for terminal hydroxyl groups, ceramic oxides are highly stable, inert materials, so there will be few instances where selection of appropriate cross-linking species and/or conditions will be impacted by the particular ceramic oxide sol gel to be polymer cross-linked.

It also will be evident that attachment of the desired base or monomeric species to the ceramic oxide network, e.g. to decorate the particle surfaces of such network with the functional groups that will support the desired cross-linking chemistry, will be a matter of routine based on the present disclosure. Broadly, one selects or designs a molecule having the desired reactive species to support cross-linking via the desired architecture, but also having another reactive site that can be used to attach the molecule (having the reactive species) to the ceramic oxide network. In the case of amine-decorated silica as above, the mentioned functional group is an amine, and the other reactive site is an (or more than one) alkoxysilane(s), e.g. three ethoxysilyl groups on APTES. Alternatively, if the native hydroxyl groups on ceramic oxide surfaces are to be used, then the reactive site should be reactive with such terminal hydroxyl groups to produce an analogous result. It will be understood that the cross-linking supportive functional group and the other reactive site to attach the molecule to the ceramic oxide network can be the same (as for the polyfunctional epoxides described above), or they can be different (as for 4-vinylbenzyl chloride, also described above).

In addition to the polymerizable moieties on the monomeric species used to cross-link the surface-bound functional groups either present or incorporated into a ceramic oxide network, such species also can have other chemical moieties effective to impart a desired property to the finished polymer cross-linked ceramic oxide aerogel composition. For example, any of the aforementioned monomeric species (epoxides, styrenes and isocyanates), as well as other monomeric species capable to support other cross-linking architectures, can have, e.g., attached phosphate group(s), which are known to impart flame retardant qualities to materials. As a further example, conducting polymers having free valence electrons capable to act as charge carriers can be incorporated into the monomeric species to impart a degree of electrical conductivity to the finished aerogel. As a still further example, catalytic species also can be incorporated in this manner. Other groups or moieties capable to impart other desired physical, chemical, electrical, magnetic, non-linear optical or other properties also can be incorporated in this manner, which incorporation would be within the ability of a person having ordinary skill in the art. Such groups that can be so incorporated into the polymer cross-linked aerogels through incorporation in monomeric (polymerizable) species used for cross-linking are broadly referred to herein as 'additive functional groups' because they impart added characteristics to the final aerogel. Alternatively, such groups can be added either by post-gellation treatment, or by post-cross-linking treatment with appropriate attachable molecules.

It is to be noted that numerous other species, moieties and/or side groups may be incorporated into the monomers that produce the selected polymer cross-linking architecture, similar to those described above for the flex-link precursors. For example, fire-retardant or other side-groups may be incorporated so that the polymer conformal coating will possess desirable properties and impart them to the overall aerogel. Similar considerations as mentioned above with respect to tuning the flexible linkages also will apply when designing and/or selecting appropriate cross-linking monomers and architecture. For example, while the flexible linkages described above can affect the flexibility of the underlying ceramic-oxide network, a degree of additional flexibility can also be introduced into the polymer conformal coating described here.

A mixture of different monomeric species having different overall structures also can be used to produce the polymer cross-linking structure for an aerogel so long as the different monomers have common or compatible polymerizable moieties; e.g. a styrene moiety or an epoxy moiety, etc. For example, the degree of flexibility of a polymer cross-linked ceramic oxide aerogel will depend, among other things, on the prevalence of rotatable bonds in the cross-linked polymer structure. Much rotation is possible for carbon-carbon or carbon-heteroatom single bonds in a polymer chain. Alternatively, higher order (double or triple) carbon-carbon bonds, a high degree of cross-linking as well as aromatic rings in the polymer chain do not permit significant rotation. Consequently, a polymer network composed primarily of highly cross-linked isocyanate (polyurea), or based on highly unsaturated monomers (significant degree of higher order bonds), will produce a relatively rigid, inflexible cross-linking structures. If it is nonetheless desired to produce a more flexible cross-linking structure, apart from the flexibility that is introduced to the underlying aerogel skeleton via the flex-links mentioned above, then a mixture of polyisocyanate monomers, e.g. one monomer having few or no rotatable bonds and another having longer chains between cross-links, can be used, and their ratio tuned to achieve a desired degree of flexibility in the cross-linked polymer structure. Of course, the total available range of available flexibility may be constrained within broad limits based on the cross-linking architecture selected, but some degree of adjustment should be possible through this technique.

Conversely, a cross-linked network based on epoxy chains, having numerous ether linkages, which permit a high degree of rotation, will be substantially more flexible, and its flexibility may depend on the proportion of ether linkages in the network. Still further, ether linkages can be provided in other, non-epoxy monomers, such as polyisocyanate monomers or polyimides using amine terminated polyalkyleneoxides in the polymer chain as shown in Eq. 9 above, to impart a greater degree of flexibility to the resulting cross-linking architecture as described above. At this point, it should be evident that a person having ordinary skill in the art will be able to design a wide variety of cross-linking architectures, based on a variety of polymerizable species, additive functional groups, other structural linkages and moieties within the polymerizable species, etc., to produce aerogels having characteristics suitable to any number of potentially desirable applications. There is virtually no limit to the applications for the potential variety of polymer cross-linked ceramic oxide aerogels that could be prepared by a skilled person based on the present disclosure.

The polymer cross-linking described above imparts a conformal coating over the surfaces of the secondary particles of the ceramic network. This coating has been shown to improve the mechanical strength of the finished and dried ceramic aerogels, but it does not improve the flexibility of the underlying ceramic-oxide network. To improve flexibility of the underlying aerogel the flexible linkages described above are also incorporated by providing appropriate flexible linkage precursors into the synthesis reaction mixture as above described. As will by now be appreciated, according to this approach both flexible linkages and a polymer cross-linked conformal coating anchored to native —OH and/or non-native functional groups can be incorporated directly into the pearl-necklace strands of secondary particles.

While the foregoing descriptions have been provided with respect to a silica network, the above cross-linking methods and methods to incorporate flex-links are not to be limited to silica, as the methods and reactions described herein to produce a cross-linked ceramic oxide and ceramic oxides having greater flexibility are also applicable to other ceramic oxides. For example, the methods and reactions described herein also could be used to produced other polymer cross-linked ceramic oxides, and ceramic oxides with improved flexibility, including but not limited to titania, vanadia, manganesia, zirconia, ruthenia, alumina, iron oxide, india (indium oxide), yttria, europia, etc., (which can be represented as $TiO_x$, $VO_x$, $MnO_x$, $ZrO_x$, $RuO_x$, $AlO_x$, $FeO_x$, $InO_x$, $YO_x$, $EuO_x$, etc., respectively). All of these ceramic oxides will have terminal hydroxyl groups present on internal surfaces thereof, which form the respective ceramic oxides and define their mesoporous networks. Accordingly, all, of these, as well as other ceramic oxides, can be cross-linked as described herein by using the surface-bound hydroxyl groups to attach the desired moiety to support the chosen cross-linking architecture. Alternatively, other ceramic oxides besides silica also can be produced having non-hydroxyl functional groups decorated to the internal surfaces thereof. Specifically, such other ceramic oxides can be produced via appropriate reactions analogous to the TMOS-APTES hydrolysis reaction for producing amine-decorated silica, with suitable ceramic oxide precursors based on the associated metallic or semimetallic element, "Z," having leaving groups attached to a central Z atom via reactive or reaction-labile bonds, and functional groups attached via non-reactive or non-reaction-labile bonds. For example, an alkoxy-Z and a functionalized $ZO_x$ precursor species, (a generic ceramic oxide being represented as $ZO_x$), having at least one functional group attached to the Z-atom via a non-reactive bond can be prepared by persons having ordinary skill in the art for the desired metallic or nonmetallic "Z" atom, and copolymerized via a sol gel process employing an appropriate reaction for producing a gelled ceramic oxide network decorated with the desired functional group. Alternatively, the ceramic oxide mesoporous network can be decorated with appropriate functional groups by post-gellation treatment with molecules having the desired functional groups that will support cross-linking via the desired chemistry, but also having another reactive site that can be used to attach the molecule (having the reactive species) to the ceramic oxide network, or one containing flex linkages and exhibiting improved flexibility as described herein. In that regard, such reactive site that can be used to attach said molecule to the ceramic oxide network can be based on the same metallic or semimetallic element "Z" as the ceramic oxide mesoporous network, or another element. For example, the mesoporous surfaces of a metallic or semimetallic ceramic oxide mesoporous network can be decorated with amines by post-gellation treatment with APTES, or it can be modified with styrene by post-gellation treatment with p-trimethoxysilyl styrene.

In addition, the flex-links mentioned herein, or analogous ones based on other metallic or semi-metallic elements, could likewise be incorporated into ceramic oxides based on other metallic or semi-metallic elements using the methodology herein described. For example, whereas the flex link precursor to be incorporated into the synthesis reaction for a silica aerogel may be:

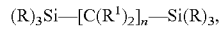

$(R)_3Si-[C(R^1)_2]_n-Si(R)_3,$ the analogous molecule may be incorporated into the synthesis reaction (with or without retained $R^1$ groups as described above) for other ceramic oxides, wherein Si is simply replaced by the corresponding metallic or semi-metallic element.

It is expected that not all metal and semimetal oxide mesoporous networks will be amenable to all these methods, and it is recognized and expected that some experimentation may be necessary to determine whether functionalized wet gel networks based on other, non-Si metallic or semimetallic elements can be prepared via sol gel chemistry to produce a gelled solid network. In addition, some ceramic oxides may require acid or base catalysis, different reaction conditions such as high temperature for endothermic reactions, low temperature for highly exothermic reactions, appropriate solvents, etc. However, such experimentation is well within the ability of a person having ordinary skill in the art, and will be routine based on the present disclosure once the desired ceramic oxide, the functional groups to be decorated thereto and the flex-link species have been identified for producing an aerogel with the desired properties. While some experimentation may be necessary to identify appropriate flexible linkages and precursors for them in a specific case, this will be within the capabilities of a person of ordinary skill in the art who has reviewed the present disclosure. For example, a matrix may be set up containing a variety of different proposed flex-link precursors for a particular ceramic aerogel, wherein individual candidate flex links have variable chain lengths, degrees of unsaturation, side groups, ether linkages, aromatic character, etc. Through routine testing, optimization of a ceramic oxide aerogel having appropriate flex-link character could be achieved, and appropriate flex links identified.

Regardless of whether any polymeric architecture is used to provide polymeric cross-linking, and of what ceramic oxide is employed, once the wet gel with flexible linkages is formed (and cross-linked) the next step is to remove the liquid (solvent) from that network to produce a dried aerogel. Conventionally, aerogels are prepared from the corresponding wet gel via a $CO_2$ exchange and supercritical drying procedure as described previously. While a polymer cross-linked conformal coating as described has been shown to improve aerogel strength, it has still been necessary to dry the cross-linked gels via the supercritical $CO_2$-mediated process, or in limited cases via solvent exchange through multiple steps to low-surface-interactive solvents such as pentane, to avoid pore-structure collapse and shrinkage as described above. As will become evident in one of the following examples, the incorporation of flexible linkages as herein described into a silica aerogel has been shown to permit air drying of the wet gel into its dried aerogel state without the use of supercritical $CO_2$ or solvent exchanges to special solvents and without any perceptible shrinkage or pore collapse. Accordingly, the combination of a polymer cross-linked aerogel that also includes flexible linkages as described herein is believed to simultaneously meet two distinct needs with respect to making aerogels more robust for commercial and industrial applications:

1. The conformal polymer coating imparts greater strength to the aerogels, making them strong enough to withstand mechanical loads they are likely to encounter during use; and
2. The flexible linkages impart greater flexibility, enabling the wet gels to be air dried without expensive and time-consuming supercritical $CO_2$ methodologies, as well as enabling the dried aerogels to withstand cyclic or opposing mechanical stresses or loads while lowering the risk of brittle fracture.

Certainly, aerogels incorporating both a polymeric conformal coating and flexible linkages as herein described have been shown to exhibit high mechanical strength and, simultaneously, substantial green strength prior to cross-linking as well as improved flexibility and a substantially reduced tendency for brittle failure after cross-linking, as the following examples demonstrate.

In a preferred embodiment, a ceramic oxide network as herein described (such as a silica network) includes both flexible linkages and a polymeric coating linked to surface-bound non-hydroxyl functional groups. In the case of a silica network, the co-hydrolysis of greater than 50 wt. % total a) functionalized silica precursor species (e.g. VTMS or APTES) and b) flexible linkage precursor species (e.g. BTMSH), with the balance being unfunctionalized silica precursor, wherein all weight percentages are based solely on the total silanes present, can produce dried aerogels that exhibit a significant degree of recovery following compressive strain. When the total of functionalized silica precursor species and flexible linkage precursor species is above 66% (based on total silanes), almost total recovery of compressive strain following compression has been observed for certain dried aerogels. Preferably, the ceramic-oxide network is prepared from 50-100 wt. % total functionalized precursor species and flexible-linkage precursor species, wherein the reaction mixture includes at least 10 wt. % (more preferably at least 12 wt. %, 14 wt. % or 16 wt. %) flexible-linkage precursor and at least 1 wt. % (more preferably at least 5 wt. % or 10 wt. %) functionalized ceramic-oxide precursor species. In case the total of flexible-linkage precursor species and ceramic-oxide precursor species do not sum to 100 wt. % of total silanes, the balance is unfunctionalized ceramic-oxide precursor species, which does not include moieties retained on the metallic/semi-metallic element following the network-synthesis reactions. Most preferably, the total of functionalized ceramic-oxide precursor species and flexible-linkage precursor species is at least 66 wt. %, balance (if any) unfunctionalized ceramic-oxide precursor species. In the case of a silica network, an exemplary embodiment includes 0-90 wt. % unfunctionalized silica precursor species (e.g. TMOS, TEOS), and 50-100 wt. %, more preferably 66-100 wt. %, total functionalized silica precursor species (e.g. APTES, VTMS) and flexible-linkage precursor (e.g. BTMSH, bis(trimethoxysilylpropyl)amine).

In the foregoing embodiments, a ceramic aerogel is imparted increased flexibility through the incorporation of flexible linkages intermediate the ceramic (e.g. silica) particles in the gel, while at the same time strength is improved by incorporating a polymer cross-linking architecture that is anchored to the ceramic (silica) particles at surface-bound reactive sites. In an alternative embodiment, flexibility also may be improved by utilizing a significant proportion of ceramic-oxide precursors having at least one species bound to the metallic/semi-metallic element in the precursor via a non-labile bond. For example, in the case of a silica aerogel, an alkyl(trialkoxy)silane, such as methyl-trimethoxysilane ($CH_3$—Si—$(OCH_3)_3$), abbreviated "MTMS," can be used as a major proportion, e.g. 50-100 wt. %, of the silica precursor species. As will be seen more fully in connection with Example 5 below, preparation of a silica aerogel based largely or entirely on MTMS as a silica precursor species produces aerogels having a very high degree of flexibility, even without the incorporation of a separate flex-link species as described in the embodiments above. Without wishing to be bound by a particular theory, it is believed that the non-labile S—$CH_3$ bond in MTMS results in a lesser silica density in the finished silica gel, because approximately 25% of the silicon valences in the gel are not available to form Si—O—Si bonds. The resulting less internally-bonded silica gel, having approximately 25% fewer internal linkages, is less tightly gel-polymerized compared to a conventional silica gel (e.g. one made using 100% tetra-alkoxy silanes such as TEOS or TMOS), making the resulting gel less brittle or rigid and more flexible. In essence, the unavailability of approximately 25% of Si valences in the finished gel to participate in gel-polymerization takes the place of the above-described flexible linkages to impart a degree of flexibility to the aerogel.

As also seen in Example 5 below, however, a silica aerogel produced exclusively from MTMS has very little stiffness or compressive strength. Even though such aerogels exhibit substantially 100% recovery following a compressive strain of up to 25% or more, the gels have practically no stiffness, and barely resist compression and are easily deflected. By incorporating a bi-silyl linking group into the silica aerogel backbone that is otherwise made by gel polymerization from MTMS, the resulting aerogel may have improved stiffness. The bi-silyl linking group can be a bi-silyl alkane, for example —Si—$C_{2-6}$—Si, wherein one or more of the intermediate carbon atoms can be substituted to add additional functional groups to impart desirable properties, or they can be unsubstituted. Alternatively, the bi-silyl linking group can be and in preferred embodiments is of the form $(RO)_3$—Si—$R^2$—Si—$(OR)_3$, in which R is an alkyl group, and $R^2$ can be a substituted and unsubstituted $C_{2-6}$ alkyl group, or $R^2$ can have the form —$R^3$—X—$R^3$—, wherein each $R^3$ is independently selected to be a substituted or unsubstituted $C_{2-6}$ alkyl group, and X is a functional group such as an amine, vinyl, thiols, acrylates and halides. As will be seen in Example 5 below, in preferred embodiments the bi-silyl linking group is bis(trimethoxysilyl)propylamine (BTMSPA), which is of the form $(RO)_3$—Si—$R^2$—Si—$(OR)_3$ wherein the R groups are methyls and the $R^2$ is $(CH_2)_3$—N—$(CH_2)_3$. This embodiment is preferred, for example, when it is desired to polymer-reinforce the silica aerogel via polyurethane chains, which can be linked to the secondary amines in the BTMSPA groups as described more fully in Example 5.

Using bis(trimethoxysilylpropyl)amine (BTMSPA) as the bi-silyl linking group, it has been discovered that highly stiff silica aerogels having substantially improved strength compared to the native MTMS-alone gels are produced that still recover substantially 95 to 100 percent, commonly greater than 96, 97 or even 98, percent, of their original pre-compression volume for strains even up to 25%. In addition to BTMSPA, the bi-silyl linking group in this embodiment may be other bi-silyl species, as well, for example other bi-silyl functional species wherein in place of an amine, the bi-silyl linking group incorporates a vinyl or other functional group. In a further alternative, the bi-silyl linking group may simply be a bi-silyl alkane, such as —Si—R—Si—, wherein R here is a saturated organic species. One such bi-silyl species is BTMSH, in which the R is a hexane group. Alternative to a straight alkane, the R group may also be a branched alkane, or an unsaturated or partially unsaturated alkyl group. As a further alternative, the R group may comprise a functional alkyl group, composed of a saturated or unsaturated, branched or straight, alkyl species, with one or more pendant functional groups.

As the data in Example 5 below demonstrate, a silica aerogel formed of MTMS and a bi-silyl linking group (BTMSPA in Example 5) exhibits a considerable increase in stiffness (modulus) as well as in strength (strength at break and toughness) compared to a native MTMS-only silica aerogel, while still maintaining the same or nearly the same degree of elastic recovery following 25% strain. However, even further increase in strength is achieved by reinforcing the silica aerogel with a polymer cross-linking architecture anchored to the aerogel backbone via functional groups on the bi-silyl linking group. In the case of BTMSPA as the bi-silyl linking group, for example, the secondary amine on this group provides a functional species that can form a urea bond with isocyanate. Using a polyisocyanate species, for example Desmondur N3300, which is a tri-isocyanate, a polyurethane cross-linking structure can be provided, wherein different tri-isocyanate molecules link to one another via urethane bonds between their respective isocyanate moieties, and the resulting chains are linked to the silica backbone via urea bonds with the secondary amines on the BTMSPA linking groups. The resulting structure has been found to exhibit even greater strength (strength at break, toughness) compared to MTMS-based silica aerogels incorporating bi-silyl linking groups alone, yet it still retains the same or a comparable degree of elasticity such that the polymer-reinforced aerogels exhibit greater than 95, 97 or 98 percent elastic recovery following a 25% strain.

When using BTMSPA as the linking group, alternative polymer cross-linking architectures may be employed, to produce polymer cross-linking chains that are anchored to the secondary amines in the BTMSPA linking groups. For example, polyepoxide molecules could be used in place of polyisocyanates, which would produce epoxy polymer chains anchored at the BTMSPA amines. In further alternatives, bi-silyl linking groups incorporating other functional species, such as vinyls, thiols, acrylates and halides could also be used, and the poly-functional prepolymer species used to produce the cross-linking chains tailored accordingly so they could be anchored to whatever functional species is selected for the bi-silyl linking groups. For example, a poly-styrene monomer may be used in the case where the bi-silyl linking groups include vinyl functionality.

Further aspects of the present invention will be illustrated and understood in the context of the following examples, which are provided by way of illustration and not limitation.

Example 1

Polystyrene Cross-Linked Aerogels with 1,6-Bis(trimethoxysilyl)hexane Flex-Link An experiment was performed to incorporate flexible linkages into a functionalized aerogel, wherein vinyl functionality was also incorporated at the secondary particle surfaces and used as an anchor to support polystyrene cross-linking of the aerogel. Thus, the resulting aerogel incorporated both flexible linkages and a polymer cross-linked conformal coating as described herein. Numerous samples were prepared to demonstrate the effect of varying the reactant concentrations on the resulting aerogel properties. To prepare the gels, first the following components were combined in a reaction mixture using ethanol as the solvent to carry out the network-synthesis reaction via hydrolysis and condensation:

tetramethoxysilane (TMOS), which is an unfunctionalized silica gel precursor species wherein all Si-bonds are hydrolysable;

1,6-bis(trimethoxysilyl)hexane (BTMSH) as the flexible linkage precursor, wherein the flexible linkage portion consists of a hexane chain linked at either end to silicon atoms whose other three valences are bound to methoxy groups via hydrolysable bonds; and vinyltrimethoxysilane (VTMS), which is a functionalized silica gel precursor species having vinyl functionality linked to the central Si atom via a non-hydrolysable bond, and three methoxy species also linked via hydrolysable bonds.

The structures of these reactants are provided below.

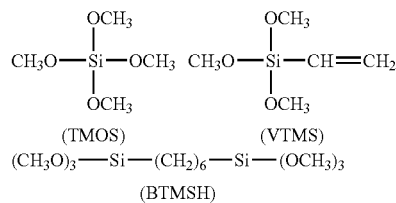

The total moles of silane (the sum of all three of the above components) were varied from 0.44 mol/l to 1.90 mol/l as shown in Table 1. The amount of VTMS was varied from 22.85 to 57.05 mol % of the total silane. The amount of BTMSH flex-link precursor was varied from 0 to 34.21 mol % of the total silane. The water:silane mole ratio ranged from 7.5 to 8.7 depending on the composition (water is the hydrolysis reactant). Ammonium hydroxide ($NH_4OH$) was used to catalyze the hydrolysis reactions and was kept constant at 1.00 ml for every 100 ml solution of the final mixture. For each sample, the silica gels were prepared by combining the three silane components with water and catalyst in the proportions listed below in table 1. In Table 1, only the mol percentages of BMTSH and VTMS are given, with the understanding that the balance of total silane in each sample is TMOS.

As a typical example, sample 21 from Table 1 was prepared from 1.37 mol/L of total silane, wherein the total silane included 32.83 mol % BTMSH, 38.30 mol % VTMS and balance TMOS. To prepare each sample, each of the silane components was provided from a solution of that component in methanol or ethanol, wherein the silane-source solutions were mixed in appropriate proportions to achieve the total moles silane and the silane concentrations reported in Table 1. The resulting mixed silane solution was cooled to below 0° C. in an acetone dried ice bath. A basic solution consisting of 1.00 ml $NH_4OH$, balance water was then added to each mixed silane solution so that each reaction mixture totaled 100 ml. The resulting reaction mixtures were thoroughly mixed together before being poured into 20-ml plastic syringe molds. Wet gel monoliths formed within 15 minutes to 1 day, and were aged for 24 hours. After aging, the gels were extracted into fresh MeOH or EtOH and allowed to rest for 24 hours. The gels were washed once more with fresh MeOH or EtOH and then solvent-exchanged to chlorobenzene in three wash steps.

The resulting wet gels, now in chlorobenene solution, were polymer cross-linked as follows. Styrene solution was prepared from a 50/50 wt % solution of styrene monomer in chlorobenzene. Final formulated molecular weight (MW), ranging from 1000 to 5000 g/mol, was controlled by the number of moles of polymerization initiator, 2,2'-Azobis(2-methylpropionitrile) (AIBN), that was introduced. All gels were soaked in the styrene mixture for 3 days, and then washed with fresh chlorobenzene, followed by heat treatment at about 70-75° C. for 24 hours. After heating, the gels were again washed with chlorobenzene twice before solvent exchanging with acetone. The cross-linked gels were then supercritically dried with liquid carbon dioxide ($CO_2$). Measured physical properties of each dried aerogel monolith are also provided in Table 1.

TABLE 1

Preparation conditions and some measured properties of the styrene cross-linked aerogel monoliths.

| Run No. | Total silane | BMTSH, mol % (based on total silane) | VTMS, mol % (based on total silane) | Styrene, FMW | Density, mg/cm$^3$, of dried aerogel | Porosity, %, of dried aerogel | Modulus, MPa, of dried aerogel | % non-recoverable strain of dried aerogel |
|---|---|---|---|---|---|---|---|---|
| 1 | 1.26 | 17.87 | 23.78 | 3000 | 326.84 | 76.78 | 17.54 | 9.5 |
| 2 | 0.95 | 31.55 | 52.58 | 5000 | 175.37 | 85.90 | 0.47 | 1.55 |
| 3 | 1.68 | 0 | 41.67 | 1000 | 329.93 | 76.64 | 20.35 | 10 |
| 4 | 1.61 | 0 | 24.9 | 5000 | 326.65 | 77.33 | 20 | 9.5 |
| 5 | 1.75 | 0 | 57.01 | 1000 | 277.47 | 79.83 | 12.62 | 9.3 |
| 7 | 0.84 | 17.85 | 23.83 | 5000 | 440.86 | 68.30 | * | * |
| 8 | 1.37 | 32.83 | 38.3 | 5000 | 232.25 | 82.32 | 3.29 | 0.45 |
| 9 | 1.37 | 32.83 | 38.3 | 5000 | 241.02 | 81.65 | 1.07 | 1.95 |
| 10 | 1.75 | 17.1 | 39.92 | 3000 | 284.4 | 78.36 | 10.68 | 8.15 |
| 11 | 0.95 | 31.55 | 52.58 | 3000 | 172.46 | 86.19 | 0.23 | 2.65 |
| 12 | 0.88 | 34.2 | 22.83 | 1000 | 149.72 | 88.66 | 0.34 | 14.7 |
| 13 | 0.88 | 34.2 | 22.83 | 1000 | 236.96 | 82.26 | 2.78 | 12.4 |

TABLE 1-continued

Preparation conditions and some measured properties of the styrene cross-linked aerogel monoliths.

| Run No. | Total silane | BMTSH, mol % (based on total silane) | VTMS, mol % (based on total silane) | Styrene, FMW | Density, mg/cm³, of dried aerogel | Porosity, %, of dried aerogel | Modulus, MPa, of dried aerogel | % non-recoverable strain of dried aerogel |
|---|---|---|---|---|---|---|---|---|
| 14 | 1.68 | 17.86 | 23.8 | 1000 | 369.62 | 70.58 | 32.43 | 11.1 |
| 15 | 1.75 | 34.21 | 22.8 | 3000 | 312.97 | 76.58 | 6.28 | 4.55 |
| 16 | 1.2 | 0 | 24.88 | 1000 | 315.55 | * | * | * |
| 17 | 1.75 | 34.21 | 22.8 | 5000 | 318.02 | 76.40 | 7.32 | 3.55 |
| 18 | 0.91 | 16.41 | 54.71 | 1000 | 121.99 | 90.34 | 0.17 | 0.99 |
| 19 | 1.83 | 16.41 | 54.71 | 5000 | 228.13 | 83.28 | 1.67 | * |
| 20 | 0.84 | 17.85 | 23.83 | 5000 | 308.89 | 77.89 | 18.04 | 6.7 |
| 21 | 1.37 | 32.83 | 38.3 | 1000 | 241.75 | 81.15 | 2.42 | 1 |
| 22 | 1.37 | 32.83 | 38.3 | 1000 | 249.67 | 80.92 | 0.87 | 1.3 |
| 24 | 1.61 | 0 | 24.9 | 5000 | 330.55 | * | * | * |
| 26 | 1.83 | 16.41 | 54.71 | 5000 | 237.3 | 82.16 | 1.75 | 1.5 |
| 29 | 1.32 | 0 | 57.03 | 3000 | 280.95 | 79.28 | * | * |
| 30 | 0.91 | 16.41 | 54.71 | 1000 | 124.64 | 90.33 | 0.2 | 8.4 |

* Not measured

Figure 6:
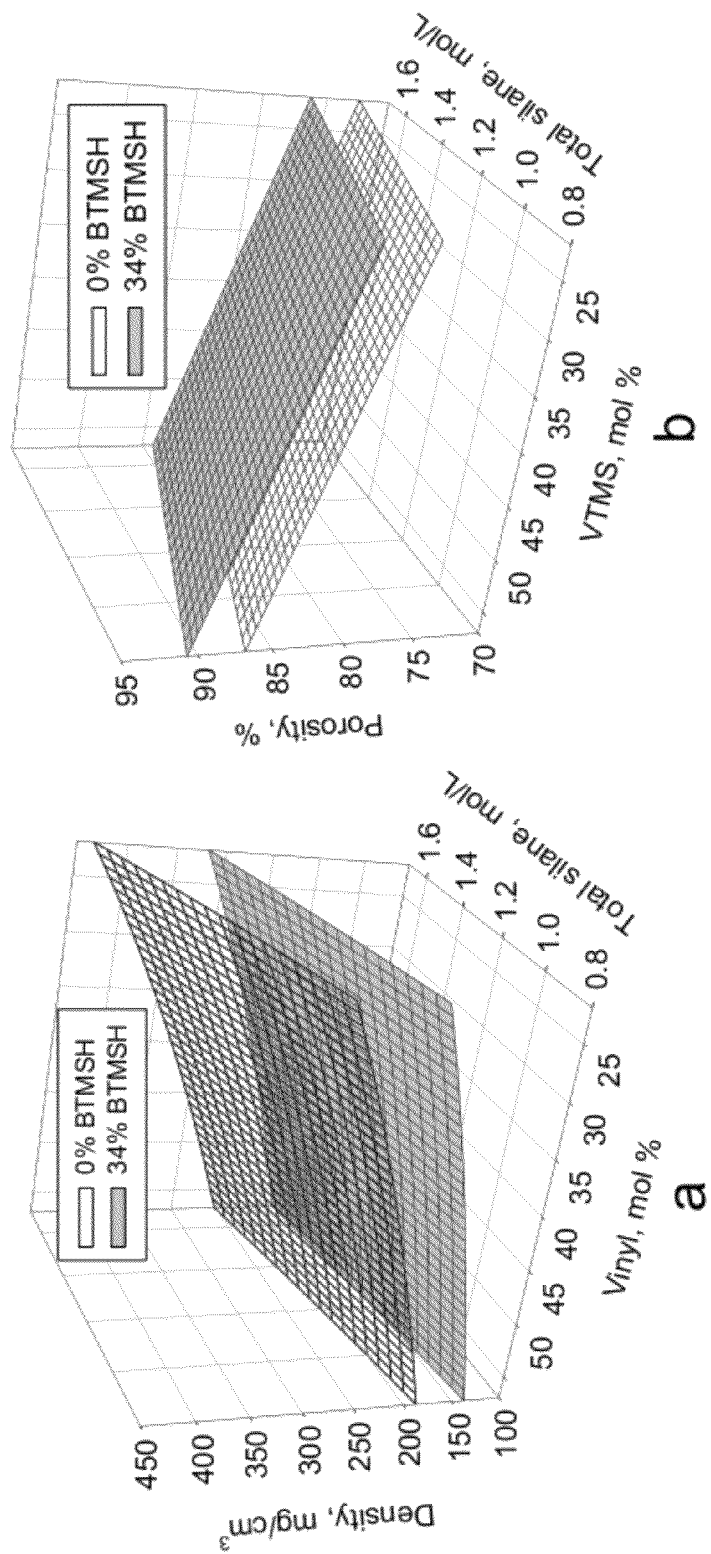
FIG. 6 consists of response surface models showing a) density and b) porosity of aerogel monoliths prepared in Example 1 graphed vs. VTMS and total silane concentration.

Data from Table 1 was analyzed using multiple linear regression analysis to create empirical models representing the relationships between the variables and the measured responses, with selected results shown in FIG. 6. In that figure, the clear response surfaces represent predicted density or porosity of aerogels incorporating 0% flex-links (bi-silyl-hexyl linkages), and the shaded response surfaces represent predicted density or porosity of aerogels incorporating 34% BTMSH flex-links. Plots of the resulting response surface models for density graphed vs. total silane and VTMS concentration are shown in FIG. 6a. Density of the monoliths increased with increasing total silane and VTMS, and decreased with increasing amounts of BTMSH. Increasing amounts of VTMS would tend to increase the amount of cross-linking while BTMSH would limit the amount of cross-linking. The porosity versus total silane and VTMS concentration data, shown in FIG. 6b, show that increasing amounts of total silane and VTMS reduced porosity, while porosity increased with increasing amounts of BTMSH. Also according to the model, styrene formulated molecular weight had no significant effect on density or porosity.

Figure 7:
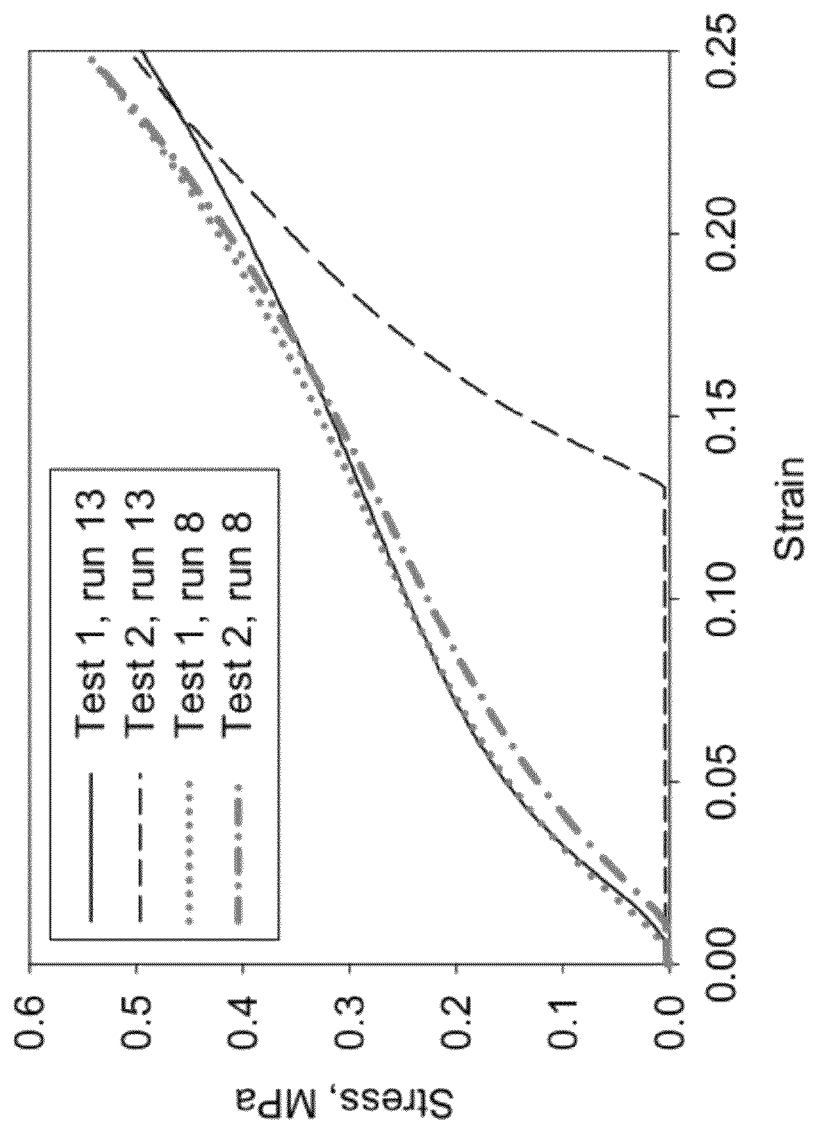
FIG. 7 shows compression curves for two separate aerogels, samples 13 and 8 respectively, from Example 1 that showed a similar modulus. Sample 13 only recovered halfway, while sample 8 showed almost complete recovery from compression.

As evident from Table 1, compression tests were carried out on the aerogel monoliths. In addition, the amount of unrecoverable compressive strain, a typical test for measuring flexibility of foams, was also measured on the monolith samples. In the typical compression-deflection test, a sample was compressed to 25% strain and released twice. After a fixed time (in this case 30 minutes), the length of the sample was measured. The value of unrecoverable compressive strain is given in Table 1 as the percent of the length that did not recover for each monolith. Stress-strain curves for compression for a couple of the runs from Table 1 having similar moduli are shown in FIG. 7. Note that the compression curves (black) from test 1 and test 2 for the monolith from run 13 show that around 12.4% of the strain was unrecoverable, while those from run 8 (red) almost perfectly overlapped showing almost all strain was recoverable up to 25%. Note also that since the compression tests were done in rapid succession, the stress-strain curves indicate that the recovery of sample after the first compression was almost instantaneous.

Figure 8:
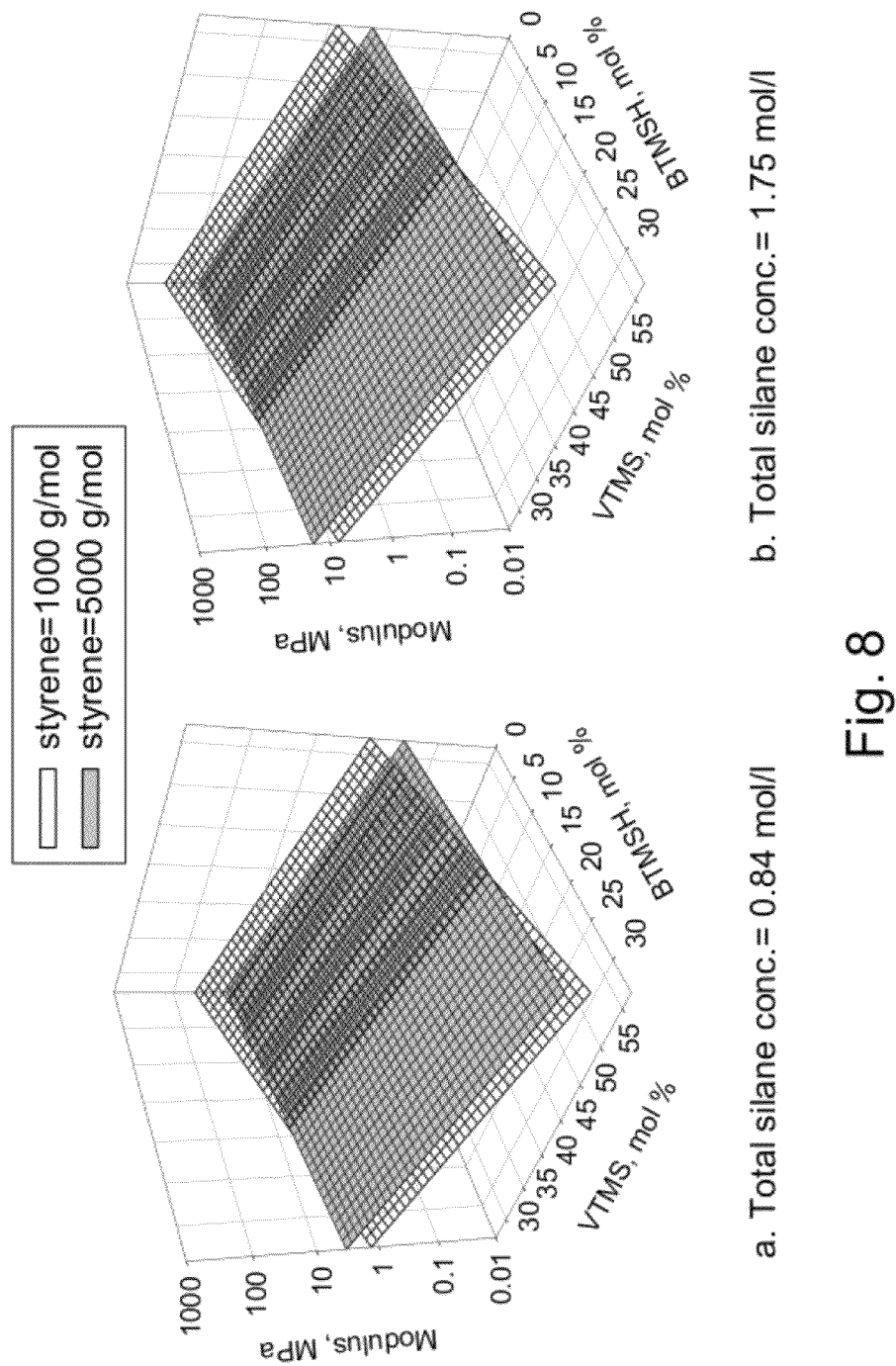
FIG. 8 shows fitted models of modulus from compression data of aerogel monoliths from Example 1 a) when total silane=0.84 mol/l and b) when total silane=1.75 g/mol graphed vs. VTMS and BTMSH fraction.

Data from compression tests were also modeled using multiple linear regression analysis. FIGS. 8a (total silane=0.84 mol/l) and 8b (total silane=1.75 mol/l) show the modulus from compression graphed vs. VTMS and BTMSH concentrations at different levels of styrene MW and total silane concentration. Modulus was significantly dependent on all four variables. Increasing total silane concentration caused an increase in modulus, while increasing VTMS and BTMSH concentration decreased modulus. There appeared to be a synergistic effect of BTMSH concentration and the styrene molecular weight. Increasing BTMSH concentration caused modulus to decrease much more when styrene MW was set to 1000 (clear surfaces), while at styrene MW set to 5000 (gray surfaces), the decrease in modulus from 0% to 34% BTMSH was much smaller.

Figure 9:
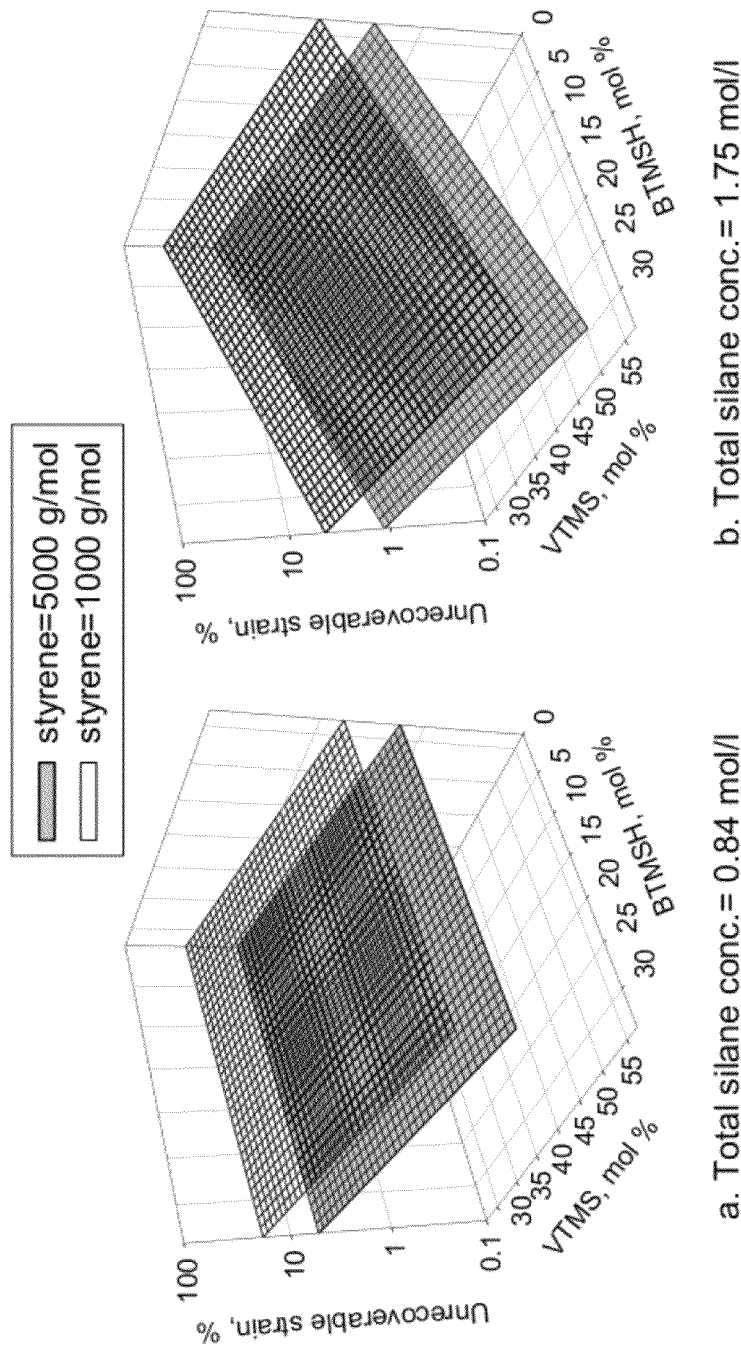
FIG. 9 shows fitted models of unrecoverable strain from compression-deflection tests of aerogel monoliths from Example 1 a) when total silane=0.84 mol/l and b) when total silane=1.75 g/mol graphed vs. VTMS and BTMSH fraction.

Graphs of response surface models for unrecoverable compressive strain are shown in FIGS. 9a (total silane=0.84 mol/l and 9b total silane=1.75 mol/l). Again, unrecoverable compressive strain was significantly dependent on all four variables. Unrecoverable compressive strain always decreased with increasing VTMS concentration and increasing styrene MW. When total silane concentration was low, unrecoverable compressive strain slightly decreased with increasing BTMSH concentration, while the effect was much more pronounced when total silane concentration was high. The lowest predicted values for unrecoverable compressive strain occurred with total silane at 1.84 mol/L, VTMS concentration (based on total silane) at 57 mol %, BTMSH concentration (based on total silane) is 34 mol % and styrene MW at 5000. Monoliths made using this combination of conditions should recover almost entirely after being compressed to 25% strain. Also evident from the graphs, it is not enough to use BTMSH in high concentrations to get almost full recovery. Rather, a combination of BTMSH and VTMS in at least 50 mol % of the total silane was needed when total silane and styrene FMW are at a high to get non-recoverable strain to 1% or less. At least 66 mol % was needed when total silane was at a low and styrene high. When both styrene FMW and total silane concentration were low, nonrecoverable strain was never lower than 5.5%.

Thus, the physical properties of the silica aerogel were varied based on varying the concentrations of the reactants for making the gel, (functionalized, unfunctionalized and flex-link precursor silane species) and correspondingly the degree of cross-linking and flex-linkage incorporation in the resulting aerogel.

Example 2

Air Dried Aerogels that Exhibit No or Negligible Shrinkage or Fracture

Figure 10:
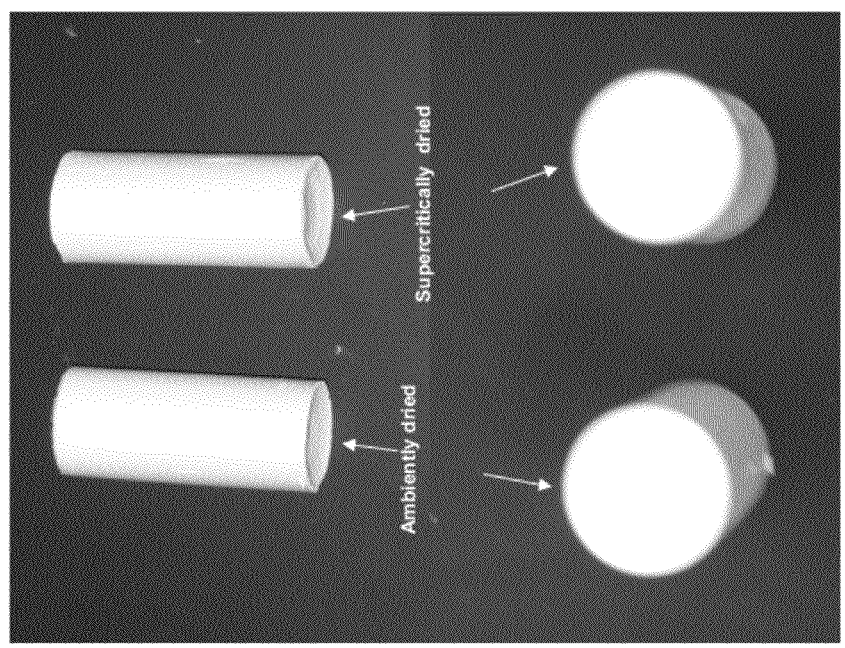
FIG. 10 is a photograph showing two silica aerogels having the same composition and incorporating flexible linkages as described in Example 2. One of the aerogel monoliths was dried in ambient air and the other via the conventional supercritical $CO_2$-mediated process. No appreciable shrinkage was observed in the air-dried sample.

Typically, conventional aerogels require supercritical fluid extraction of the solvent in order to maintain the gel's porous network in the final product. Ambiently dried gels ("xerogels") typically collapse and shrink, giving a much more dense material. However, it has been observed that by adding 30-50 mol % of a flex-link additive, gels can be air-dried at ambient pressure without observable shrinkage or fracture. Specifically, two monoliths were prepared similarly as in Example 1 above, wherein the total silane included 32.83 mol % BTMSH as the flex-link precursor, 36.3 mol % VTMS as the functionalized silica precursor and balance TMOS as the unfunctionalized silica precursor, in 1.37 mol/L total silane. One of the monoliths was dried using the conventional supercritical $CO_2$-mediated drying procedure, wherein the reaction solvent is exchanged with liquid $CO_2$, which is then converted directly into the supercritical state. The other monolith was allowed to dry in room air at atmospheric (ambient) pressure, with no special drying treatment. The two samples are shown in FIG. 10, wherein the sample on the left was ambiently dried and the sample on the right was dried via the supercritical $CO_2$ process. As can be clearly observed, both of the samples have similar size and density, indicating that no appreciable shrinkage occurred in the air-dried monolith.

Example 3

Di-isocyanate Cross-Linked Aerogels with 1,6-Bis(trimethoxysilyl)hexane as Flexible Link Use of a flex-link in the underlying silica gel backbone is also demonstrated using a combination of TMOS, BTMSH and APTES with a di-isocyanate monomer (Desmodur N3200) used to produce polymeric cross-linking from amine groups at the secondary-particle surfaces. The structures of the three silane species are reproduced below for convenience.

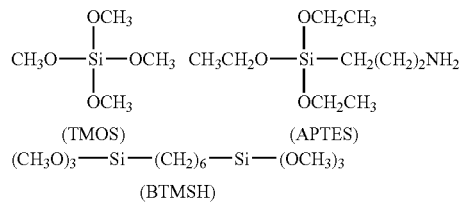

The total moles of silane (the sum of the above three components) were varied from 0.25 M to 0.75 M as shown in Table 2. The amount of APTES was held constant at 17.5 mol % while BTMSH was varied from 10 to 50 mol % of the total silane. The balance total silane in each sample was thus TMOS. The amount of di-isocyanate was varied from 10 to 30 w/w % of solution. The water:silane mole ratio was held constant at 7 for each reaction.

TABLE 2

Preparation conditions and some measured properties of the di-isocyanate cross-linked aerogel monoliths

| run | BTMSH, mol %, based on total silane | Total silane, mol/L | N3200 conc. w/w % | Bulk Density g/cc |
|---|---|---|---|---|
| 1 | 50 | 0.75 | 30 | 0.204 |
| 2 | 30 | 0.5 | 20 | 0.092 |
| 3 | 30 | 0.5 | 20 | 0.097 |
| 6 | 10 | 0.25 | 10 | 0.036 |
| 7 | 10 | 0.25 | 30 | 0.053 |
| 8 | 30 | 0.75 | 20 | 0.155 |
| 10 | 30 | 0.25 | 20 | 0.027 |
| 12 | 10 | 0.5 | 20 | 0.086 |
| 13 | 30 | 0.5 | 20 | 0.086 |
| 15 | 50 | 0.25 | 30 | 0.021 |
| 18 | 30 | 0.5 | 30 | 0.099 |
| 19 | 30 | 0.5 | 10 | 0.080 |

The silica gels were prepared by combining a solution of the three silane components with water. No additional catalyst was required as APTES provided sufficient base functionality to catalyze hydrolysis. To prepare the reaction mixture for each sample, the three silane components were combined according to the respective proportions for each sample in acetonitrile solvent and the mixed silane solution then was cooled to below 0° C. in an acetone dried ice bath. Water was then added to the cooled mixed silane solution to make up a total of 100 ml reaction mixture for each sample. The resulting mixtures were thoroughly mixed together before being poured into 20-ml plastic syringe molds. Wet gel monoliths formed within 15 to 30 minutes, and were aged for 24 hours. After aging, the gels were extracted into fresh AcN and allowed to rest for 24 hours. The gels were washed three more times with fresh AcN. The gels were then soaked in a 30 w/w % N3200 di-isocyanate for 24 hours, washed with fresh AcN, and heated at about 70° C. for 24 hours. After heating, the gels were washed with AcN three times before supercritical drying with carbon dioxide ($CO_2$).

Figure 11:
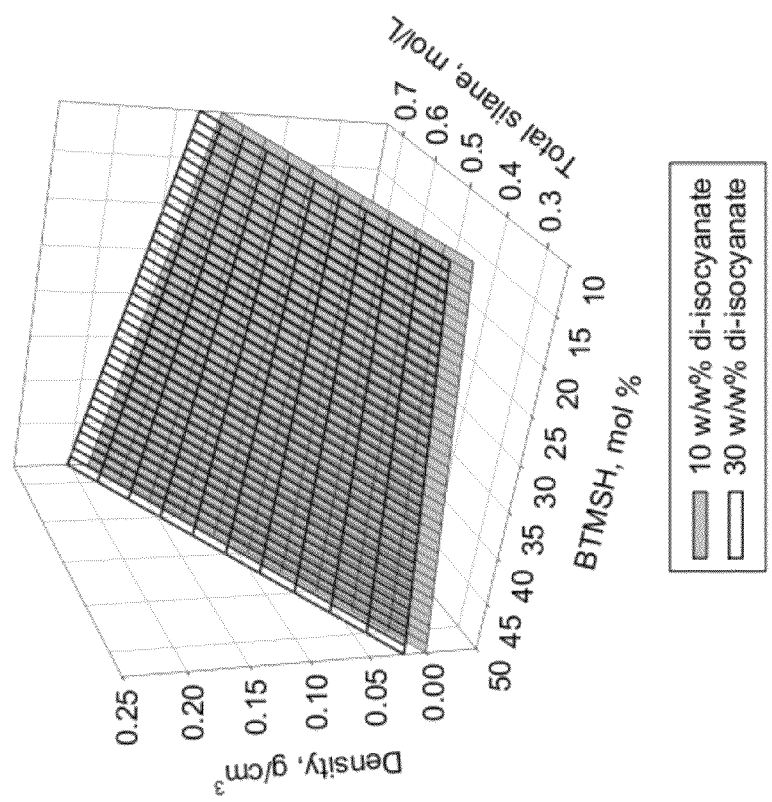
FIG. 11 is a graph of a response surface model for density vs. total silane and BTMSH concentration based on the aerogel samples made in Example 3.

Densities of each monolith were measured, and density data was modeled using multiple linear regression analysis. Plots of the resulting response surface models for density graphed vs. total silane and BTMSH concentration are shown in FIG. 11. As seen in the figure, density increased with increasing total silane and di-isocyanate concentration. Furthermore, when total silane concentration was low (0.25 mol/L), density decreased with increasing amounts of BTMSH, while at high total silane, density increased with increasing amounts of BTMSH.

Figure 12:
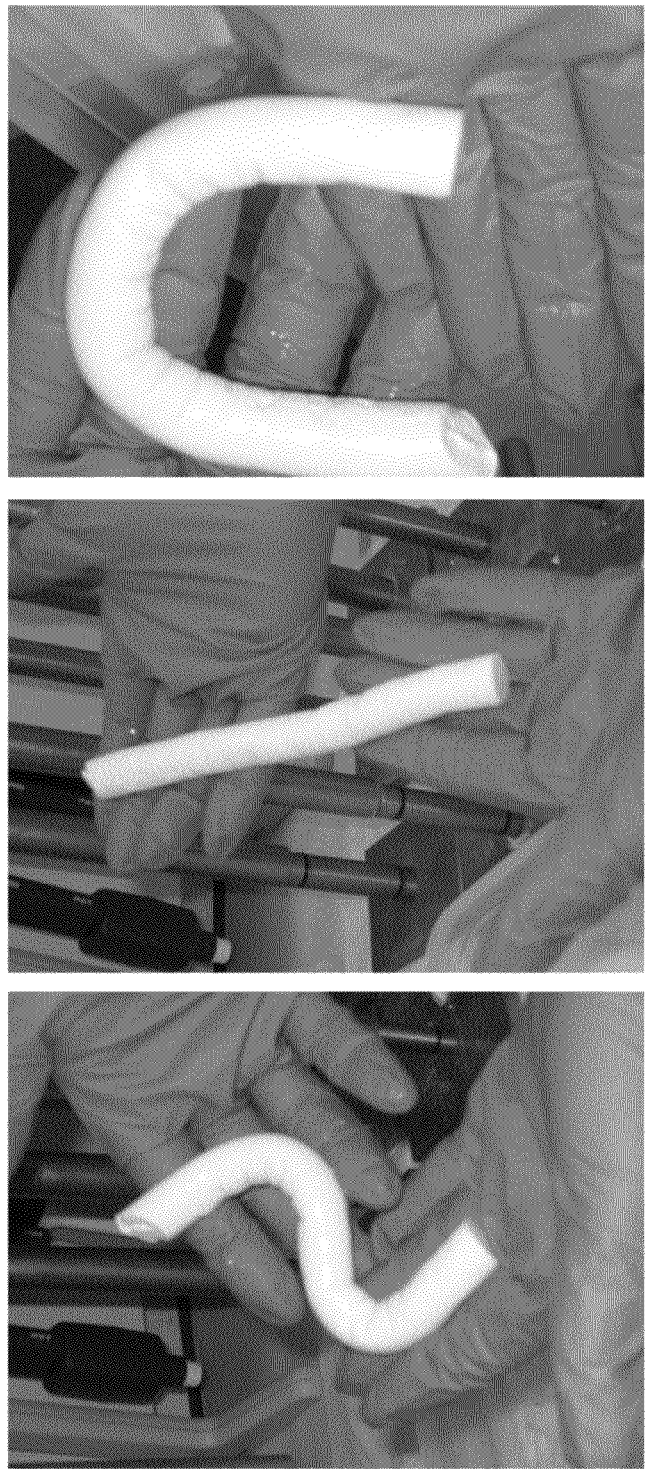
FIG. 12 shows photographs of silica wet gels prepared as described in Example 3, which exhibited a high degree of flexibility and could be manipulated by hand and bent into various conformations without breaking.

Though mechanical properties were not measured for the di-isocyanate cross-linked aerogels, handling the monoliths suggested that those containing high concentrations of the flex-link additive exhibit recoverable compression comparable to the styrene cross-linked aerogels described in Example 1 above. In addition, wet gels before cross-linking were easier to handle, resulting in less breakage on extraction from molds. FIG. 12 shows wet silica gels made from a formulation similar to run 8 in this Example, prior to drying. As can be clearly seen from the figure, the gels exhibited a surprising amount of flexibility and could be bent and manipulated into various conformations without breaking.

Example 4

Polyurethane Cross-Linked Aerogels with Bis-(trimethoxysilylpropyl)-amine as Flexible Linkage In this example, Bis(3-trimethoxysilylpropyl)amine, BTMSPA, was used as both underlying flex-link and amine reactive site. Table 3 shows results of different formulations of silica aerogels, cross-linked with N3300A. The structures of both BTMSPA and Desmondur N3300A are shown below.

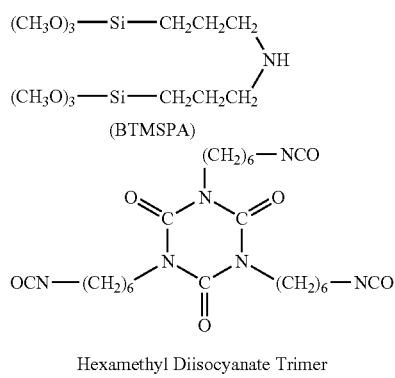

Hexamethyl Diisocyanate Trimer

For each sample in this Example, the appropriate mixture of BTMSPA and TMOS (if any) in acetonitrile (ACN) was prepared to produce the compositions referenced in Table 3, and cooled to below 0° C. in an acetone dried ice bath. Thereafter, water was added to effect hydrolysis and condensation. The contents were thoroughly mixed before being poured into molds. Gelation occurred within minutes, and wet gels were aged for 24 hours. Once extracted, the gels were washed in acetonitrile four times before the cross-linking reaction was carried out.

Incorporating the flex link itself improved the handle-ability of the uncross-linked gels before drying compared to gels with no flex-link. However, after supercritical drying, non-crosslinked gels tended to fall apart very easily. To cross-link the gels, they were soaked in a 30 w/w % solution of Desmodur N3300A, a trifunctional isocyanate, in acetonitrile for 24 hours, followed by heat treatment at 75° C. for 6 hours in fresh acetonitrile. The resulting cross-linked gels were washed 4 times with acetonitrile, and then supercritically dried with liquid $CO_2$. After drying, elastic modulus and compression data were measured for each monolith and values are reported in Table 3.

TABLE 3

Aerogel monoliths containing BTMSPA flex-link and cross-linked with N3300A.

| Exp. | Total Si, mol/L | TMOS, mol % | BTMSPA, mol % | Density, mg/cm3 | Modulus, MPa | Unrecoverable strain, % |
|---|---|---|---|---|---|---|
| A | 1.52 | 86.53 | 13.47 | 222.40 | 5.88 | 9.80 |
| B | 0.86 | 86.76 | 13.24 | 91.56 | 0.33 | 8.70 |
| C | 0.33 | 86.86 | 13.14 | 55.82 | 0.23 | 8.20 |
| D | 0.8 | 0.00 | 100 | 456.72 | 28.76 | 0.7 |
| E | 0.42 | 0.00 | 100 | 181.18 | 4.04 | 0.3 |

As can be seen from the data, aerogels prepared from 100 mol % BTMSPA, with no unfunctionalized silica gel precursor at all, produced aerogels with greater elastic recovery (lowest unrecoverable strain) compared to aerogels made with only 13 mol % BTMSPA.

Figure 13:
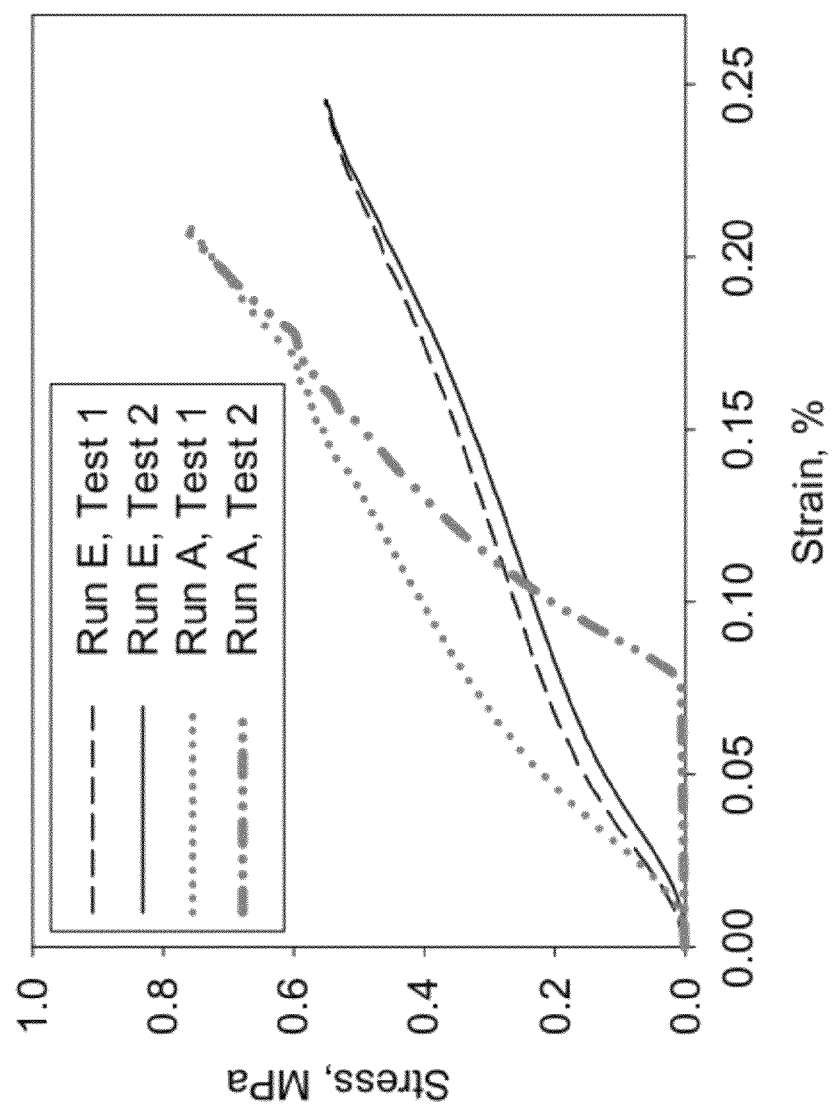
FIG. 13 shows compression curves for two separate aerogels, Runs A and E respectively, from Example 4 comparing the degree of recoverability between them based on their respective BTMSPA concentrations (~13% versus 100% of total silanes).

To illustrate, stress-strain curves for Run A (13.47% BTMSPA) and Run E (100% BTMSPA) are shown and compared in FIG. 13. Though Runs A and E had similar compressive moduli, Run A exhibited 9.8% unrecoverable strain while Run E nearly completely recovered when compressed to 25% strain. An optimization study using intermediate values of BTMSPA with TMOS and higher total silane may allow for optimized samples with similar recovery and higher modulus as seen in the previous Examples.

Example 5

Polyurethane Cross-Linked Aerogels Based on methyl tri-methoxy silane (MTMS) and Using bis-(trimethoxysilylpropyl)-amine as Flexible Linkage While polymer-reinforced aerogels exhibit a great improvement in strength over native silica aerogels, for many applications it is desirable to have a more flexible or elastic material with properties similar to that of a polymer foam. For example, insulation for extravehicular activity (EVA) suits should also be durable and flexible to accommodate as much freedom of movement for the astronaut as possible. A flexible form of polymer-reinforced aerogel would also be desirable for wrapping around structures that need to be insulated, such as cryotanks or cryogenic transfer lines. Yet another use for flexible durable aerogels could be as part of an inflatable decelerator used to slow spacecraft for planetary entry, descent and landing (EDL). EDL systems used to successfully land six robotic missions on Mars from 1976 to 2008 employed a hard aeroshell heat shield and parachutes of 12-16 m in diameter. Future robotic and manned missions will be much heavier and will require more drag for landing. Hence, new designs with much larger diameters (30-60 m) will be required. Inflatable decelerators would stow in a small space and deploy into a large area lightweight heat shield to survive reentry. Minimizing weight and thickness of the system as well as providing suitable insulation are important considerations.

Though some measure of flexibility is obtained in the polymer-reinforced aerogels through a decrease in density, it has been shown that more flexibility is obtained in unreinforced aerogels by altering the silica backbone in some significant way. For example, Kramer et al., *Mater. Res. Soc. Symp. Proc.* 1996, 435, 295-300, demonstrated that including up to 20% (w/w) poly(dimethylsiloxane) in tetraethoxyorthosilicate (TEOS)-based aerogels resulted in rubbery behavior with up to 30% recoverable compressive strain. More recently, Rao et al., *J. Colloid Interface Sci.* 2006, 300, 279-285, have shown that utilizing methyltrimethoxysilane (MTMS) as the silica precursor and a two-step synthesis imparts extraordinary flexibility to the aerogels. The MTMS-derived aerogels are more flexible largely because of the resulting lower cross-link density of the silica [three alkoxy groups that can react versus four in the more rigid tetra-alkoxysilane derived aerogels]. Kanamori et al., *Adv. Mater.* 2007, 19, 1589-1593; *J Sol-Gel Sci Technol*, 2008, 48, 172-181, using a surfactant to control the pore size and a slightly different process, showed that MTMS-derived gels can be made which demonstrate reversible deformation on compression. In fact, some formulations were able to be dried ambiently, which exerts similar forces on the gels. Initially, the gels shrink about 65% but spring back to nearly their original size, resulting in almost identical density and pore structure as those dried supercritically.

Though the MTMS derived aerogels are very flexible and elastic, it does not take much force to compress them. For example, Rao reports a Young's modulus of only 0.03 to 0.06 MPa for the flexible MTMS derived aerogels ranging in density from 0.04 to 0.1 $g/cm^3$. Kanamori does not report Young's modulus, but stress-strain curves indicate that stresses of less than 1 MPa are sufficient to compress samples with bulk densities around 0.2 $g/cm^3$ to 25% strain.

As discussed above, we have demonstrated improved compressive strength combined with elastic recovery after compression for silica aerogels reinforced with styrene, epoxy or di-isocyanate by replacing a large fraction of TMOS or TEOS with bis(trimethoxysilyl)hexane (BTMSH). The hexyl group from BTMSH provides a flexible link in the underlying silica giving similar elastic properties as seen in MTMS-derived aerogels. Polymer reinforcement is provided as previously described by incorporating reactive groups in the silica backbone and reacting with monomer. In this way, polymer-reinforced aerogels were made with compressive modulus as high as 10 MPa (100 times that of the MTMS gels) which still recovered almost completely from compression to 25% strain.

In this example, we demonstrate the effect of incorporating organic linking groups into the underlying silica structure and use of polymer reinforcement on MTMS-derived aerogels to preserve their unique spring back behavior while increasing the compressive strength. To this end, silica gels are prepared using MTMS and bis(trimethoxysilylpropyl)amine (BTMSPA) precursors in a one-step synthesis as shown in Scheme 1 immediately below, using acetonitrile or acetone as the solvent. The secondary amine from the BTMSPA serves as the base to catalyze condensation of the silanes. This means that when BTMSPA is used, no separate catalyst need be added to the gel polymerization reaction to generate the silica network. The BTMSPA also provides a site for reaction with polyisocyanate molecules, such as tri-isocyanate, to form a polyurea conformal coating on the silica structure. A statistical experimental design is employed to examine the effect of total concentration of silicon, mol % BTMSPA, solvent (acetone or acetonitrile), water/total silicon mol ratio (r), and the number of washes (to remove excess water and methanol by-product from the hydrogels) before reacting with a tri-isocyanate on the mechanical and physical properties of the aerogels. Properties of the polymer-reinforced aerogels are also compared to their non-reinforced counterparts.

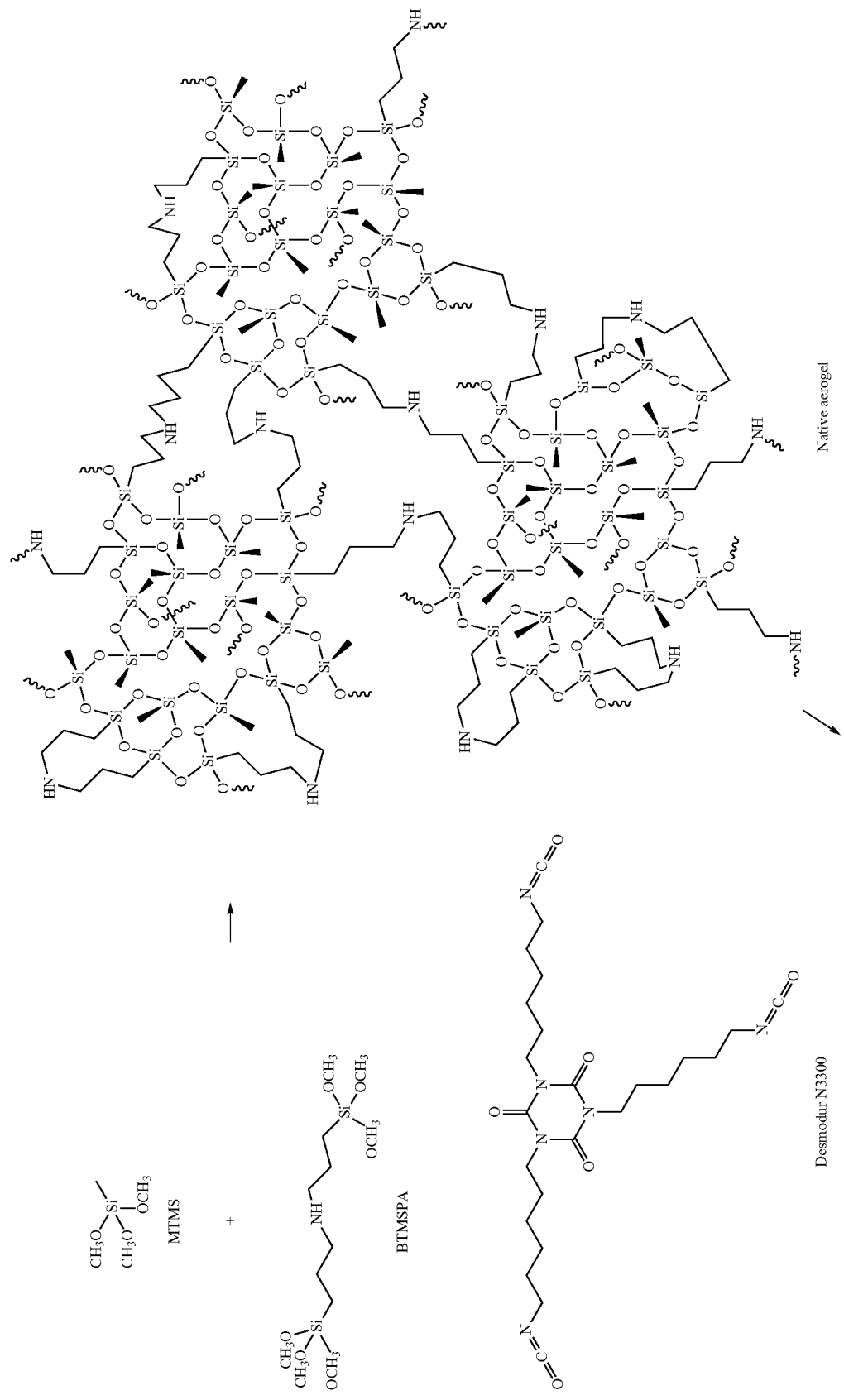
Scheme 1. Proposed molecular structure of aerogels from MTMS and BTMSPA and reinforced with tri-isocyanate Desmodur N3300.

-continued
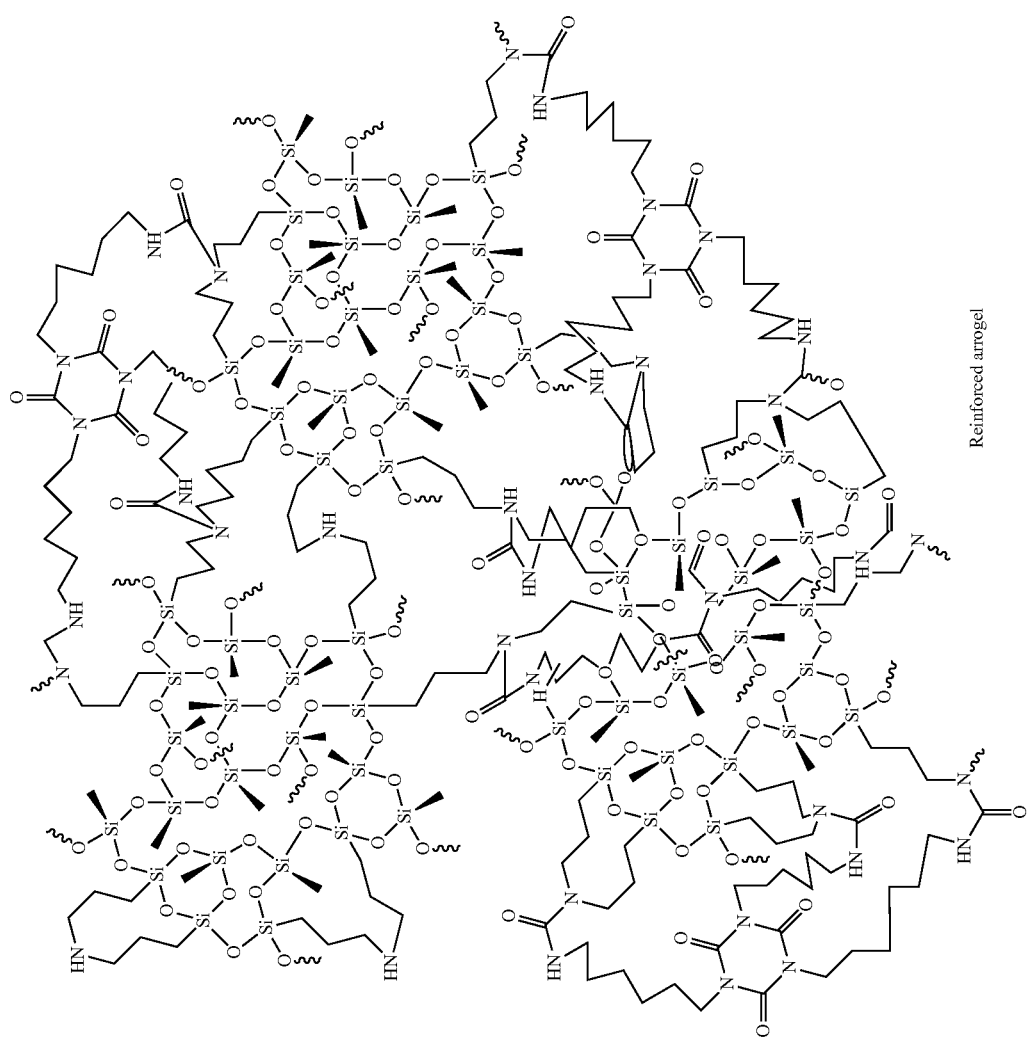
Reinforced arrogel

Methyltrimethoxysilane (MTMS) and bis(trimethoxysilylpropyl)amine (BTMSPA) were purchased from Gelest, Inc. Acetonitrile and acetone were obtained from Aldrich Chemical Company. Liquid carbon dioxide was purchased from Air Gas Great Lake. Desmodur N3300A was provided by Bayer Corporation. All reagents were used without further purification.

Variables examined in aerogel preparation are the concentration of total silicon (derived from MTMS and BTMSPA combined) in the total solution (M), mole fraction of silicon derived from BTMSPA (mol %), solvent used for gelation (acetonitrile or acetone), water/total silicon ratio (r), and the number of washes before the cross-linking reaction, as shown in Table 4 below. The silica gels were prepared using a one-step synthesis with BTMSPA acting as the base catalyst as well as a site for cross-linking with tri-isocyanate.

In a typical example, run 7 from Table 4 below was made using 1.65 mol/L of total silane, with 20 mol % silicon from MTMS and 80 mol % silicon from BTMSPA (noting that BTMSPA contributes two moles of silicon for every mole of silane). A solution of 4.70-mL (33 mmol) of MTMS and 21.70-mL (66 mmol) of BTMSPA in 58.75-mL of acetonitrile was cooled to below 0° C. using a dry-ice acetone bath. An amount of 14.85-mL (825 mmol) of $H_2O$ was then added to the silane solution (r=5), followed by thorough mixing before being poured into 20-mL plastic syringe molds. Gelation occurred within 15 minutes. The wet gels were aged for 24 h before being extracted into fresh acetonitrile and allowed to rest for another 24 h. The gels were then soaked in a 30% (w/w) solution of N3300A in acetonitrile for 24 h, followed by solvent exchange to fresh acetonitrile before being heated to 70° C. for 6 h. The polymer-reinforced gels were washed in fresh acetonitrile four times at 24 hour intervals before being dried using supercritical carbon dioxide ($CO_2$) extraction.

The corresponding non-reinforced aerogels listed in Table 5 below were prepared the same way, except that soaking in tri-isocyanate and heat treatment steps were eliminated. Similar procedures were used when acetonitrile was replaced with acetone.

TABLE 4

Preparation conditions and measured properties for polymer-reinforced aerogels.

| Run# | Total Si, M | MTMS, mol % | BTMSPA, mol % | Water: Silane | # of Washes | Solvent | NCO:NH ratio | Bulk Density, g/cm³ | Porosity, % |
|---|---|---|---|---|---|---|---|---|---|
| 1  | 0.75 | 60 | 40 | 2.0 | 1 | acetonitrile | 0.03 | 0.058 | 95.9 |
| 2  | 1.20 | 40 | 60 | 3.5 | 2 | acetonitrile | 0.71 | 0.163 | 87.9 |
| 3  | 1.20 | 40 | 60 | 3.5 | 3 | acetonitrile | 0.71 | 0.160 | 88.5 |
| 4  | 1.65 | 20 | 80 | 5.0 | 3 | acetonitrile | 1.02 | 0.369 | 72.1 |
| 5  | 0.75 | 20 | 80 | 5.0 | 3 | acetonitrile | 0.58 | 0.101 | 92.6 |
| 6  | 1.65 | 60 | 40 | 2.0 | 1 | acetonitrile | 0.72 | 0.187 | 85.8 |
| 7  | 1.65 | 20 | 80 | 5.0 | 1 | acetonitrile | 1.22 | 0.385 | 70.6 |
| 8  | 1.20 | 40 | 60 | 5.0 | 2 | acetonitrile | 0.82 | 0.167 | 87.8 |
| 9  | 1.20 | 40 | 60 | 3.5 | 1 | acetonitrile | 0.94 | 0.163 | 90.2 |
| 10 | 1.20 | 40 | 60 | 2.0 | 2 | acetonitrile | 0.95 | 0.157 | 89.6 |
| 11 | 0.75 | 40 | 60 | 3.5 | 2 | acetonitrile | 0.05 | 0.072 | 95.4 |
| 12 | 1.20 | 40 | 60 | 3.5 | 2 | acetonitrile | 0.94 | 0.164 | 87.8 |
| 13 | 1.20 | 20 | 80 | 3.5 | 2 | acetonitrile | 1.01 | 0.216 | 84.2 |
| 14 | 1.20 | 40 | 60 | 3.5 | 2 | acetonitrile | 0.77 | 0.157 | 88.5 |
| 15 | 1.20 | 40 | 60 | 3.5 | 2 | acetonitrile | 0.88 | 0.159 | 88.1 |
| 16 | 0.75 | 20 | 80 | 2.0 | 1 | acetonitrile | 0.39 | 0.102 | 92.7 |
| 17 | 1.20 | 40 | 60 | 3.5 | 2 | acetonitrile | 0.69 | 0.160 | 88.5 |
| 18 | 1.20 | 40 | 60 | 3.5 | 2 | acetonitrile | 0.89 | 0.219 | 83.6 |
| 19 | 0.75 | 60 | 40 | 5.0 | 3 | acetonitrile | 0.01 | 0.053 | 96.9 |
| 20 | 1.65 | 20 | 80 | 2.0 | 1 | acetonitrile | 1.03 | 0.356 | 72.9 |
| 21 | 0.75 | 60 | 40 | 5.0 | 1 | acetonitrile | 0.01 | 0.049 | 97.0 |
| 22 | 0.75 | 20 | 80 | 5.0 | 1 | acetonitrile | 0.50 | 0.105 | 92.6 |
| 23 | 1.65 | 60 | 40 | 5.0 | 3 | acetonitrile | 0.74 | 0.185 | 86.3 |
| 24 | 0.75 | 20 | 80 | 2.0 | 3 | acetonitrile | 0.46 | 0.100 | 92.5 |
| 25 | 1.20 | 60 | 40 | 3.5 | 2 | acetonitrile | 0.45 | 0.111 | 92.2 |
| 26 | 1.65 | 60 | 40 | 5.0 | 1 | acetonitrile | 1.02 | 0.185 | 86.7 |
| 27 | 1.65 | 20 | 80 | 2.0 | 3 | acetonitrile | 1.04 | 0.353 | 73.2 |
| 28 | 1.65 | 60 | 40 | 2.0 | 3 | acetonitrile | 0.87 | 0.189 | 85.8 |
| 29 | 0.75 | 60 | 40 | 2.0 | 3 | acetonitrile | 0.17 | 0.056 | 96.4 |
| 30 | 1.65 | 40 | 60 | 3.5 | 2 | acetonitrile | 1.05 | 0.275 | 79.1 |
| 31 | 0.75 | 60 | 40 | 2.0 | 1 | acetone | 0.44 | 0.066 | 95.5 |
| 32 | 1.65 | 20 | 80 | 5.0 | 1 | acetone | 1.60 | 0.482 | 69.2 |
| 33 | 0.75 | 40 | 60 | 3.5 | 2 | acetone | 0.75 | 0.109 | 93.0 |
| 34 | 1.20 | 40 | 60 | 3.5 | 2 | acetone | 1.13 | 0.184 | 87.2 |
| 35 | 1.20 | 40 | 60 | 3.5 | 2 | acetone | 1.13 | 0.189 | 86.8 |
| 36 | 0.75 | 20 | 80 | 2.0 | 1 | acetone | 1.17 | 0.138 | 90.2 |
| 37 | 0.75 | 60 | 40 | 5.0 | 1 | acetone | 0.26 | 0.066 | 96.0 |
| 38 | 0.75 | 20 | 80 | 2.0 | 3 | acetone | 0.99 | 0.130 | 90.8 |
| 39 | 1.65 | 60 | 40 | 5.0 | 1 | acetone | 2.14 | 0.327 | 75.6 |
| 40 | 0.75 | 60 | 40 | 2.0 | 3 | acetone | 0.62 | 0.073 | 95.8 |

| Run# | Shrinkage, % | BET Srurface Area, m²/g | Modulus, MPa | Max. Stress at Break, MPa | Toughness, kJ/m³ | Unrecovered strain, % |
|---|---|---|---|---|---|---|
| 1 | 4.0  | a     | 0.00  | 2.76E−3 | 0.4  | 1.6 |
| 2 | 2.0  | 230.5 | 2.60  | 3.8     | 582  | 1.0 |
| 3 | 2.0  | 237.6 | 2.69  | 4.1     | 631  | 1.1 |
| 4 | 10.2 | 260.0 | 72.36 | 36.7    | 6488 | 2.1 |
| 5 | 3.1  | 139.1 | 0.60  | 0.3     | 47   | 0.7 |

TABLE 4-continued

Preparation conditions and measured properties for polymer-reinforced aerogels.

| | | | | | | | |
|---|---|---|---|---|---|---|---|
| | 6 | 1.2 | 292.3 | 2.94 | 4.3 | 662 | 3.2 |
| | 7 | 9.6 | 233.5 | 84.25 | 39.7 | 6944 | 3.0 |
| | 8 | 2.1 | 204.9 | 3.51 | 3.4 | 524 | 1.1 |
| | 9 | 2.1 | 203.9 | 3.12 | 2.6 | 437 | 0.7 |
| | 10 | 1.7 | 234.1 | 2.26 | 3.7 | 556 | 0.5 |
| | 11 | 2.0 | 18.1 | 0.02 | 0.0 | 5.1 | 1.1 |
| | 12 | 1.6 | 233.6 | 2.48 | 3.1 | 477 | 1.8 |
| | 13 | 4.9 | 248.1 | 10.55 | 12.3 | 1893 | 1.1 |
| | 14 | 1.8 | 231.6 | 2.74 | 2.9 | 448 | 1.3 |
| | 15 | 1.5 | 224.6 | 2.68 | 3.4 | 2085 | 0.7 |
| | 16 | 2.4 | 93.2 | 0.32 | 0.9 | 115 | 0.7 |
| | 17 | 2.2 | 229.1 | 2.38 | 2.8 | 383 | 0.7 |
| | 18 | 1.6 | 217.9 | 2.77 | 4.6 | 687 | 1.3 |
| | 19 | 2.8 | a | 0.01 | 9.7E−3 | 2.2 | 0.0 |
| | 20 | 8.9 | 266.1 | 49.98 | 41.9 | 6988 | 2.2 |
| | 21 | 1.9 | 7.4 | 0.01 | 1.0E−3 | 1.9 | 0.0 |
| | 22 | 2.3 | 126.2 | 0.50 | 0.4 | 71 | 0.6 |
| | 23 | 1.3 | 275.6 | 2.65 | 2.8 | 426 | 2.6 |
| | 24 | 1.8 | 102.9 | 0.31 | 1.0 | 105 | 2.0 |
| | 25 | 0.4 | 158.7 | 0.29 | 0.5 | 64 | 1.1 |
| | 26 | 1.2 | 246.8 | 2.48 | 3.2 | 488 | 3.5 |
| | 27 | 8.3 | 288.7 | 51.91 | 44.8 | 6405 | 2.1 |
| | 28 | 0.9 | 301.5 | 3.11 | 4.6 | 692 | 1.9 |
| | 29 | 3.8 | a | 0.00 | 4.8E−3 | 0.8 | 3.8 |
| | 30 | 4.8 | 242.2 | 17.65 | 23.2 | 3641 | 1.2 |
| | 31 | 5.3 | 76.9 | 0.01 | 0.06 | 15 | 0.79 |
| | 32 | 11.7 | 215.1 | 157.59 | 71.00 | 13082 | 0.56 |
| | 33 | 4.7 | 256.8 | 0.22 | 1.65 | 218 | 0.44 |
| | 34 | 4.6 | 283.7 | 3.60 | 8.54 | 1117 | 0.36 |
| | 35 | 5.6 | 297.0 | 3.44 | 6.86 | 1091 | 0.79 |
| | 36 | 5.4 | 275.8 | 1.00 | 1.01 | 351 | 0.33 |
| | 37 | 4.0 | 119.6 | 0.02 | 0.07 | 10 | 1.20 |
| | 38 | 5.2 | 253.3 | 0.76 | 3.04 | 363 | 0.74 |
| | 39 | 6.4 | 210.7 | 29.24 | 0.03 | 347 | 0.92 |
| | 40 | 5.2 | 147.3 | 0.03 | 0.2 | 36 | 0.36 | a Samples collapsed under vacuum. No data was collected.

TABLE 5

Preparation conditions and measured properties for non-reinforced aerogels.

| Run# | Total Si, M | MTMS, mol % | BTMSPA, mol % | Water: Silane | Solvent | Bulk Density, g/cm³ | Porosity, % | Shrinkage, % | BET Sruface Area m²/g | Modulus, MPa | Max. Stress at Break, MPa | Toughness, kJ/m³ | Unrecovered strain, % |
|---|---|---|---|---|---|---|---|---|---|---|---|---|---|
| 1 | 0.75 | 60 | 40 | 2.0 | acetonitrile | 0.055 | 96.3 | 5.1 | a | a | a | a | a |
| 2 | 1.20 | 40 | 60 | 3.5 | acetonitrile | 0.126 | 90.9 | 4.0 | b | 1.94 | 0.93 | 153 | 0.5 |
| 3 | 1.20 | 40 | 60 | 3.5 | acetonitrile | 0.124 | 91.9 | 3.2 | 394.9 | 1.93 | 0.75 | 115 | 1.1 |
| 4 | 1.65 | 20 | 80 | 5.0 | acetonitrile | 0.242 | 82.0 | 11.7 | 531.2 | 48.78 | 5.61 | 775 | NA |
| 5 | 0.75 | 20 | 80 | 5.0 | acetonitrile | 0.085 | 93.8 | 4.0 | 215.2 | 0.48 | 0.25 | 39 | 2.3 |
| 6 | 1.65 | 60 | 40 | 2.0 | acetonitrile | 0.147 | 89.0 | 3.0 | b | 2.87 | 0.46 | 50 | NA |
| 7 | 1.65 | 20 | 80 | 5.0 | acetonitrile | 0.234 | 82.6 | 10.1 | 521.0 | 38.05 | 5.39 | 745 | 0.9 |
| 8 | 1.20 | 40 | 60 | 5.0 | acetonitrile | 0.124 | 90.8 | 2.2 | 521.0 | 1.78 | 0.82 | 132 | 0.08 |
| 9 | 1.20 | 40 | 60 | 3.5 | acetonitrile | 0.124 | 90.7 | 4.0 | 531.2 | 1.44 | 0.96 | 160 | 0.44 |
| 10 | 1.20 | 40 | 60 | 2.0 | acetonitrile | 0.131 | 90.2 | 5.1 | 385.1 | 2.13 | 0.95 | 152 | 0.2 |
| 11 | 0.75 | 40 | 60 | 3.5 | acetonitrile | 0.067 | 95.1 | 0.6 | 215.4 | a | a | a | a |
| 12 | 1.20 | 40 | 60 | 3.5 | acetonitrile | 0.125 | 90.7 | 3.2 | 387.7 | 2.11 | 0.35 | 40 | NA |
| 13 | 1.20 | 20 | 80 | 3.5 | acetonitrile | 0.153 | 88.0 | 6.1 | 477.3 | 7.18 | 2.44 | 422 | 0.8 |
| 14 | 1.20 | 40 | 60 | 3.5 | acetonitrile | 0.127 | 90.6 | 4.3 | 371.1 | 2.11 | 0.54 | 76 | 1.2 |
| 15 | 1.20 | 40 | 60 | 3.5 | acetonitrile | 0.128 | 90.6 | 3.7 | 393.8 | 2.34 | 0.87 | 148 | 1.5 |
| 16 | 0.75 | 20 | 80 | 2.0 | acetonitrile | 0.087 | 94.0 | 5.3 | 134.7 | 0.11 | 0.13 | 21 | 0.85 |
| 17 | 1.20 | 40 | 60 | 3.5 | acetonitrile | 0.124 | 90.7 | 3.5 | b | 2.13 | 1.06 | 175 | 1.1 |
| 18 | 1.20 | 40 | 60 | 3.5 | acetonitrile | 0.130 | 69.7 | 4.4 | 392.6 | 2.21 | 0.90 | 144 | 0.2 |
| 19 | 0.75 | 60 | 40 | 5.0 | acetonitrile | 0.052 | 96.7 | 5.3 | a | a | a | a | a |
| 20 | 1.65 | 20 | 80 | 2.0 | acetonitrile | 0.256 | 81.0 | 13.3 | 499.8 | 45.66 | 2.33 | 322 | NA |
| 21 | 0.75 | 60 | 40 | 5.0 | acetonitrile | 0.054 | 96.4 | 4.5 | a | a | a | a | a |
| 22 | 0.75 | 20 | 80 | 5.0 | acetonitrile | 0.086 | 94.1 | 3.9 | b | 0.45 | 0.26 | 43 | 1.0 |
| 23 | 1.65 | 60 | 40 | 5.0 | acetonitrile | 0.159 | 88.5 | 3.3 | b | 1.92 | 1.13 | 173 | 0.52 |
| 24 | 0.75 | 20 | 80 | 2.0 | acetonitrile | 0.093 | 93.1 | 5.1 | 122.2 | 0.31 | 0.48 | 73 | 0.1 |
| 25 | 1.20 | 60 | 40 | 3.5 | acetonitrile | 0.104 | 92.1 | 2.3 | b | 0.31 | 0.19 | 28 | 0.4 |
| 26 | 1.65 | 60 | 40 | 5.0 | acetonitrile | 0.155 | 88.4 | 3.8 | 412.5 | 2.14 | 0.99 | 148 | 0.6 |
| 27 | 1.65 | 20 | 80 | 2.0 | acetonitrile | 0.265 | 80.4 | 13.2 | b | 39.38 | 7.08 | 1171 | 1.4 |
| 28 | 1.65 | 60 | 40 | 2.0 | acetonitrile | 0.168 | 74.5 | 4.5 | 402.7 | 2.67 | 4.48 | 725 | 0.6 |
| 29 | 0.75 | 60 | 40 | 2.0 | acetonitrile | 0.055 | 96.3 | 5.1 | a | a | a | a | a |

TABLE 5-continued

Preparation conditions and measured properties for non-reinforced aerogels.

| Run# | Total Si, M | MTMS, mol % | BTMSPA, mol % | Water: Silane | Solvent | Bulk Density, g/cm$^3$ | Porosity, % | Shrinkage, % | BET Sruface Area m$^2$/g | Modulus, MPa | Max. Stress at Break, MPa | Toughness, kJ/m$^3$ | Unrecovered strain, % |
|---|---|---|---|---|---|---|---|---|---|---|---|---|---|
| 30 | 1.65 | 40 | 60 | 3.5 | acetonitrile | 0.214 | 84.6 | 7.9 | b | 12.08 | 6.53 | 1126 | 1.3 |
| 31 | 0.75 | 60 | 40 | 2.0 | acetone | 0.061 | 96.45 | 9.2 | 179.9 | 0.02 | 0.10 | 9 | 0.00 |
| 32 | 1.65 | 20 | 80 | 5.0 | acetone | 0.287 | 80.34 | 14.7 | 589.6 | 41.23 | 12.72 | 2270 | 4.08 |
| 33 | 0.75 | 40 | 60 | 3.5 | acetone | 0.093 | 94.15 | 7.7 | 374.8 | 0.20 | 0.22 | 36 | 0.00 |
| 34 | 1.20 | 40 | 60 | 3.5 | acetone | 0.133 | 91.37 | 6.8 | 507.7 | 1.89 | 0.51 | 106 | 2.27 |
| 35 | 1.20 | 40 | 60 | 3.5 | acetone | 0.145 | 90.44 | 9.0 | 523.6 | 2.19 | 1.58 | 161 | 3.30 |
| 36 | 0.75 | 20 | 80 | 2.0 | acetone | 0.113 | 92.13 | 11.0 | 390.2 | 0.51 | 0.9 | 144 | 2.99 |
| 37 | 0.75 | 60 | 40 | 5.0 | acetone | 0.060 | 96.63 | 7.9 | 145.8 | a | a | a | a |
| 38 | 0.75 | 20 | 80 | 2.0 | acetone | 0.107 | 93.19 | 10.6 | 386.3 | 0.46 | 0.86 | 133 | 6.48 |
| 39 | 1.65 | 60 | 40 | 5.0 | acetone | 0.182 | 88.10 | 7.5 | 563.0 | 3.84 | 2.08 | 344 | 1.65 |
| 40 | 0.75 | 60 | 40 | 2.0 | acetone | 0.060 | 96.75 | 7.3 | 289.6 | a | a | a | a | a Aerogels were not tested due their softness and/or fragility
b No samples available for testing.

The skeletal density ($\rho_s$) was measured using an Accupyc 1340 helium pycnometer. Nitrogen sorption measurements using Brunauer-Emmett-Teller (BET) method were performed on a Micromeritics ASAP2020 chemisorption system. All samples were out-gassed at 80° C. for 12 h under a vacuum before analysis. Samples for microscopy were coated with gold/palladium and viewed using a Hitachi S-4700-11 field emission scanning electron microscope. Supercritical $CO_2$ fluid extraction was performed using an Applied Separations 1-Spe-ed SFE-2 manual system. Mechanical tests were done on an Instron 4505 eletromechanical machine using Testworks 4 software and a 10000 Newton load cell at 0.25 in/min. Solid $^{13}$C and $^{29}$Si NMR spectra were obtained on a Bruker Avance-300 spectrometer with a 4-mm solids probe using cross polarization and magic angle spinning at 11 kHz. The $^{13}$C NMR spectra were externally referenced to the carbonyl of glycine, which appears at 176.01 ppm, and the $^{29}$Si NMR spectra were externally referenced to the Si of 3-trimethoxysilylpropionic acid, which is at 0 ppm.

The bulk density ($\rho_b$) was determined by measuring the weight and volume of the sample. Dimensional change, or shrinkage (%), is taken as the difference between the diameters of the aerogel monolith and of the 20-mL syringe mold (nominally 20 mm). The skeletal density from helium pycnometry ($\rho_s$) and the bulk density were used to calculate the porosity (%) of the aerogels using Eq. 11.

$$\text{Porosity \%} = \frac{1/\rho_b - 1/\rho_s}{1/\rho_b} \times 100 \quad (11)$$

Compression tests were carried out on the aerogel monoliths in two steps. First, the aerogels were compressed to 25% strain. The test was stopped, the crosshead was instantly moved back to zero, and the procedure was repeated once more and released. The specimen was then left to sit for 30 min at room temperature. At that time, the final thickness was measured and the unrecovered strain (%) was determined as the amount of strain still present in the sample relative to the sample's initial length. The modulus was taken as the initial slope from the stress-strain curve of the first compression.

Experimental design and analysis was conducted using Design Expert 7.1.3 available from Stat-Ease, Inc. Using a d-optimal design to minimize the number of experiments, a total of 40 distinct batches of the aerogel monoliths, including 5 repeats of one formulation (#2, 12, 14, 15, and 18) were prepared by varying the total silicon concentration (0.75-1.65 mol/L), the fraction of silicon derived from BTMSPA (40-80 Si mol %), water/silicon ratio (r=2-5), the solvent (acetone or acetonitrile) and the number of washes (1-3) before the cross-linking reaction. Silicon concentration and silicon mole percent were used instead of silane concentration because every mole of BTMSPA contributes 2 moles of silicon, while one mole of MTMS contributes only 1 mole of silicon. Preparation conditions and measured properties of all of the polymer-reinforced aerogels are listed in Table 4, while the unreinforced (native) aerogels are listed in Table 5. The run number represents a particular formulation made at once in a single batch. The order of preparation of individual formulations was random to reduce the correlation of systematic errors with any variable.

Data for the aerogel formulation in Tables 4 and 5 were modeled using multiple linear least-squares regression analysis to produce a variety of empirical models for various properties of the aerogels as described more fully below, considering a model including all first-order effects of the four variables, as well as all two-way interactions. All of the variables were orthogonalized (transformed to a −1 to +1 scale) prior to modeling to minimize correlation among terms. Terms not statistically significant (<90% confidence) were dropped from the model one at a time by the backward stepwise modeling technique.

Preparation conditions and resulting properties of MTMS and BTMSPA aerogels, made in either acetonitrile or acetone are listed in Table 4 (polyurethane/urea reinforced aerogels) and Table 5 (non-reinforced aerogels). BTMSPA, a silane precursor containing a secondary amine, serves as a base catalyst for gelation as well as a reactive site for polymerization with the tri-isocyanate, Desmodur N3300A, shown in Scheme 1. The water/total silicon mole ratio, r, used in the initial hydrolysis and condensation of silane precursors is calculated based on the number of moles of water over the total moles of silicon (taking into account that BTMSPA contributes two moles of silicon per mole). According to Brinker and Scherer *Sol-Gel Science: The Physics and Chemistry of Sol-Gel Processing*; Academic Press, Inc., San Diego, Calif., 1990, an r of two is considered stoichiometric for hydrolysis and condensation. However, an excess of water is usually needed for complete reaction. In this example, we varied r from two to five. In addition, the number of washes in clean solvent after gelation and before reacting with polymer was varied from one to three. Washing removes water and alcoholic by-products of condensation. As previously described, when isocyanates are used as the polymer reinforcement, the amount of water left in the gels after condensation also can affect the number of repeat units in the polymer cross-links. Meador et al. *Chem. Mater.* 2007, 19, 2247-2260. As shown in Scheme 2 immediately below, excess water reacts with the isocyanate to generate an amine which can react with other isocyanates to extend the polymer chain before reacting with amines attached to the silicon surface. Too little water can result in incomplete hydrolysis of the starting silanes while too much water can lead to too much polymer being incorporated into the aerogels. Hence, a balance between the amount of water needed for gelation and the amount of water remaining in the gels for chain extension is desirable.

41.8 ppm) closest to the nitrogen can give an indication of the degree of polymer cross-linking (n value from Scheme 2) depending on preparation conditions. In the absence of chain-extension reactions, the cross-linked structure would be as shown in Scheme 1 where one molecule of tri-isocyanate has reacted with three different amines on the gel backbone. This would give a ratio of peak B to peak A of 1. A ratio of less than 1 would indicate that some of the amine has not reacted. A ratio of more than 1 would indicate some degree of chain extension. The highest ratio of isocyanate to amine measured for aerogels prepared in acetonitrile, was 1.2 as shown in FIG. 15*a* for a spectrum of the monolith from sample 7 made using the highest level of total silicon (1.65 mol/l), 80 mol % BTMSPA, an r=5 and only one wash. The corresponding aerogel made in acetone (sample 32), shown in FIG. 15*b*, shows more

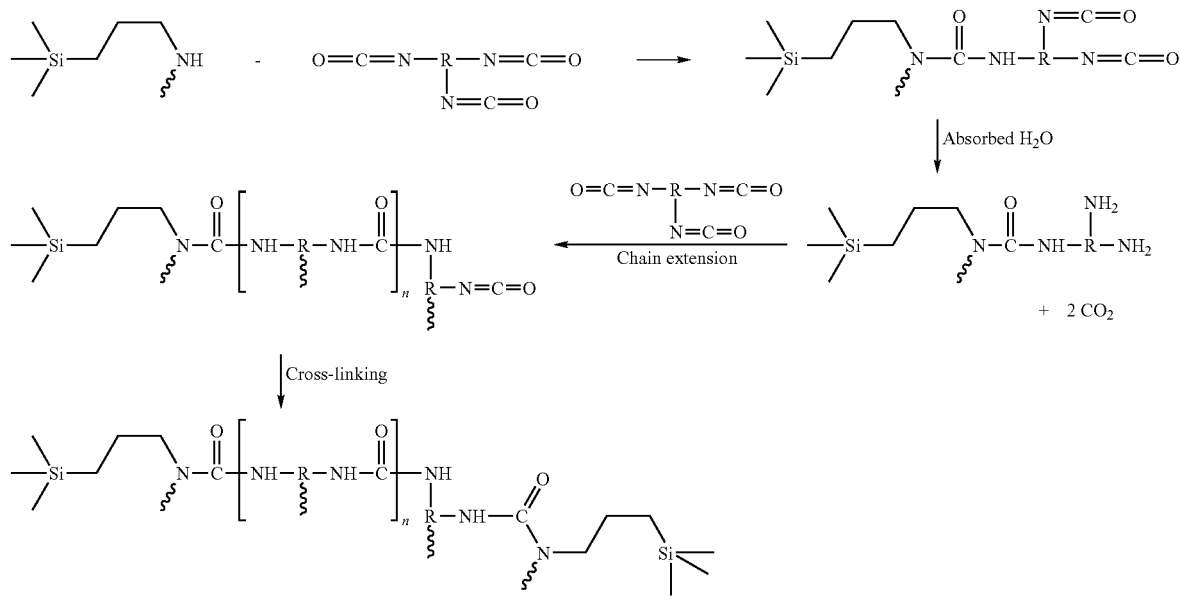

Scheme 2. Mechanism for cross-linking with tri-isocyanate, including chain-extension reaction due to excess water.

Figure 14:
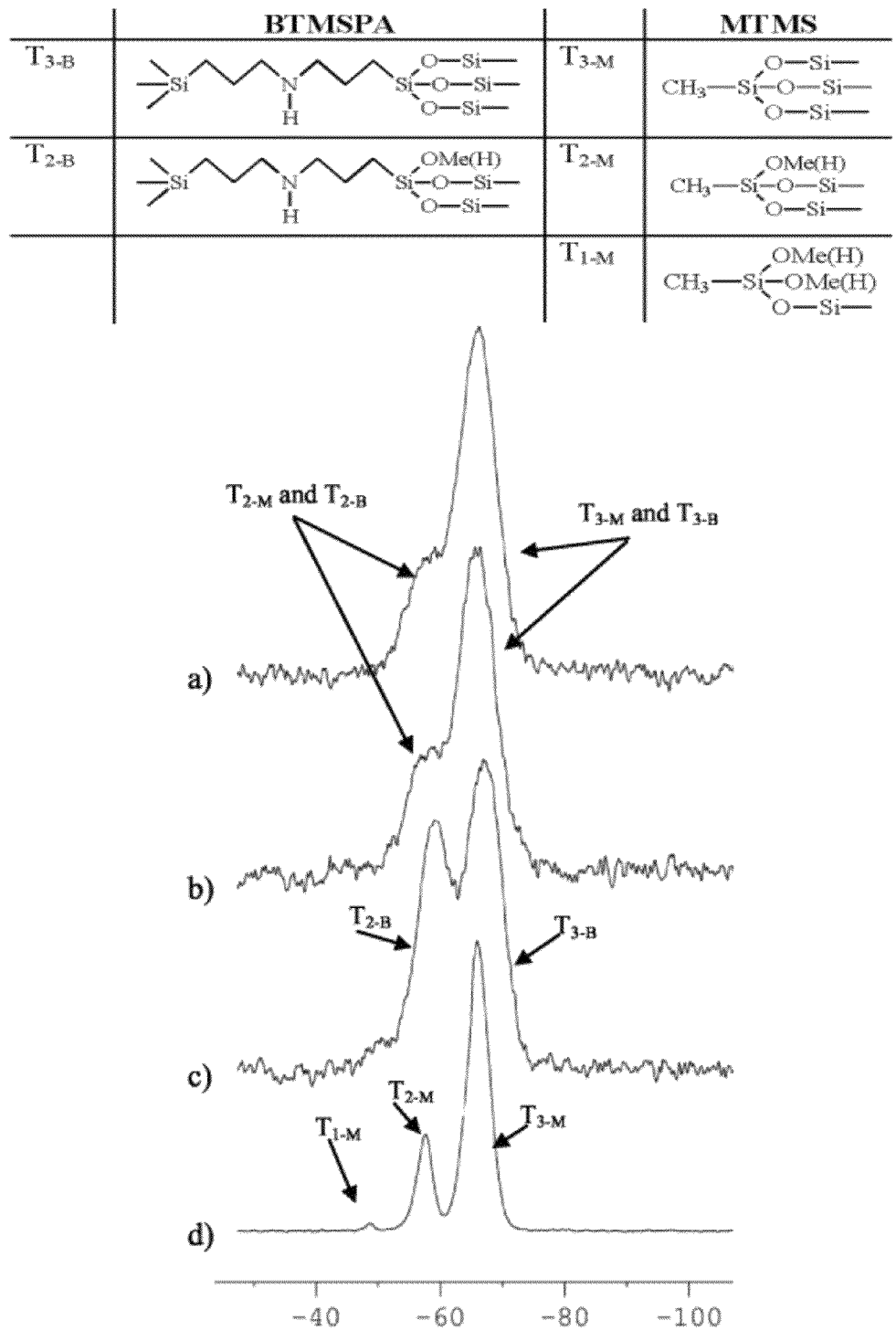
FIG. 14 shows solid $^{29}$Si NMR spectra of samples from formulations listed in Table 4 of Example 5 as a) 23 with r=5 and b) 28 with r=2, and aerogels formulated from c) BTMSPA alone and d) MTMS alone. All samples shown were prepared in acetonitrile.

Solid $^{29}$Si NMR spectra of selected reinforced aerogel samples, prepared in acetonitrile, from this example are shown in FIG. 14 along with samples prepared from BTMSPA and MTMS alone. It is evident from comparing FIG. 14*d* (MTMS derived sample) and FIG. 14*c* (BTMSPA derived sample) that the Si peaks completely overlap at −66 ppm ($T_3$ peak) and −58 ppm ($T_2$ peak). Spectra of polymer-reinforced aerogels produced from 1.65 M total silicon with 40 mol % coming from BTMSPA are shown in FIG. 14*a* (using r=5) and FIG. 14*b* (using r=2). The r value has very little effect on the gel formation as there is very little difference in the two spectra, both having a large $T_3$ peak and a smaller $T_2$ side peak, indicating that extent of condensation is about the same at different r for samples made using 3 washes. The same is true when comparing samples made using 1 wash.

Figure 15:
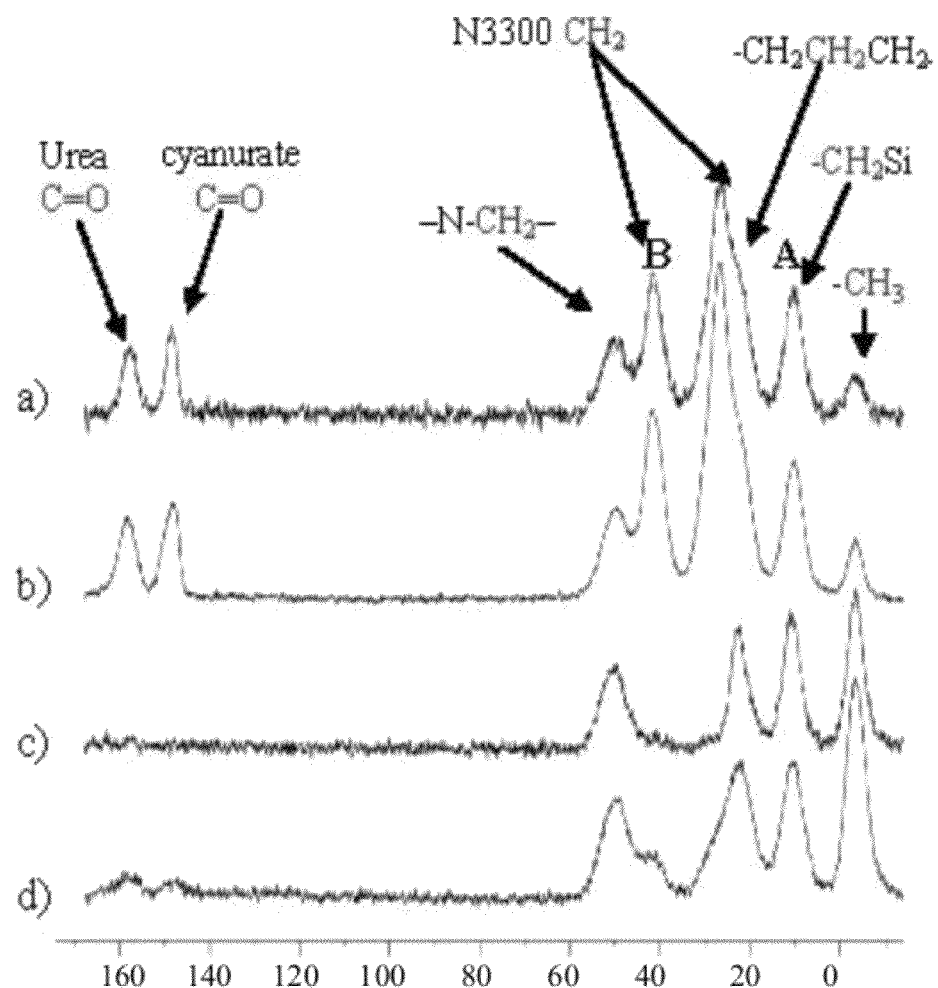
FIG. 15 shows solid $^{13}$C NMR spectra of samples from formulations listed in Table 4 of Example 5. Sample spectra shown in a) acetonitrile and b) acetone were fabricated using 1.65 mol/l total Si with 80 mol % BTMSPA-derived Si, while c) acetonitrile and d) acetone were fabricated from 0.75 mol/l total Si with 40 mol % BTMSAP-derived Si.

Solid $^{13}$C NMR spectra of selected reinforced aerogel samples from this example are shown in FIG. 15. The spectra all contain one peak at −3.7 ppm assigned to the methyl group from MTMS, and three methylene peaks at 10.9, 23.2 and 49.9 ppm from BTMSPA. Additional peaks in the spectra come from the methylenes (28 and 41.8 ppm) and carbonyls (148.3 and 157.7 ppm) of the tri-isocyanate cross-linker. Integration of the BTMSPA methylenes (peak A at 10.9 ppm) closest to the Si with the tri-isocyanate methylenes (peak B at 41.8 ppm) closest to the nitrogen can give an indication of the incorporation of isocyanate with a ratio of 1.6. As the total silicon concentration and mol % of BTMSPA are decreased to 0.75 mol/l, isocyanate to amine ratio decreases as shown in spectra in FIG. 15*c* for acetonitrile-derived monolith (sample 21) and 2*d* for acetone-derived monolith (sample 37). In fact, for sample 21, no tri-isocyanate is incorporated, while sample 37 has a peak B:A ratio of 0.26 indicating that only a fourth of the amines are reacted.

Figure 16:
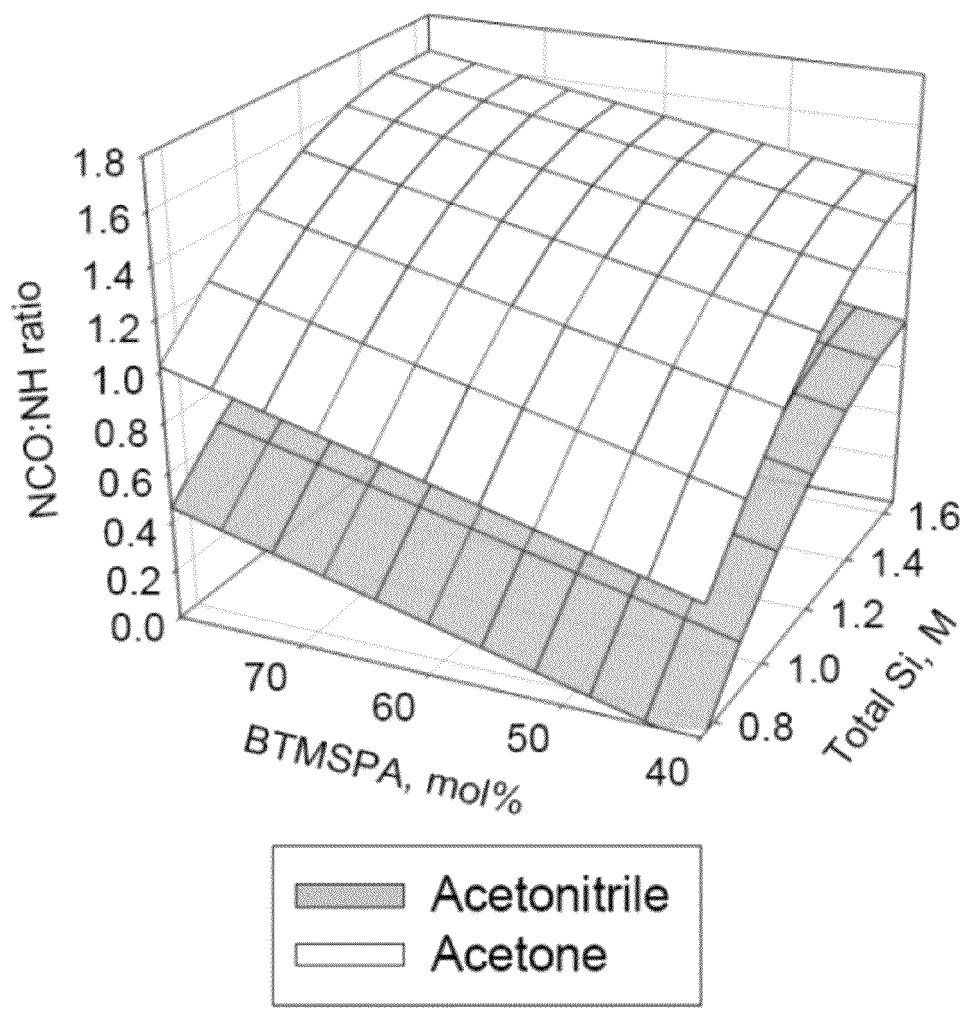
FIG. 16 shows an empirical model of tri-isocyanate to amine ratio measured from integration of $^{13}$C NMR spectra data from Example 5 (FIG. 15) graphed vs. BTMSPA fraction and total Si.

Use of acetone as a solvent instead of acetonitrile increased the reaction with amine across the whole example (this Example 5), as shown in the empirical model for the extent of cross-linking based on the ratio of peak B:A integration (standard error=0.11, R2=0.90) shown in FIG. 16. Increasing total Si and fraction of BTMSPA-derived Si also significantly increased the amount of cross-linking. An isocyanate to amine ratio of at least one (balanced stoichiometry as shown in Scheme 1) is produced in acetonitrile when 1.65 mol/l total Si and BTMSPA-derived Si of at least 60 mol % are used or with 80 mol % BTMSPA-derived Si, and at least 1.2 mol/l total Si. For acetone-derived monoliths under these same conditions, chain extension as shown in Scheme 2 becomes a factor.

Figure 17:
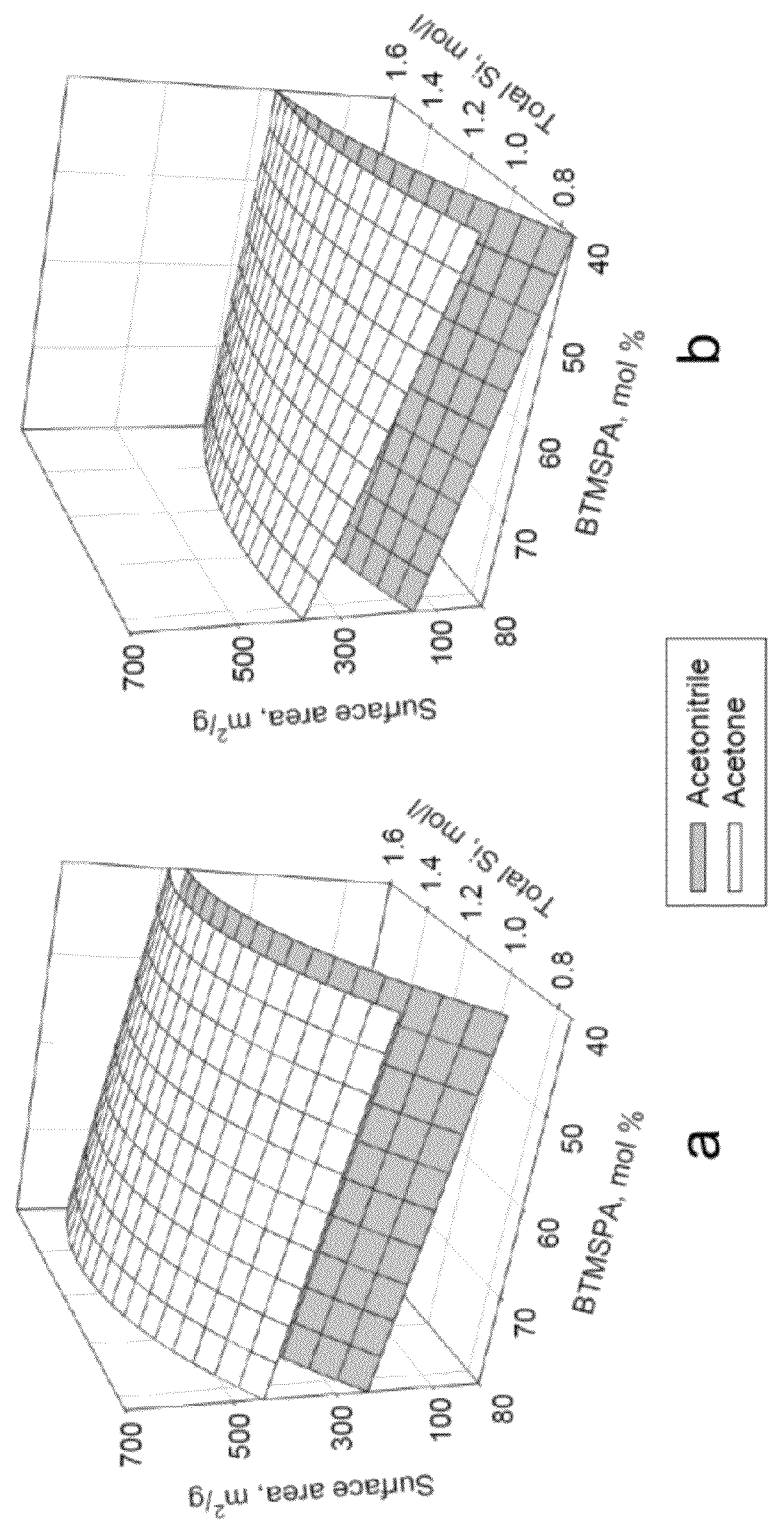
FIG. 17 shows empirical models of BET surface areas graphed vs. total Si and BTMSPA fraction for a) non-reinforced aerogels produced in accordance with Example 5 and b) aerogels reinforced with tri-isocyanate produced in accordance with Example 5.

A clue to why there is very little incorporation of tri-isocyanate at lower total Si and low BTMSPA fraction, especially in acetonitrile processed aerogels, comes from examining the BET surface areas measured for the aerogel monoliths. The empirical model for BET surface area is shown in FIG. 17*a* for non-reinforced aerogels (standard error=48.9%, R2=0.89). From the graph, it is clear that surface area decreases with decreasing total Si and decreasing BTMSPA fraction, especially in acetonitrile. As BTMSPA fraction is decreased, MTMS fraction increases, leading to more non-polar methyl groups present on the silica surface. Interaction of the methyl groups with the more polar acetonitrile causes a collapse of the skeletal backbone of the gel. Acetone prepared non-reinforced aerogels also decrease in surface areas with decreasing total Si and BTMSPA fraction, but the effect is much smaller. Lower surface areas in the gels before cross-linking would mean less surface amine is available for reaction with isocyanate. The empirical model of BET surface area for those monoliths treated with cross-linker (standard error=15.8%, $R^2$=0.97) is shown in FIG. 17*b*. In general, the surface area decreases with increasing amount of polymer reinforcement compared to non-reinforced aerogels but follows the same trend as the non-reinforced aerogels.

Figure 18:
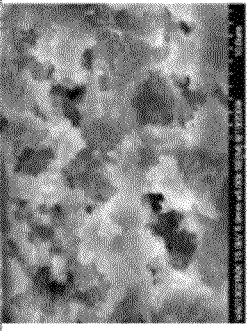
FIG. 18 shows SEM images of select non-reinforced samples (a, b and c) from Table of Example 5, compared to corresponding reinforced aerogels from Table 4 of that example prepared using acetonitrile as solvent (d, e and f), and using acetone as solvent (g, h and i).

Scanning electron micrographs (SEM) of select samples from the example shown in FIG. 18 illustrate the differing morphologies arising from different processing conditions. Non-reinforced aerogels shown in FIG. 18*a-c* illustrate the increase in particle size and decrease in surface area as total Si and BTMSPA fraction is reduced (noting that sample 37 from Table 5 shown in FIG. 18*c* is at a different scale). For aerogels prepared in acetonitrile using 1.65 mol/l total Si, polymer cross-linking does not change the appearance of the gel structure as seen by comparing SEMs shown in FIGS. 18*a* and *b* to those shown in FIGS. 18*d* and *e*, respectively, although the surface area is about halved in the reinforced samples. In contrast, particle sizes appear to be larger for the comparable polymer-reinforced aerogel made in acetone using the highest total Si and highest BTMSPA (FIG. 18*g*). This sample has the most amine content and the highest surface area before cross-linking. Hence, all of the amines are readily available for reaction with tri-isocyanate. For the polymer-reinforced aerogel made in acetone using 1.65 mol/l total Si and 40 mol % BTMSPA (FIG. 18*h*), the particle sizes again appear comparable to the acetonitrile-prepared sample shown in FIG. 18*e*, although density is much higher and amount of isocyanate reacted per amine is about doubled over the acetonitrile-prepared sample. It should also be noted that the monolith shown in FIG. 18*g* has more polymer incorporated than that shown in FIG. 18*h*. Though the sample shown in FIG. 18*h* (run 39 from Table 4) has a larger ratio of isocyanate to amine (Peak B:A), the amount of amine in the sample shown in FIG. 18*g* (run 32 from Table 4) is twice as much. Reinforced aerogels prepared in acetone using 0.75 mol/l total Si (FIG. 18*i*) are also similar in appearance to the comparable non-reinforced aerogels (FIG. 18*c*), both having the fine pore structure typical of a low density aerogel. In fact, these samples are not that different in density, porosity or surface area, since there is very little polymer incorporated in the cross-linked sample (only about 20% of the amines are reacted.) The comparable acetonitrile-prepared sample, shown in FIG. 18*f*, in contrast, has very large particle sizes which are smoother in appearance, again demonstrating that the fine pore structure of the aerogel is lost under these conditions. Indeed, as previously discussed and evidenced by NMR, in this sample, almost no tri-isocyanate is incorporated.

Figure 19:
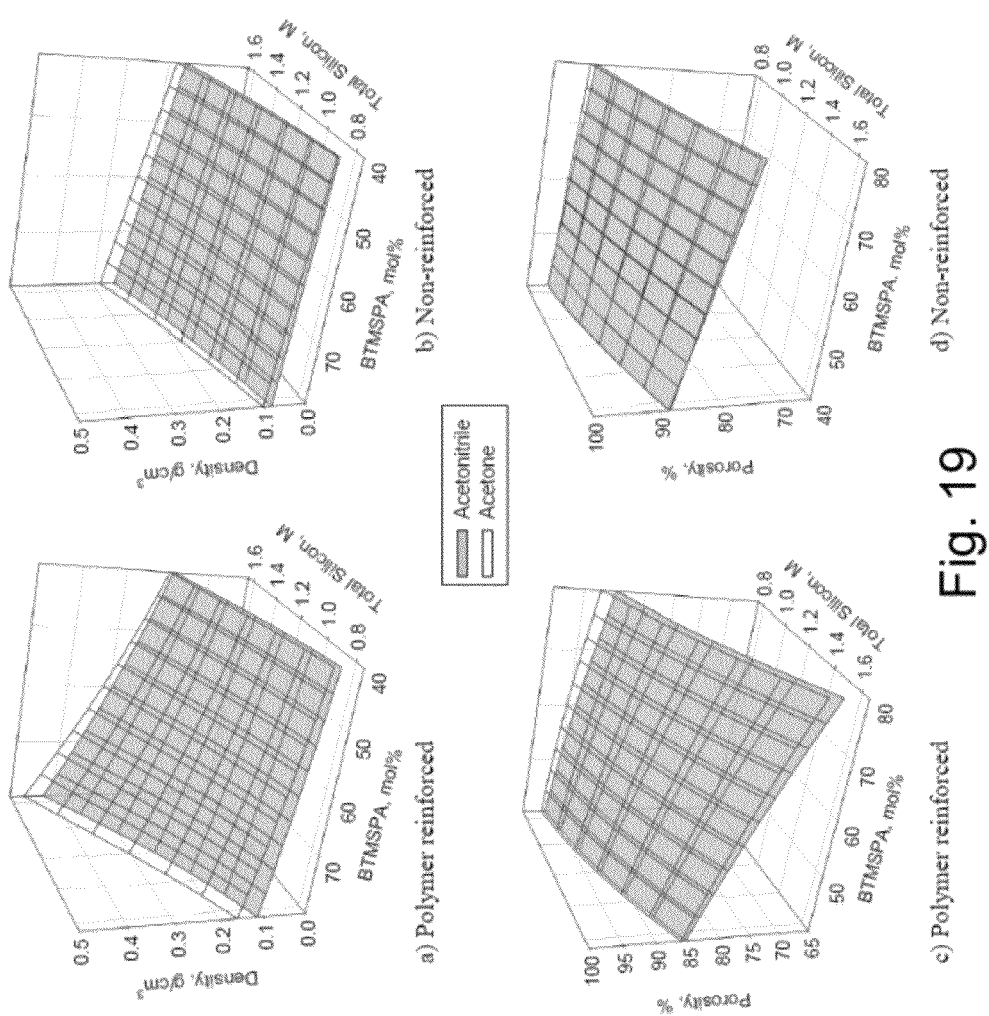
FIG. 19 shows empirical models graphed vs. mol % of BTMPSA and total Si concentration of density (a and b) and porosity (c and d), comparing non-reinforced samples and polymer reinforced samples prepared using acetone or acetonitrile in Example 5.

The empirical model derived for density of the polymer reinforced monoliths (standard error=0.11, $R^2$=0.90) in FIG. 19*a* is compared to that of the non-reinforced aerogels (standard error=0.35, $R^2$=0.99) in FIG. 19*b*. For both non-reinforced and polymer-reinforced aerogels, increasing total Si concentration and mol fraction of BTMSPA increases density both by adding more silica to the structure and more organic linking groups to the backbone. Increasing BTMSPA fraction increases density more for reinforced aerogels, especially at higher total Si due to an increase in amine sites available for tri-isocyanate reaction. However, since there is little polymer incorporated in formulations with the lowest total silicon and BTMSPA mol fraction as seen by NMR, similar densities are obtained for non-reinforced and reinforced samples under those conditions. Increasing Si to water ratio and decreasing the number of washes (not shown in the plots) also causes a small though significant increase in density.

The empirical models for porosity for reinforced aerogels (standard error=0.72%, $r^2$=0.99) and non-reinforced aerogels (standard error=0.55%, $r^2$=0.99) are shown in FIGS. 19*c* and 19*d*, respectively. As is typically the case, porosity follows the opposite trends as density (noting that the x and y planes are rotated compared to FIGS. 19*a* and 19*b*). Thus, increasing total Si concentration decreases porosity for both reinforced and non-reinforced aerogels. Increasing BTMSPA mol fraction tends to decrease porosity, though this effect is larger for the polymer-reinforced aerogels. This is because increasing available amine sites from BTMSPA increases the amount of tri-isocyanate incorporation. As seen in table 4, the reinforced aerogels in this example had porosities in the range of 69.2-97.0. In preferred embodiments, the porosity is at least 80%, preferably at least 90%, preferably at least 95%.

Of course, the density and porosity are also influenced by the dimensional change or shrinkage (%) of a monolith over the course of processing the aerogels. In this example, shrinkages were small, ranging from 0.4 to 12% for the polymer-reinforced aerogels and 0.6 to 14% for the non-reinforced aerogels. BTMSPA fraction has the largest effect on shrinkage, which increases by up to 9% over the whole range for non-reinforced aerogels and up to about 6% for reinforced aerogels. The polymer-reinforced aerogels tended to shrink 2-3% less than the non-reinforced aerogels especially at higher total Si concentration. The aerogels prepared in acetonitrile tended to shrink 1-2% less than those made in acetone. Overall, increasing total Si concentration had a minor impact on shrinkage for both non-reinforced and reinforced aerogels (~2% over the whole range).

Figure 20:
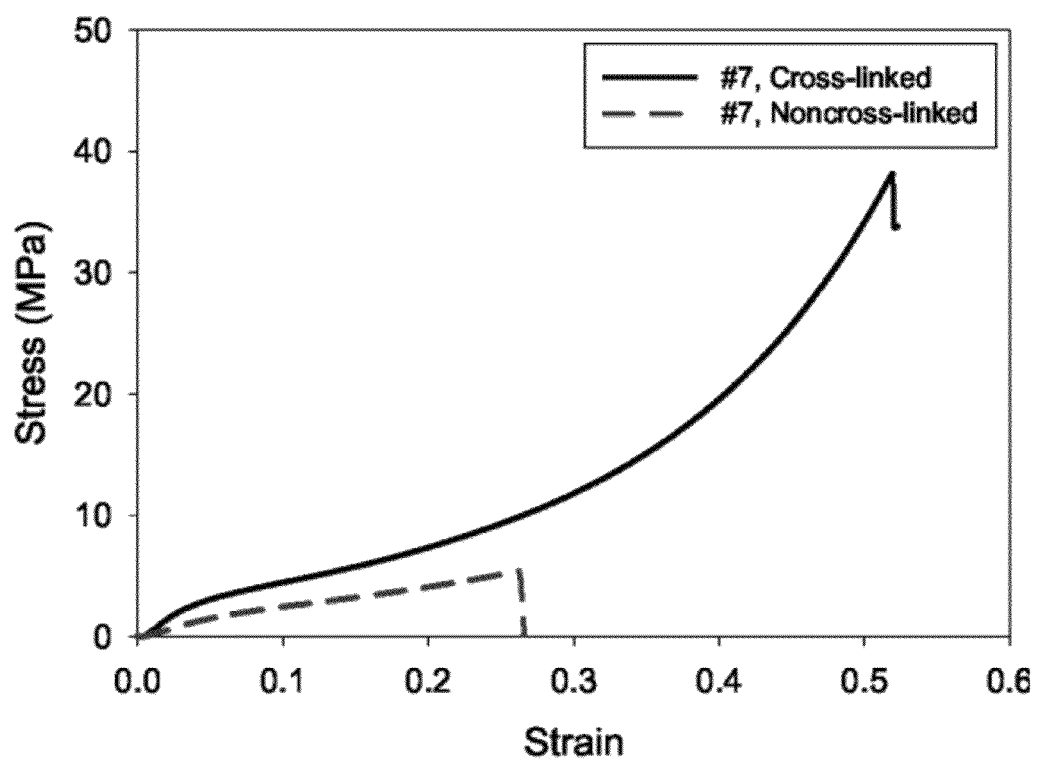
FIG. 20 shows typical stress-strain curves of a polymer-reinforced aerogel (solid line) compared to a non-reinforced aerogel, both prepared in acetonitrile according to Example 5.
Figure 21:
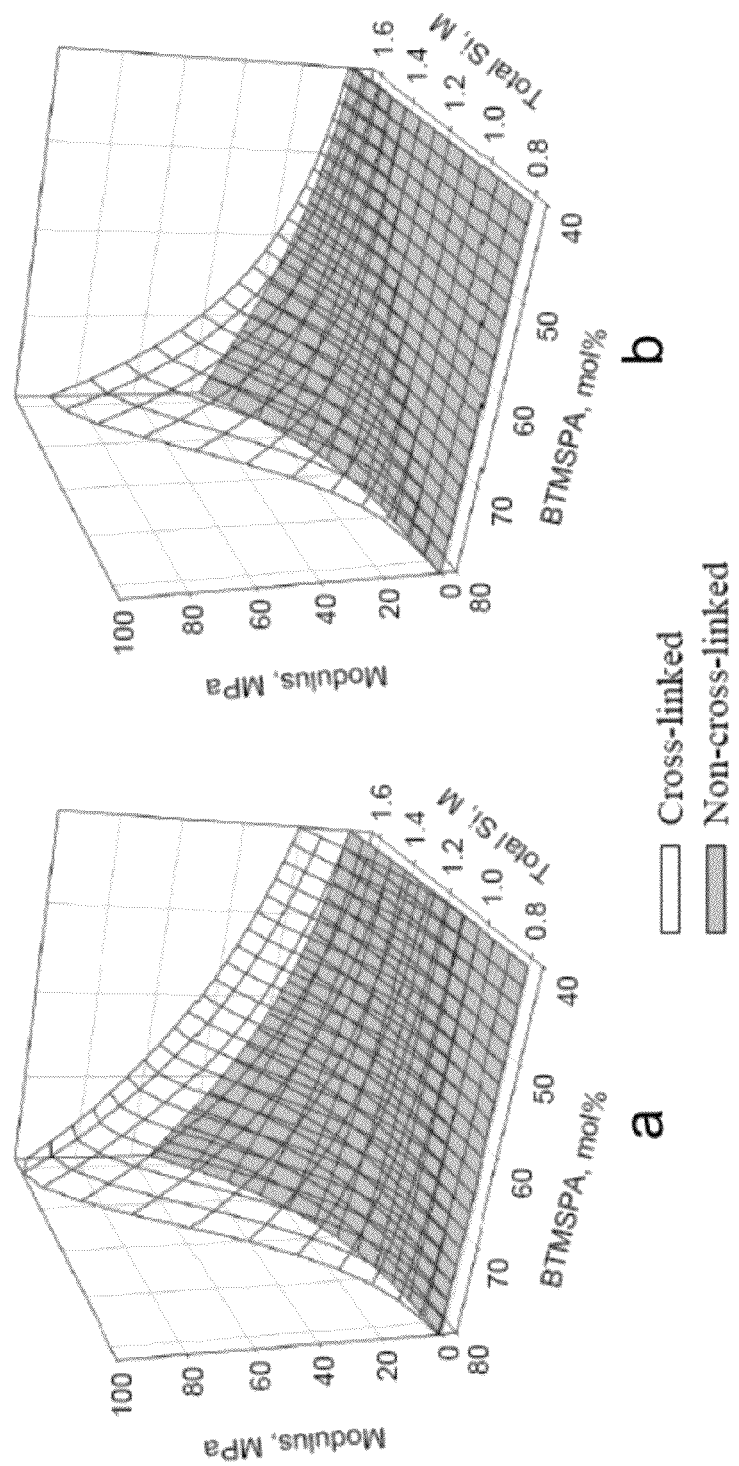
FIG. 21 shows empirical models of modulus graphed vs. BTMSPA fraction and total Si of reinforced aerogels compared to non-reinforced aerogels made in a) acetone and b) acetonitrile according to Example 5.

As an example, stress-strain curves from compression tests for reinforced and non-reinforced aerogels from formulation 7 from Tables 4 and 5 made using 1.65 total Si, 80 mol % Si from BTMSPA are shown in FIG. 20. Elastic modulus from each compression test is calculated from the initial slope of the stress strain curves. As seen in the example curves, typically the modulus is slightly higher for the polymer reinforced samples while stress at break is much increased. Shown in FIG. 21 are the empirical models for modulus graphed vs. total Si concentration and mol fraction of BTMSPA for both non-reinforced aerogels (standard error=0.19, $r^2$=0.99+) and polymer-reinforced aerogels (standard error=0.09, $r^2$=0.99+) made in acetone (FIG. 21*a*) and acetonitrile (FIG. 21*b*). Modulus increases with an increase in total silicon concentration and mol % of BTMSPA for both non-reinforced and reinforced aerogels. This is expected since, in a broad sense, modulus typically scales with density in aerogels. Aerogels prepared in acetone solvent also had higher modulus (approximately one order of magnitude higher according to a first approximation; compare range of 0.001 to 84 MPa for acetonitrile to range of 0.01 to 158 MPa for acetone from table 4) than those made in acetonitrile, since acetone prepared aerogels contain more polymer and also shrink slightly more than those prepared in acetonitrile. In preferred embodiments, a silica monolith preferably has a Young's modulus of at least 0.01, preferably at least 0.1, preferably at least 1, preferably at least 10, preferably at least 100, MPa. Note also that non-reinforced aerogels prepared in acetone had slightly higher modulus than those prepared in acetonitrile, possibly also due to slightly greater shrinkage contributing to an increase in density. Water ratio (not shown) also has a slight effect on modulus, increasing with increasing amount of water for both acetone- and acetonitrile-prepared aerogels. As previously noted, increasing amount of water affects both the underlying silica gel structure (more complete hydrolysis) as well as the polymer cross-linking (chain extension). No significant effect on number of washes before cross-linking was seen over and above random error.

Figure 22:
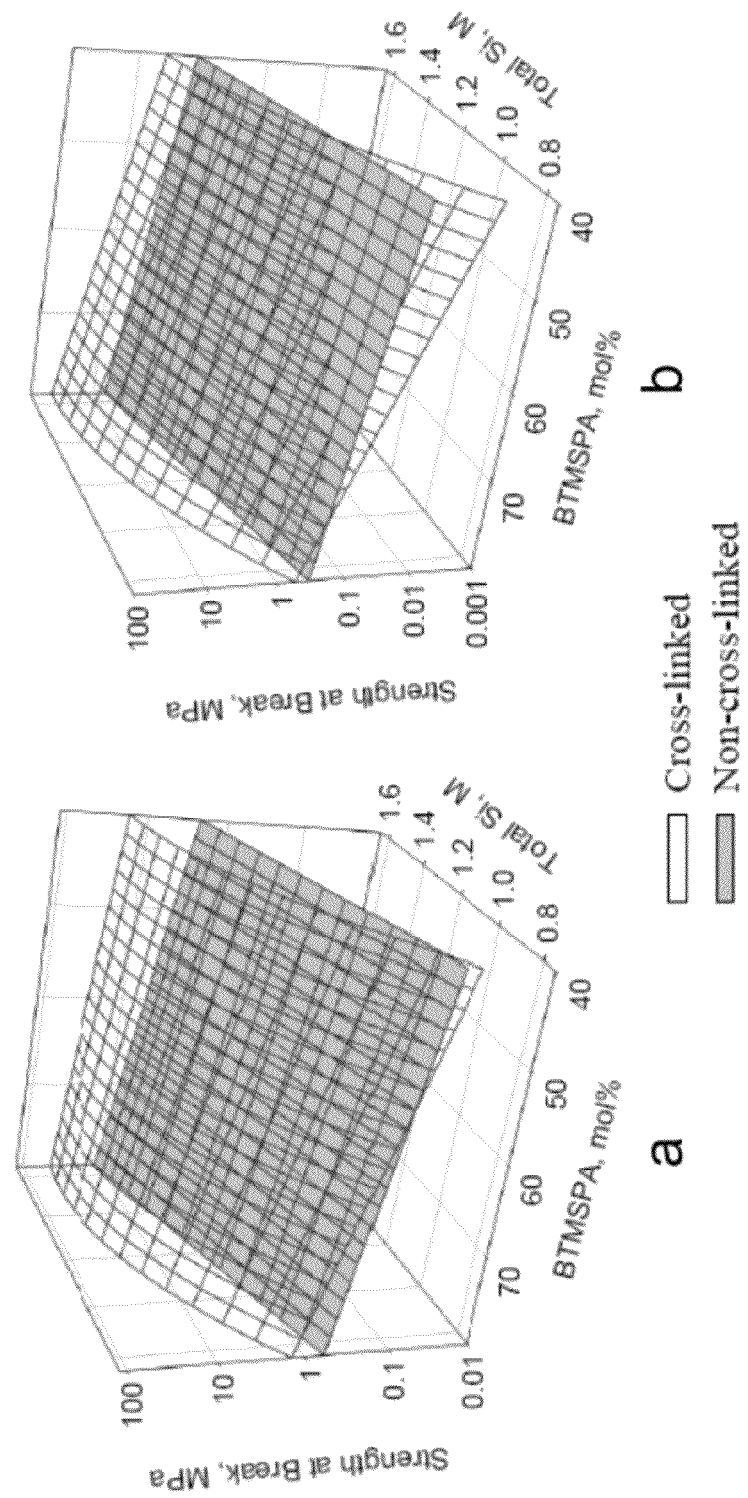
FIG. 22 shows empirical model of strength at break graphed vs. BTMSPA fraction and total Si of reinforced aerogels compared to non-reinforced aerogels made in a) acetone and b) acetonitrile according to Example 5.

Empirical models for maximum strength at break are shown in FIG. 22 for non-reinforced aerogels (standard error=0.58, $r^2$=0.94) and polymer-reinforced aerogels (standard error=0.35, $r^2$=0.99), using acetone as solvent (FIG. 22$a$) and acetonitrile as solvent (FIG. 22$b$). As with modulus, in general, as the total Si concentration and BTMSPA mol fraction increases, the maximum stress increases. In addition, polymer-reinforced aerogels are as much as an order of magnitude higher in maximum strength at break than their unreinforced counterparts, indicating that the crosslinker indeed enhances the mechanical properties. Unlike modulus, no significant effect of water ratio was seen on the maximum stress, over and above random error. This suggests strength at break is not as sensitive to the degree of chain extension or condensation of silica gel structure. Since failure occurs during densification, it is the amount of material present that governs this property. The maximum strength at break for monoliths prepared in acetone at lower BTMSPA fraction is higher compared to those prepared in acetonitrile, due to larger amount of polymer incorporated in the acetone aerogels.

An alternative approach to characterizing the overall strength in these aerogels is to examine toughness. The toughness of a material is the amount of energy required to deform a volume of material to its breaking point—hence its units are J/m$^3$. Toughness analysis was performed as it was noted that polymer-reinforced aerogels displayed not only higher stress at break than their native counterparts, but about 20% more strain at break on average. Toughness is calculated by taking the area under the stress-strain curve. Integration of the trendline equation matching the stress-strain data, and having an R-squared value greater than 0.99, was performed for each stress-strain measurement. Hence, as an example, in the curves shown in FIG. 20, strain at break is nearly double for the polymer-reinforced aerogels. Note that this analysis is normally performed for experiments in tension loading, and as such direct comparisons to other systems outside this example may not be valid.

Figure 23:
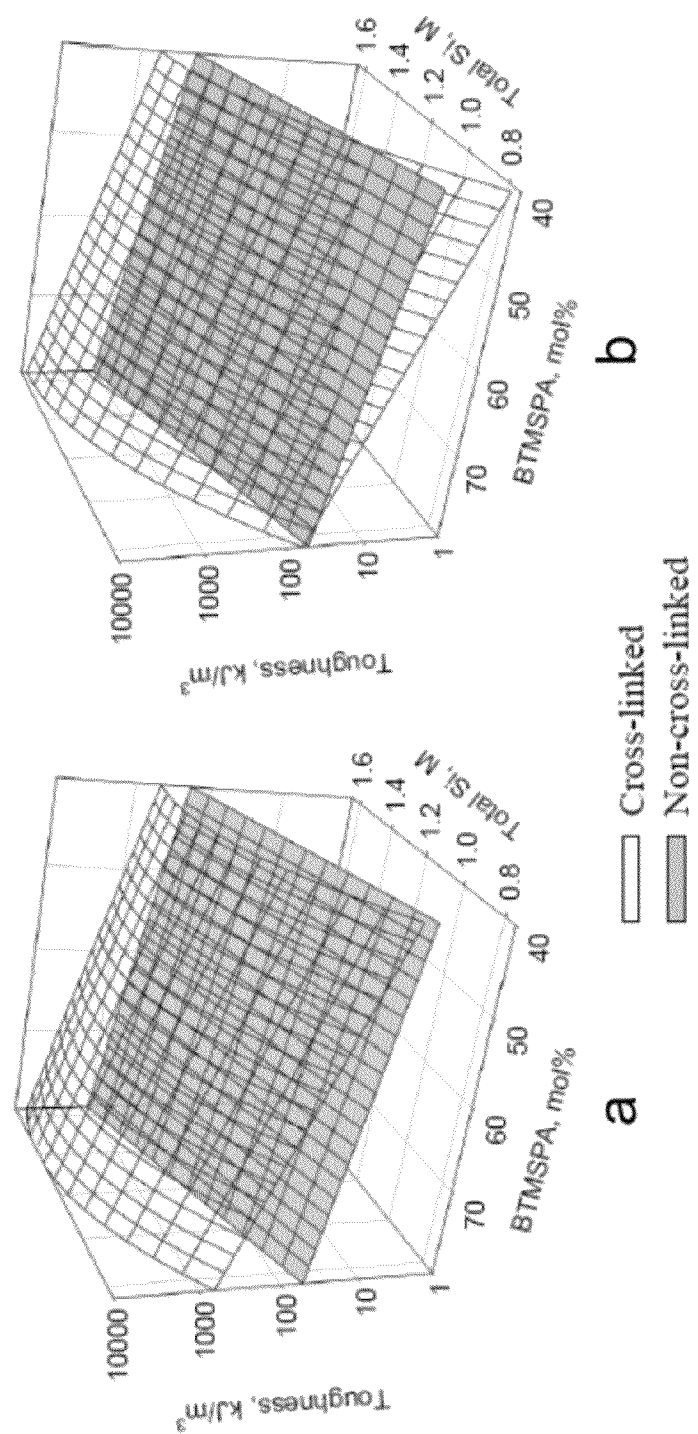
FIG. 23 shows empirical model of toughness graphed vs. BTMSPA fraction and total Si of reinforced aerogels compared to non-reinforced aerogels made in a) acetone and b) acetonitrile according to Example 5.

Empirical models for toughness for non-reinforced (standard error=0.69, $r^2$=0.92) and reinforced aerogels (standard error=0.35, $r^2$=0.99) are shown in FIG. 23 graphed vs. total Si concentration and mol fraction BTMSPA for acetone-prepared samples (FIG. 23$a$) and for acetonitrile-prepared samples (FIG. 23$b$). Polymer reinforced samples made using 80 mol % Si derived from BTMSPA show up to an order of magnitude increase in toughness over non-reinforced samples of the same composition. In particular, reinforced silica monoliths preferably have a toughness of at least 300, 400, 1000, 2000 or 4000, kJ/m$^3$, and non-reinforced silica monoliths preferably have a toughness of at least 100, 200, 300 or 400 kJ/m$^3$. This improvement is of course attributable to the reinforcement effect of the polymer conformal coating.

The overall trends for toughness are the same as those for strength at break, due to the shape of the compression curves, and the same for monoliths made in acetone. As the aerogels are compressed, they eventually undergo a densification as porosity is lost. Katti et al. *Chem. Mater.* 2006, 18, 285-296. When this occurs, a noticeable upturn in the stress-strain curve appears, as seen in the polymer reinforced sample in FIG. 20. Ultimate failure normally occurs for the reinforced aerogels in this regime, and the values for stress of the aerogel under densification are significantly higher than that of the initial deformation. Hence, toughness follows the same trends as strength at break with as much as an order of magnitude increase over the non-reinforced aerogels. In addition, polymer-reinforced aerogels prepared in acetone at low total Si concentration are higher in toughness than those prepared in acetonitrile, again because of the greater amount of polymer cross-linking in the acetone derived aerogels. At high total Si concentration there is not as much difference in toughness between reinforced aerogels made in acetone or acetonitrile.

Figure 24:
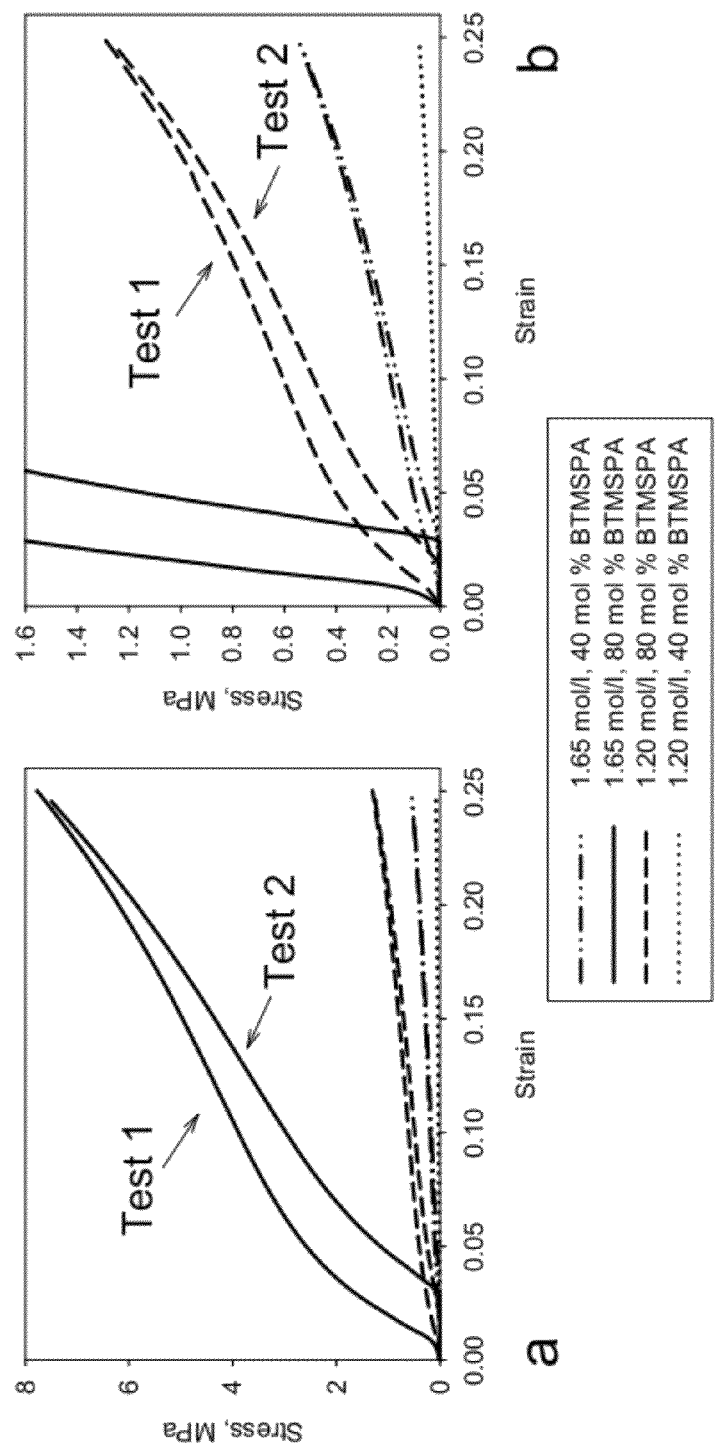
FIG. 24 shows typical stress-strain curves for a repeat compression tests on various polymer reinforced samples with different total silicon concentration and BTMSPA levels of monoliths prepared in acetonitrile according to Example 5.

As previously reported by Kanamori and Rao cited above, flexibility and good recovery after compression are features of MTMS-derived aerogels. As a way of quantifying these properties for the aerogels from this example, the monoliths were taken through two consecutive compression cycles to 25% strain and allowed to recover for thirty minutes. The difference in the length of the samples before and after both tests is considered the amount of unrecovered strain and is listed in Tables 4 (polymer-reinforced aerogels) and 5 (non-reinforced aerogels). The lower the value of unrecovered strain is, the more elastic the aerogel monolith. To illustrate, stress-strain curves for repeat compression tests to 25% strain of different polymer-reinforced aerogels are compared in FIGS. 24$a$ and 24$b$. The pairs of lines in the figures represent two subsequent stress-strain curves, labeled Test 1 and Test 2, from four different formulations. The polymer-reinforced aerogel formulation giving the pair of solid lines is made from 1.6 mol/l total Si and 80 mol % Si from BTMSPA (run 7 from Table 4). The curve labeled Test 1 is the first compression and Test 2 is the second compression. In this example, about 3% strain is not recovered. In contrast, the pair of equal-segmented lines shows repeat compression cycles from formulation 13, made using 1.2 mol/l total Si and 80 mol % BTMSPA-derived Si. In this case, unrecovered strain is 1.1% after both tests. The pairs of unequal-segmented lines and dotted lines represent other formulations with lower modulus and similar recovery.

Figure 25:
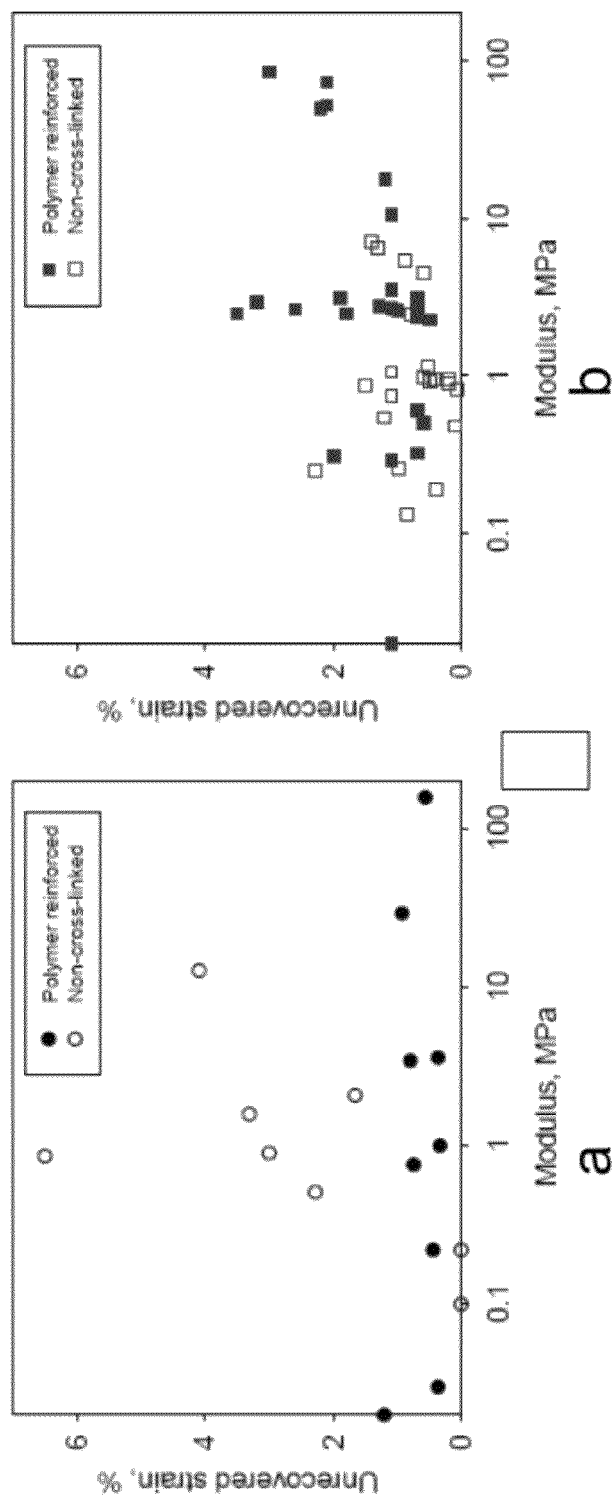
FIG. 25 shows graphs of unrecovered strain vs. modulus for all aerogels in prepared in Example 5, showing polymer reinforced and non-crosslinked aerogels made in a) acetone and b) acetonitrile.

Note in Tables 4 and 5 that most of the non-reinforced and reinforced aerogels made using MTMS and BTMSPA exhibit low unrecovered strain (samples spring back from compression), consistent with good elasticity. While typically there is a trade-off between modulus and recovery after compression, in this example the trade off is very small, with even the highest-modulus reinforced aerogels exhibiting only up to 3% unrecovered strain for those made in acetonitrile and up to 1.2% for those made in acetonitrile. FIG. 25 shows graphs of modulus vs. unrecovered strain for acetone- (FIG. 25$a$) and acetonitrile- (FIG. 25$b$) derived aerogels. While there is a slight increase in unrecovered strain as modulus increases for non-reinforced aerogels and for the polymer-reinforced aerogels made in acetonitrile, the polymer-reinforced aerogels made in acetone show 0 to 1% unrecovered strain across the whole range of modulus. Since the acetone-derived samples also have higher incorporation of tri-isocyanate, this indicates that hexyl linkages from the tri-isocyanate contribute to the flexibility of the overall network. In preferred embodiments, the silica monolith exhibits not more than 3, preferably not more than 2, preferably not more than 1, preferably not more than 0.5, percent unrecovered strain following compression to 25% strain 30 minutes after release of the compression force. Consistent with the data in tables 4 and 5, preferably the monolith exhibits the aforementioned maximum unrecovered strain values following a cycle of two compressions, each to 25 percent strain, 30 minutes after release of the compression force for the second compression.

The combination of MTMS and BTMSPA used in the silica backbone provides enhanced elastic properties to tri-isocyanate reinforced silica aerogels. The dipropylamine spacers from BTMSPA contribute flexible linking groups in the silica structure, as well as reactive sites via their secondary amines for reaction with a triisocyanate, Desmodur N3300A. The trifunctional isocyanate provides an extended degree of branching or cross-linking, resulting in up to an order of magnitude increase in compressive strength of the aerogel monoliths while the overall flexibility arising from the underlying silica structure is maintained. The compressive moduli of the reinforced aerogel monoliths in this example range from 0.001 to 84 MPa for those prepared in acetonitrile and 0.01 to 158 MPa for their counterparts made in acetone. All formulations across this entire range of modulus recover nearly all of their length after two compressions to 25% strain. This result represents an order of magnitude improvement in modulus for aerogels which recover completely after compression, compared to previous polymer-reinforced aerogels studied. Higher total silicon concentration and mole fraction of Si derived from BTMSPA result in larger amounts of tri-isocyanate incorporation, and enhanced compressive strength and toughness. In addition, the strongest monoliths still have surface areas greater than 200 m$^2$/g measured by BET and densities less than 0.5 g/cm$^3$, only a 50% increase in density over the non-reinforced aerogels of the same formulation. In contrast, at low total silicon concentration and low mole % of BTMSPA-derived Si, little or hardly any reaction occurred with tri-isocyanate, resulting in modest or no improvement in mechanical properties. These formulations also produced monoliths with lower surface area and larger pore sizes. Accordingly, it is preferred that the BTMSPA-derived Si comprise at least 40 mol %, preferably at least 60 mol %, most preferably at least 80 mol % based on the total silicon in the silica network. In general, the use of acetone as a solvent in preparation of aerogels result in higher BET surface areas and better mechanical properties compared to those made in acetonitrile. These results may be enabling for aerospace applications such as EDL systems and EVA suits which demand a combination of superior insulation durability and flexibility.

Example 6

Flexible, Recoverable Aerogels Incorporating bis[3-(triethoxysilyl)propyl]disulfide Flex-Link and Vinyl Functionality In this example, [3-(triethoxysilyl)propyl]disulfide, BTSPD, was used as a flex-link in silica aerogels. It is contemplated that other [3-(trialkoxysilyl)alkoxy]disulfides or [3-(trialkoxysilyl)alkoxy]tetrasulfides could be used. BTSPD was selected for this example because it is readily available. In addition, vinyl functionality was incorporated into the aerogels via the alkoxy silane precursor VTMS (vinyltrimethoxysilane discussed above). Specifically, this example combines using a bridged silsesquioxane, BTSPD, with VTMS to further improve the flexibility and elastic recovery of silica-based aerogels. VTMS and BTSPD are copolymerized with TMOS using a two-step (acid-base) sol-gel synthesis as shown in Scheme 3 below, using ethanol as a solvent.

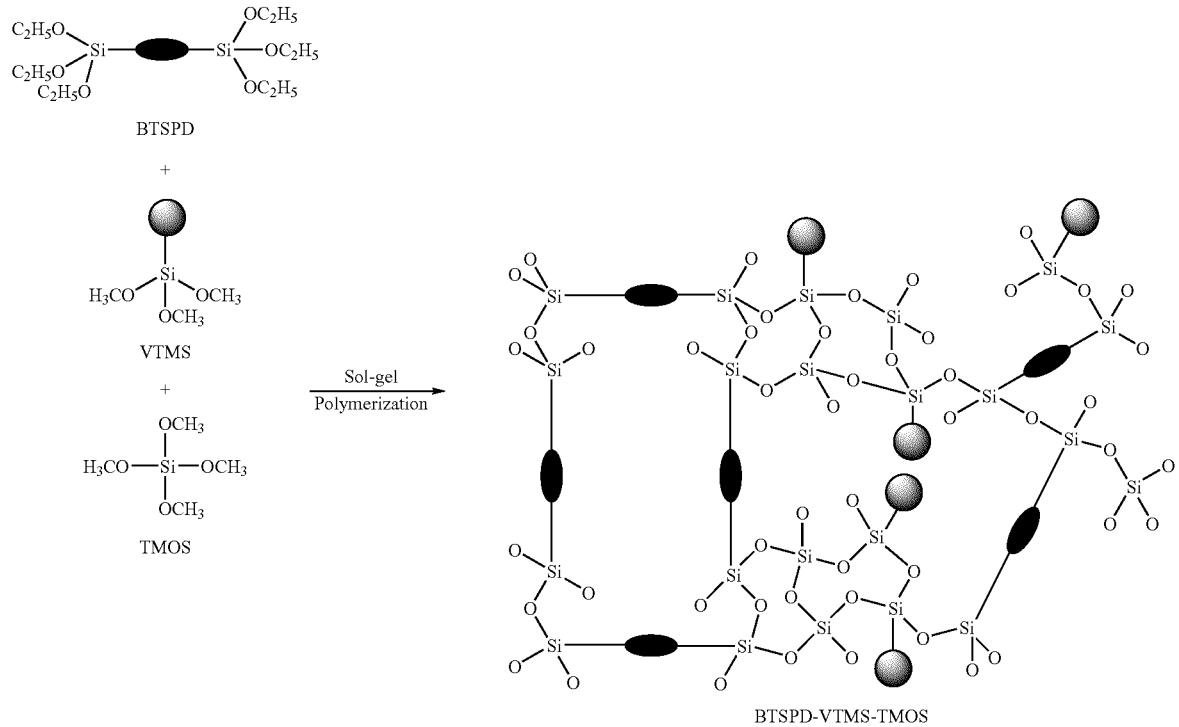

Scheme 3. Formation of Silica network using BTSPD, VTMS and TMOS in a sol-gel process.

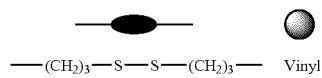
—(CH$_2$)$_3$—S—S—(CH$_2$)$_3$—   Vinyl

Generally used in industry as a coupling agent for elastomers, especially silica-rubber composites, Shea et al., Chem. Mater. 2001, 13, 3306-3319, BTSPD provides a flexible bridging group in the silica structure as shown in Scheme 3, comprised of two propyl units linked by a sulfur-sulfur bond. This bridge acts as organic spacer and a flexible link in the silica network, but is longer than the hexylene bridging group that is produced using BTMSH as a precursor, as described, e.g., in Examples 1 and 3 above. Loy et al., Chem. Rev. 1995, 95, 1431-1442. VTMS, with a hydrophobic vinyl group is similar to MTMS (Example 5) in that only three Si—O bonds are possible for the hydrolysis and condensation reactions to take place. In addition, vinyl, being larger than the methyl group, may alter the pore structure, as well as provide a reactive site for polymer reinforcement. In the present example, statistical experimental design methodology, Montgomery, Design and Analysis of Experiments, 5$^{th}$ Edition, John Wiley and Sons, Inc., Hoboken, N.J., 2001, is applied to illustrate the effects of three variables, concentration of BTSPD, VTMS, and TMOS, on the measured properties of the resulting samples. Measured properties include molecular structure as determined by $^{13}$C and $^{29}$Si nuclear magnetic resonance spectroscopy (NMR), morphology and pore structure as seen by scanning electron microscopy (SEM) and nitrogen adsorption porosimetry, as well as hydrophobicity and mechanical properties of the monoliths.

VTMS and BTSPD were purchased from Gelest, Inc. and TMOS was obtained from Sigma-Aldrich. All reagents were used without further purification. Solutions of 28% NH$_4$OH and concentrated HNO$_3$ were purchased from Fisher Scientific. The concentrated HNO$_3$ was diluted to 2M before use. Solid $^{13}$C and $^{29}$Si NMR spectra of the samples were characterized with a Bruker Avance-300 spectrometer, using cross-polarization and magic angle spinning at 11 KHz. The solid $^{13}$C spectra were externally referenced to the carbonyl of glycine (176.1 relative to tetramethylsilane, TMS) and solid $^{29}$Si spectra were referenced to the silicon peak of sodium salt of 3-trimethylsilylpropionic acid (0 ppm). A Hitachi S-4700 field emission microscope was used for the SEM after sputter coating the specimens with gold. The samples were outgassed at 80° C. for 8 hours under vacuum before running nitrogen-adsorption porosimetry with an ASAP 2000 surface Area/Pore Distribution analyzer (Micromeritics Instrument Corp.) The skeletal density was measured using a Micromeritics Accupyc 1340 helium pycnometer. Supercritical CO$_2$ fluid extraction was performed using an Applied Separations 1-Spe-ed SFE-2 manual system.

Variables used in preparing samples including concentrations of VTMS, BTSPD and TMOS are listed in Table 6 below. The total molar ratio of the nitric acid to total Si was fixed at 0.06:1 and a volume ratio of 2M nitric acid to 28% NH$_4$OH of 1:2 was used. As an example, formulation 20 from Table 6 was synthesized by first combining BTSPD (2.32 ml, 0.2 mol/l), VTMS (0.38 ml, 0.1 mol/l) and TMOS (0.37 ml, 0.1 mol/l) in 20.58 ml ethanol. Nitric acid (0.45 ml of 2M solution) was added to the silane mixture and stirred for half an hour followed by NH$_4$OH (0.9 ml of 28% solution) and another 10 min of stirring at which time the solution became yellow.

The sol was poured into 20 ml polypropylene syringe molds, nominally 2 cm in diameter, prepared by cutting off the needle end of the syringe and extending the plunger all the way out. The extended plunger was then used as the support. The sol formed an opaque gel in 20 minutes and was allowed to age for 24 hours before being extracted into clean ethanol and soaked for another 24 hour period. Ethanol was exchanged three more times at one day intervals to remove the excess water and condensation byproducts.

The washed gels were then placed in a 1 L supercritical fluid extraction chamber, in ethanol. The ethanol was exchanged with liquid CO$_2$ at ~100 Bar and ~25° C. in four 2 hour cycles before heating the liquid CO$_2$ to 45° C. to convert it to a supercritical state. CO$_2$ gas was then slowly vented out at the rate 4.5 L/min from the chamber in three hours to give the dried monoliths with density of 0.09 g/cm$^3$.

Compression tests were performed on cylindrical samples by an Instron 4505 test stand with a 2200 lb load cell running Testworks 4.08 software. The specimens were cut and polished to make sure that the top and bottom surfaces were smooth and parallel. The diameter and length of the specimens were measured before testing. The specimen was compressed up to 25% or 75% of its original length with a compression rate of 0.25 in/min, after which the specimen was unloaded with a rate 2 inch/min back to zero displacement and the process was repeated. After the second compression cycle, the specimen was left for 30 minutes at room temperature, at which time the final length of the sample was measured. The unrecovered strain (%) was calculated as the percentage of the initial length that did not recover. The Young's modulus was taken as the initial slope from the stress strain curve of the first compression.

Contact angle testing was performed on the Ramé-Hart Model 250-00 Standard Gonionmeter, serial number 508171. The image of a drop of distilled water on the polished and level sample surface was captured and analyzed by Drop image Advanced version 1.5.04 software. An average value was obtained from five repeat measurements and is reported in Table 6.

Measured properties from Table 6 were analyzed using Design Expert Version 7.1, available from Stat-Ease, Inc. The silane concentrations were varied with VTMS and BTSPD ranging from 0.1 to 0.3 mol/l, and TMOS ranging from 0.1 to 0.5 mol/l of the total sol. Multiple linear least squares regression was used to derive empirical models to describe the effect of each silane component on measured properties. A full quadratic model including all main effects, second order effects and all two-way interactions was entertained and all variables were orthogonalized (transformed to −1 to +1 scale) before analysis. Terms deemed not to be significant in the model (<90% confidence) were eliminated one at a time using a backwards stepwise regression technique.

Monoliths were fabricated starting with wet gels using a two-step (acid-base) process. In the first step, the silanes are hydrolyzed using nitric acid as catalyst. In the second step, ammonium hydroxide is added to promote condensation and formation of a continuous gel network. Preliminary work found that sturdy gels were formed only when the acid to base volume ratio is 1:2. At higher ratio of acid to base, gelation did not take place while at lower ratio, settling of particles is observed. Monoliths were made using concentrations of VTMS and BTSPD varied from 0.1 to 0.3 mol/l and TMOS varied from 0.1 to 0.5 mol/l. The formulations along with measured properties are shown in Table 6.

incomplete hydrolysis of BTSPD and are seen in all the samples. The very small peak at 50.6 ppm can be assigned to the methoxy groups attached to Si due to incomplete hydrolysis of TMOS and VTMS.

TABLE 6

Preparation conditions and measured properties of monoliths in Example 6.[a]

| # | VTMS (mol/l) | BTSPD (mol/l) | TMOS (mol/l) | Density (g/cm³) | Porosity % | Modulus (MPa) | Unrecovered strain, % | Surface Area (m²/g) | Contact Angle (°) |
|---|---|---|---|---|---|---|---|---|---|
| 1 | 0.1 | 0.1 | 0.5 | 0.126 | 91.6 | 0.50 | 11.9 | 656 | 129 |
| 2 | 0.2 | 0.1 | 0.5 | 0.137 | 90.6 | 0.72 | 8.05 | 718 | 129 |
| 3 | 0.3 | 0.1 | 0.5 | 0.185 | 87.7 | 2.29 | 1.2 | 598 | 132 |
| 4 | 0.1 | 0.2 | 0.5 | 0.153 | 89.6 | 1.35 | 1.2 | 461 | 130 |
| 5 | 0.2 | 0.2 | 0.5 | 0.170 | 88.7 | 1.36 | 1.3 | 416 | 137 |
| 6 | 0.3 | 0.2 | 0.5 | 0.194 | 86.6 | 1.78 | 1.7 | 439 | 137 |
| 7 | 0.1 | 0.3 | 0.5 | 0.212 | 85.8 | 3.72 | 1 | 308 | 137 |
| 8 | 0.2 | 0.3 | 0.5 | 0.248 | 83.2 | 3.16 | 1.6 | 295 | 141 |
| 9 | 0.3 | 0.3 | 0.5 | 0.257 | 82.4 | 4.65 | 1.2 | 347 | 143 |
| 10 | 0.1 | 0.1 | 0.25 | 0.088 | 93.5 | 0.03 | 9.1 | 218 | 122 |
| 11 | 0.2 | 0.1 | 0.25 | 0.115 | 91.8 | 0.12 | 4.2 | 240 | 128 |
| 12 | 0.3 | 0.1 | 0.25 | 0.142 | 89.7 | 0.30 | 4.3 | 276 | 135 |
| 13 | 0.1 | 0.2 | 0.25 | 0.118 | 91.5 | 0.24 | 0.8 | 48.7 | 134 |
| 14 | 0.2 | 0.2 | 0.25 | 0.140 | 89.7 | 0.46 | 1.7 | 68.2 | 135 |
| 15 | 0.3 | 0.2 | 0.25 | 0.180 | 87.0 | 0.86 | 0.7 | 97.2 | 135 |
| 16 | 0.1 | 0.3 | 0.25 | 0.163 | 88.1 | 0.99 | 1.3 | 95.0 | 131 |
| 17 | 0.2 | 0.3 | 0.25 | 0.182 | 86.7 | 2.28 | 0.9 | 100 | 136 |
| 18 | 0.3 | 0.3 | 0.25 | 0.227 | 83.5 | 3.71 | 1 | 139 | 138 |
| 19 | 0.3 | 0.1 | 0.1 | 0.067 | 94.8 | b | b | 3.42 | b |
| 20 | 0.1 | 0.2 | 0.1 | 0.091 | 93.3 | 0.01 | 0 (75%) | 6.56 | 125 |
| 21 | 0.2 | 0.2 | 0.1 | 0.097 | 93.0 | 0.06 | 0.2 | 20.8 | 129 |
| 22 | 0.3 | 0.2 | 0.1 | 0.117 | 91.5 | 0.19 | 0.2 | 34.6 | 143 |
| 23 | 0.1 | 0.3 | 0.1 | 0.187 | 86.5 | 0.36 | 1.2 | 51.4 | 133 |
| 24 | 0.2 | 0.3 | 0.1 | 0.167 | 87.2 | 0.92 | 2.5 | 64.6 | 134 |
| 25 | 0.3 | 0.3 | 0.1 | 0.189 | 86.0 | 2.07 | 2.8 | 69.6 | 143 |

Figure 26:
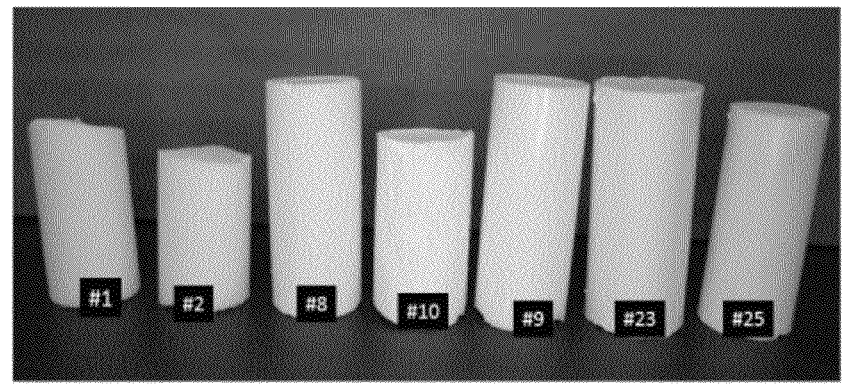
FIG. 26 shows a photo of representative samples of monoliths (from Table 6) prepared in accordance with Example 6.

[a]Combinations of 0.1 mol/l and 0.2 mol/l VTMS, with 0.1 BTSPD and 0.1 mol/l TMOS did not gel and thus are not reported.
[b]Formulation too fragile to test Combinations of 0.1 BTSPD and 0.1 mol/l TMOS with 0.1 and 0.2 mol/l VTMS did not gel. In addition, monoliths from the formulation labeled as 19 in Table 6 using the same amount of BTSPD and TMOS with 0.3 mol/l VTMS were too fragile for compression testing and contact angle measurements. Shown in FIG. 26 is a picture of representative samples from this example. All monoliths produced were white and opaque. Shrinkage occurring over the whole fabrication process, measured as the difference between the diameter of the mold and the dried monolith, was fairly uniform across this example, ranging between 10 to 20%.

Figure 27:
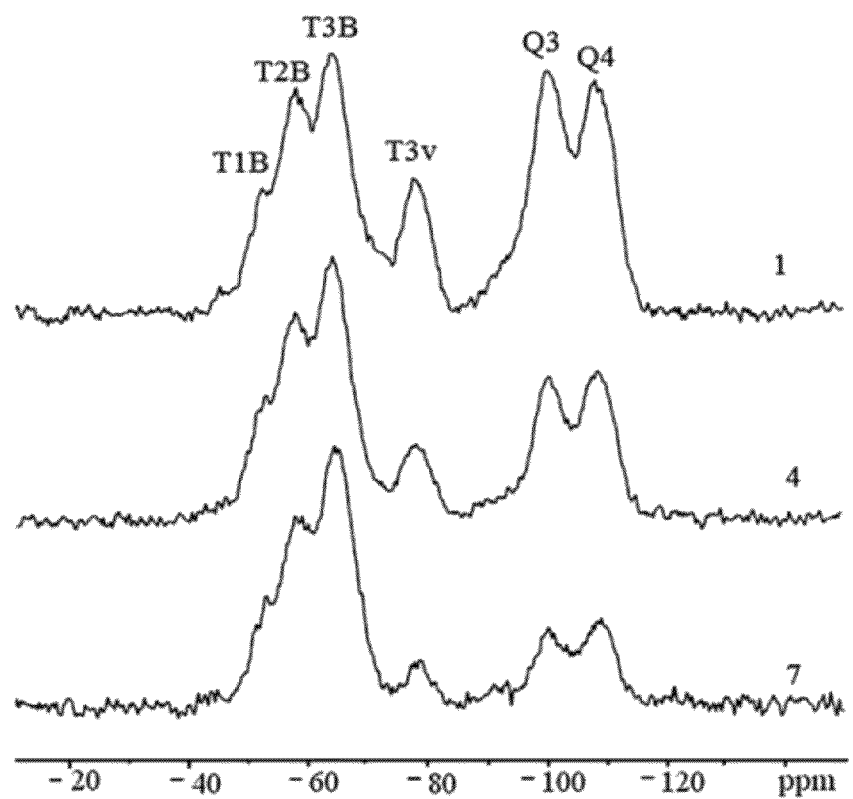
FIG. 27 shows solid CP-MAS $^{29}$Si NMR spectra of samples 1, 4 and 7 from Table 6 prepared in accordance with Example 6.

All monoliths from this example were characterized using solid $^{29}$Si and $^{13}$C NMR spectra. FIG. 27 shows $^{29}$Si NMR spectra of samples 1, 4 and 7 from Table 6, which were made with increasing levels of BTSPD concentration but with VTMS and TMOS concentration held constant. Generally, in TMOS derived monoliths, two peaks assigned to silanol (Q3, −99 ppm) and siloxane (Q4, −108.8 ppm) can be found in the $^{29}$Si NMR spectrum. The peak at −66.4 ppm (T3B) can be assigned to the fully reacted tridentate Si of BTSPD. The peaks of −59.5 ppm (T2B) and −53.4 ppm (T1B) correspond to the di- and monodentate Si of BTSPD. The peak at −80.4 ppm is attributed to the fully reacted VTMS Si (T3V). As expected, the relative intensity of the bands corresponding to TMOS and vinyl decrease with increasing amount of BTSPD.

Figure 28:
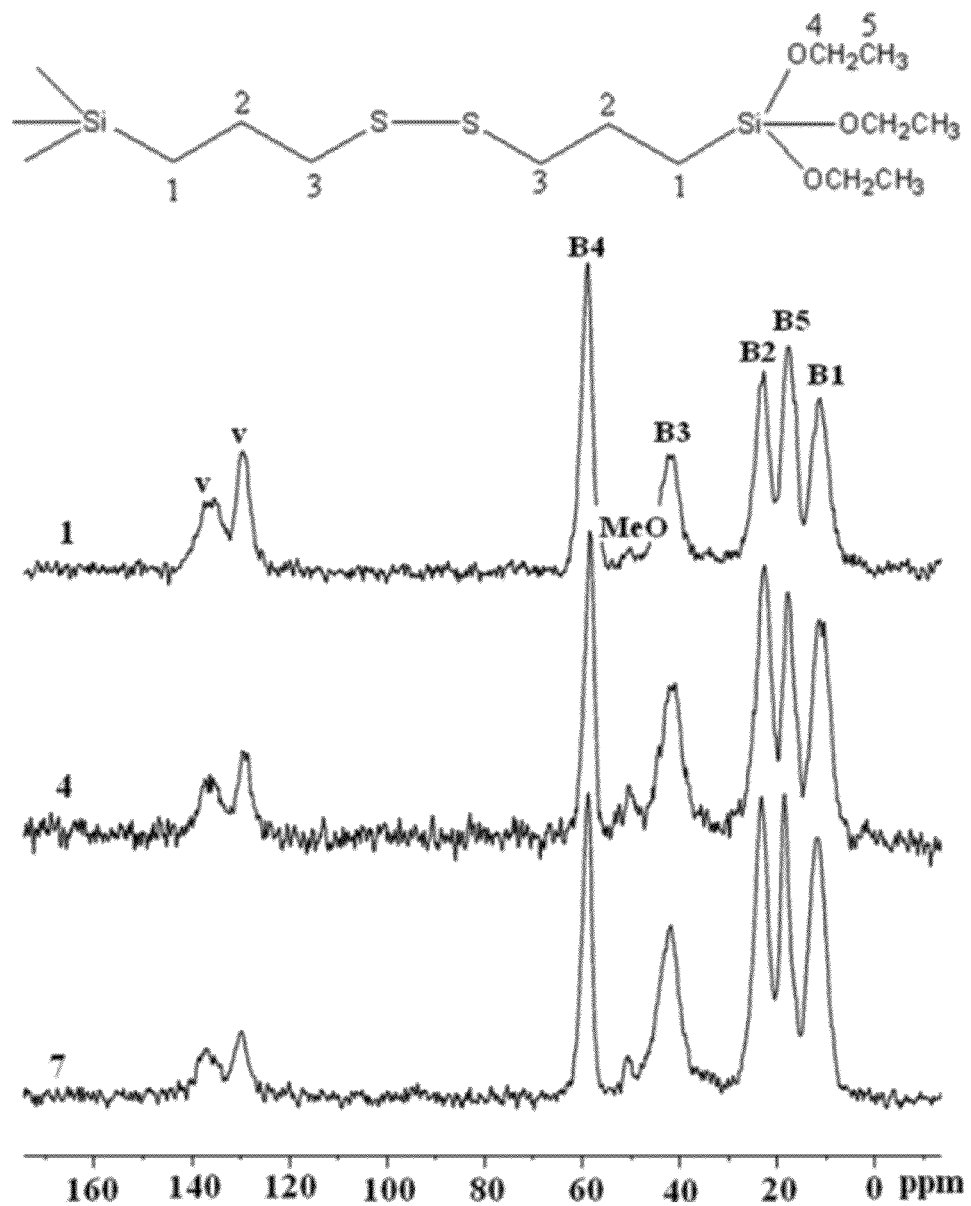
FIG. 28 shows solid CP-MAS $^{13}$C NMR spectra of samples 1, 4 and 7 from Table 6 prepared in accordance with Example 6.
Figure 29:
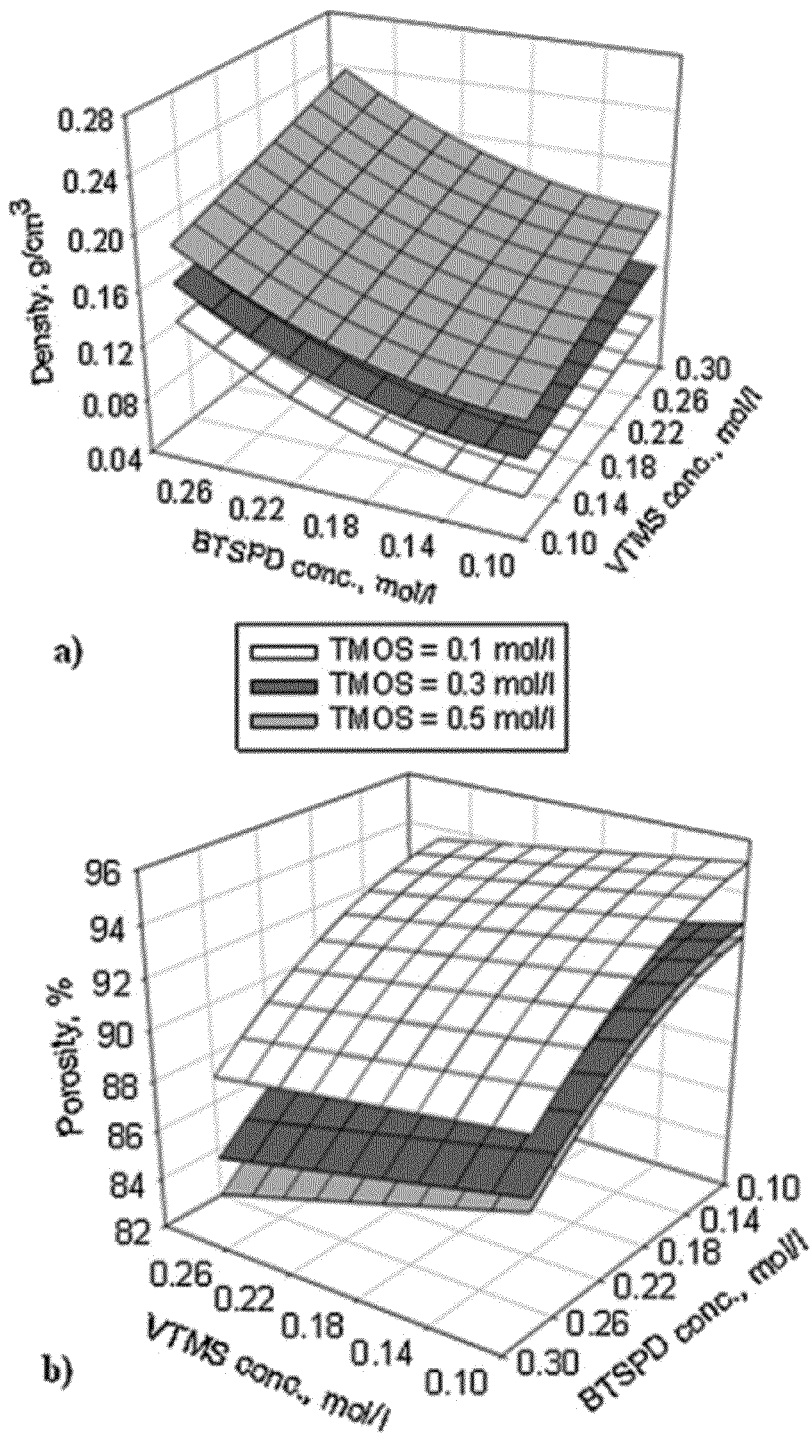
FIG. 29 illustrates empirical models for a) density and b) porosity plotted vs. BTSPD and VTMS concentration at three levels of TMOS used to prepare silica aerogels in accordance with Example 6.

Solid $^{13}$C spectra of the same monoliths are shown in FIG. 28, confirming the presence of the propyl groups derived from BTSPD with peaks at 10.8 ppm, 22.3 ppm and 40.9 ppm. The carbon peaks of the vinyl group from VTMS appear at 129.8 ppm and 136.0 ppm. Additional peaks at 17.9 ppm and 57.8 ppm can be assigned to ethoxy groups attached to Si due to incomplete hydrolysis of BTSPD and are seen in all the The bulk density of the monoliths in this example ranged from 0.067 to 0.257 g/cm3. A graph of the empirical model for density (standard deviation=0.015 g/cm³, $R^2$=0.93) derived by multiple linear regression analysis of the raw data is shown in FIG. 29a graphed vs. VTMS and BTSPD concentration for three levels of TMOS concentration. As one would expect, density increases with increasing concentrations of VTMS, BTSPD and TMOS. Increasing silane concentration in general increases the amount of silica in the monolith while increasing VTMS and BTSPD also causes an increase in the amount of organic pendant or bridging groups found in the monoliths. Hence, BTSPD concentration has the largest effect on density because it contains the largest bridging organic group and contributes two Si groups.

The bulk density ($\rho_b$) and the skeletal density ($\rho_s$) obtained from helium pycnometry measurements were used to calculate porosity from the following equation, Porosity=$(1-\rho b/\rho s) \times 100\%$ The calculated porosities of the samples ranged from 82% to 95%. In FIG. 29b is shown a graph of the empirical model for porosity (standard deviation=1.02%, $R^2$=0.93). As expected, porosity decreases with increasing amounts of silane precursors, in opposition to density (the more solid phase, the less porosity.) BTSPD again has the largest effect by contributing both increased amount of Si and organic to the monoliths.

The surface areas and pore volume of the monoliths were measured by nitrogen sorption using the Branuaer-Emmet-Teller (BET) method. Typical nitrogen adsorption and desorption isotherms at 77 K for a sampling of monoliths were shown in FIG. 30a. The adsorption isotherms are an IUPAC type IV curve with an H1 hysteresis loop, indicating that the monoliths consist predominately of three dimensional continuous meso-macropores. When the total silane amount of BTSPD and VTMS is greater than that of TMOS (as in sample 23), plateaus at high relative pressure (P/P$_0$) were observed, indicating the modification of the pore structures of the organic groups derived from BTSPD and VTMS.

Figure 30:
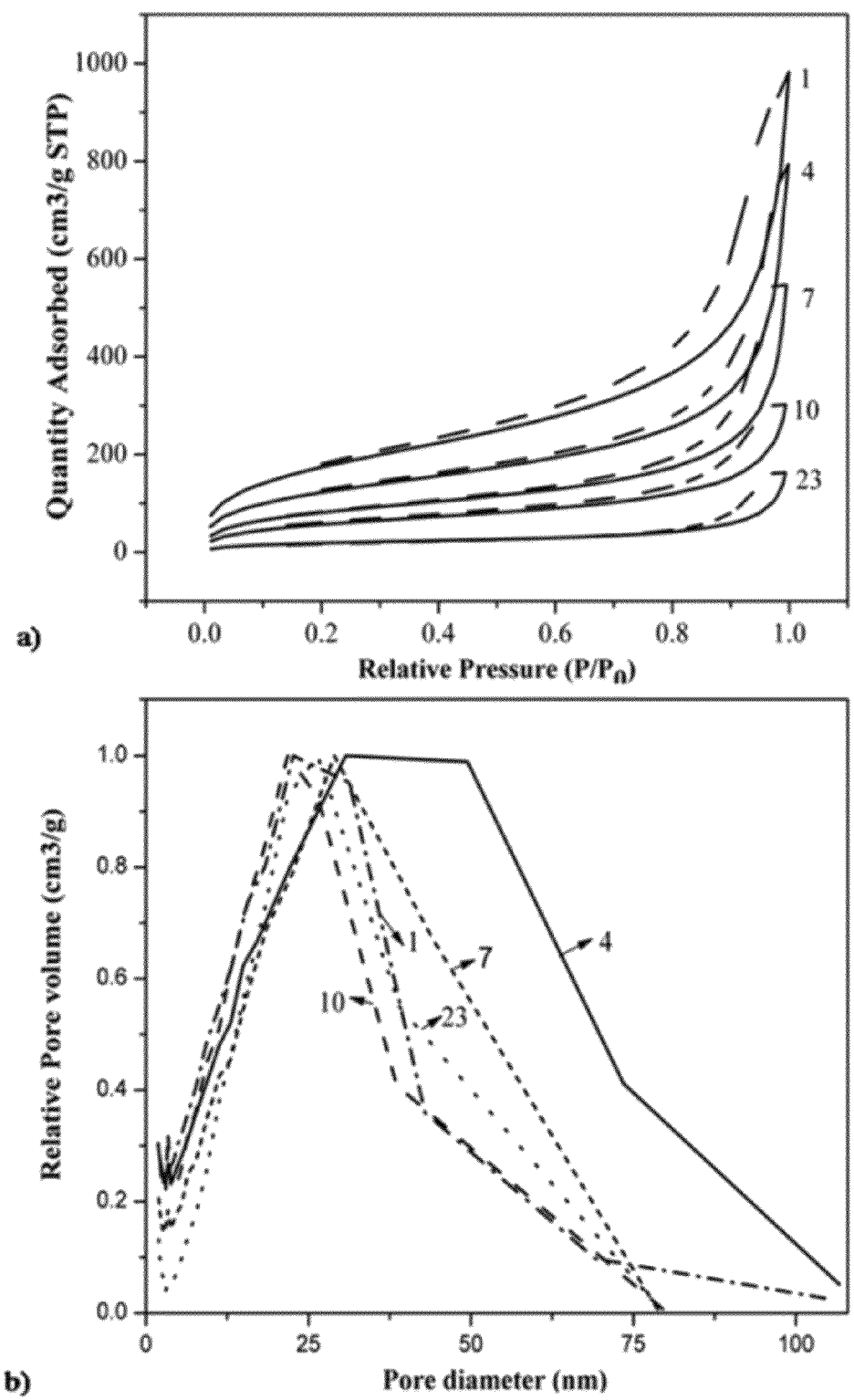
FIG. 30 illustrates a) typical $N_2$ adsorption-desorption isotherms (at 77 K), and b) plots of relative pore volume-pore diameter of samples 1, 4, 7, 10 and 23 from Table 6 prepared in accordance with Example 6.

A graph of relative pore volume vs. pore diameter is shown in FIG. 30b for the same samples. According to IUPAC definition, pores are classified by the pore diameter, micropores have diameters less than 2 nm; mesopores have diameters between 2 and 50 nm. Macropores have pore diameters larger than 50 nm. From FIG. 30b, it can be seen all the samples have both mesopores and macropores, but very few in the micropore size region. For samples with extremely low surface area, sample 19 and 20, no adsorption and desorption isotherm curves can be obtained, indicating loss of mesoporosity.

Figure 31:
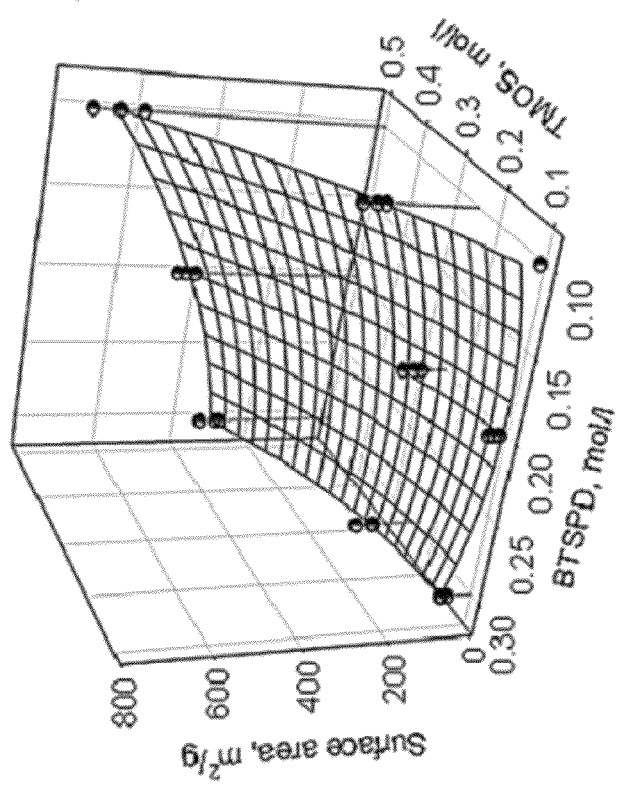
FIG. 31 is a graph of an empirical model for surface area vs. BTSPD and TMOS concentration shown with raw data based on compositions of silica aerogels prepared in accordance with Example 6. Note that VTMS is not a significant factor in the model over and above random error.

The surface areas range from 3 m$^2$/g to as much as 720 m$^2$/g across this example. The empirical model for surface area (standard deviation=34.8 m$^2$/g, R$^2$=0.98) is shown in FIG. 31. As seen in FIG. 31, increasing TMOS concentration significantly increases surface area. However, increasing BTSPD, especially when TMOS concentration is high, causes a decrease in surface area. In fact, when TMOS concentration is at 0.5 mol/l, surface areas drop by half going from low to high BTSPD concentrations (from over 700 m$^2$/g to 350 m$^2$/g). At 0.1 mol/l TMOS, BTSPD concentration has less of an effect on surface areas. In these cases, all surface areas were small, ranging from 3 m$^2$/g to 70 m$^2$/g for all the samples, noting that as previously mentioned, at the lowest setting of TMOS and BTSPD, only the formulation with VTMS at 0.3 mol/l was able to be produced. Also note that VTMS has no significant effect on surface area over and above random error.

The loss of the mesoporosity with increasing amount of BTSPD, as evidenced by BET surface area, is similar to results seen using BTMSH in combination with TMOS and VTMS in styrene reinforced aerogels and in combination with TEOS and APTES in epoxy reinforced aerogels. In those studies, however, raising APTES and VTMS concentration did contribute to lowering the surface areas, perhaps more due to the increased polymer cross-linking with the presence of more reactive sites. In this case, since the gels have not been reacted further with polymer, we do not see this effect.

Figure 32:
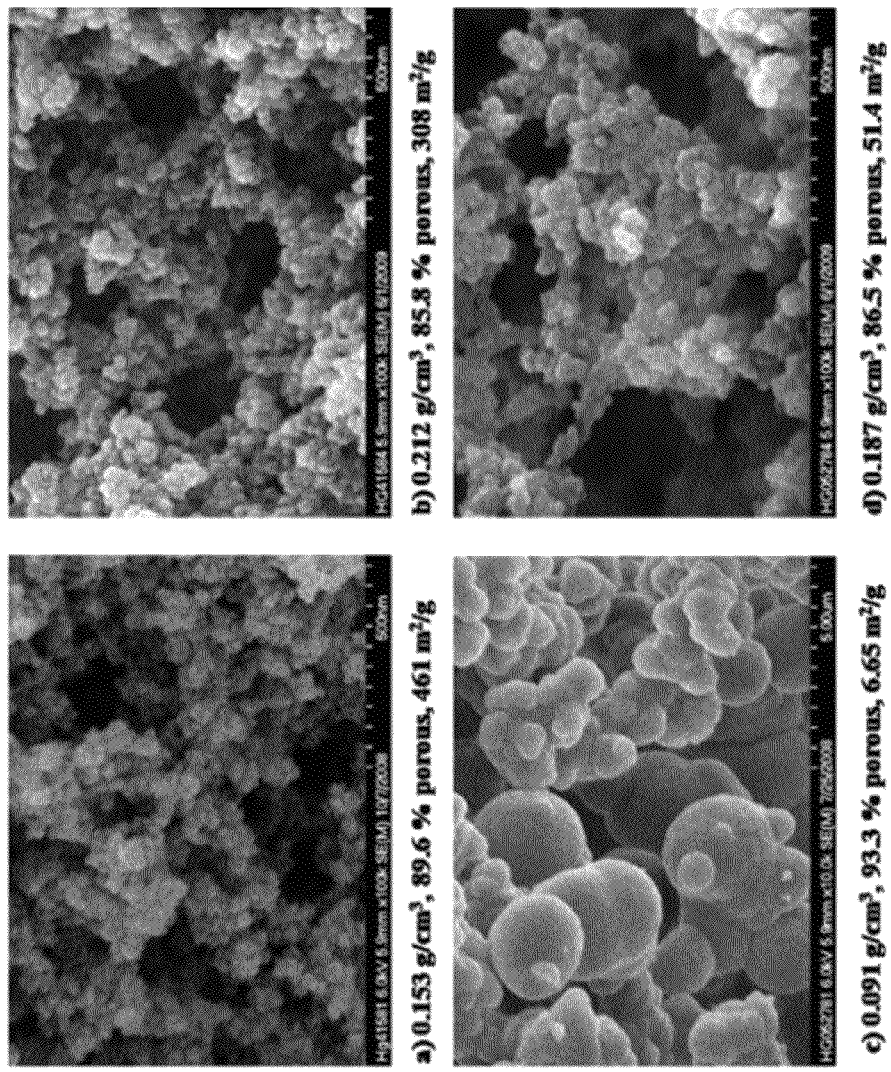
FIG. 32 shows scanning electron micrographs of the following samples from Table 6 prepared in accordance with Example 6: a) sample 4 (0.2 mol/l BTSPD) and b) sample 7 (0.3 mol/l BTSDP) made using 0.5 mol/l TMOS, compared to samples made with 0.1 mol/l TMOS: c) sample 20 (0.2 mol/l BTSPD) and d) sample 23 (0.3 mol/l BTSPD).

The difference in nanostructure can also be seen by scanning electron micrographs (SEM) as shown in FIG. 32. For the aerogels made using high concentrations of TMOS (0.5/mol/l), higher BTSPD concentration leads to larger particle sizes and larger pores. Hence, the surface area is decreased. SEM of samples 4 (FIG. 32a) and 7 (FIG. 32b) both produced using 0.5 mol/l of TMOS, reveal a typical aerogel morphology with a fine distribution of uniformly small particles. Iler, *The Chemistry of Silica*, Wiley, New York, 1979. However, the pore structure of the monoliths shown in FIG. 32a made using 0.2 mol/l BTSPD and that shown in FIG. 32b made using 0.3 mol/l BTSPD have a wide distribution of pore sizes ranging from 10 nm to 200 nm. This effect on pore structure due to incorporating an organic linking group into the silica backbone is again the same as that observed with increasing BTMSH in the epoxy reinforced aerogels previously studied. Decreasing the concentration of TMOS to 0.1 mol/l leads to larger pore diameters as shown in the micrographs of sample 20 (FIG. 32c) and sample 23 (FIG. 32d). However, at the lowest TMOS concentration, when decreasing BTSPD amount from 0.3 mol/l to 0.2 mol/l, the particle size increases from 50 nm (FIG. 32d) to 1-2.5 μm (FIG. 32c) noting that these micrographs are shown at a different scale.

The difference in the nanostructure (surface area, pore size, morphology) due to increasing amounts of BTSPD probably arises from solubility differences of the siloxy precursors in the ethanol/water mixture used to produce the gels. Ethanol solvates the siloxy groups leading to a well dispersed array of small particles and pores when more TMOS is used. The aliphatic groups are not as soluble in the aqueous ethanol, leading to more phase separation in the gel, larger particle sizes and a collapse of the mesoporosity.

Figure 33:
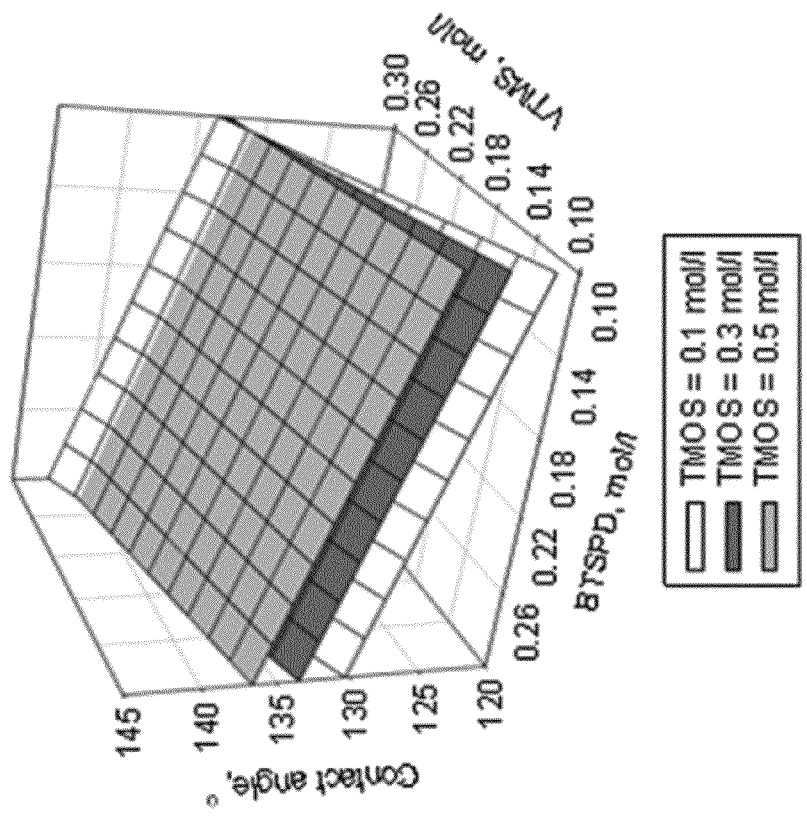
FIG. 33 is a graph of an empirical model for water contact angle vs. BTSPD and VTMS concentration at three levels of TMOS concentration used to prepare silica aerogels in accordance with Example 6.

Contact angles of the monoliths prepared in accordance with this example were measured using a distilled water droplet. All samples are relatively hydrophobic with contact angles of at least 120°. As shown in FIG. 33 in the empirically derived model for water contact angle (standard error=2.65°, R$^2$=0.81), hydrophobicity increases with increasing BTSPD, TMOS and VTMS concentration, with the greatest effect being due to VTMS which covers the silica surface with hydrophobic vinyl groups. At high VTMS concentration, TMOS concentration has no effect on measured contact angles, while at low VTMS, decreasing TMOS concentration decreases the contact angle. This may be due to the larger pore sizes associated with lower concentrations of TMOS, which provide pathways for the water droplets to be absorbed. Increasing BTSPD concentration also increases the measured contact angle, even though increasing BTSPD concentration also increases pore size. However, BTSPD also contributes hydrophobic propyl groups to the silica skeleton which may counter the effect of pore size in the same way that high vinyl concentration counters the effect of TMOS concentration. The highest contact angles measured in this example (143°) are for monoliths containing the highest levels of BTSPD and VTMS, regardless of TMOS concentration.

Figure 34:
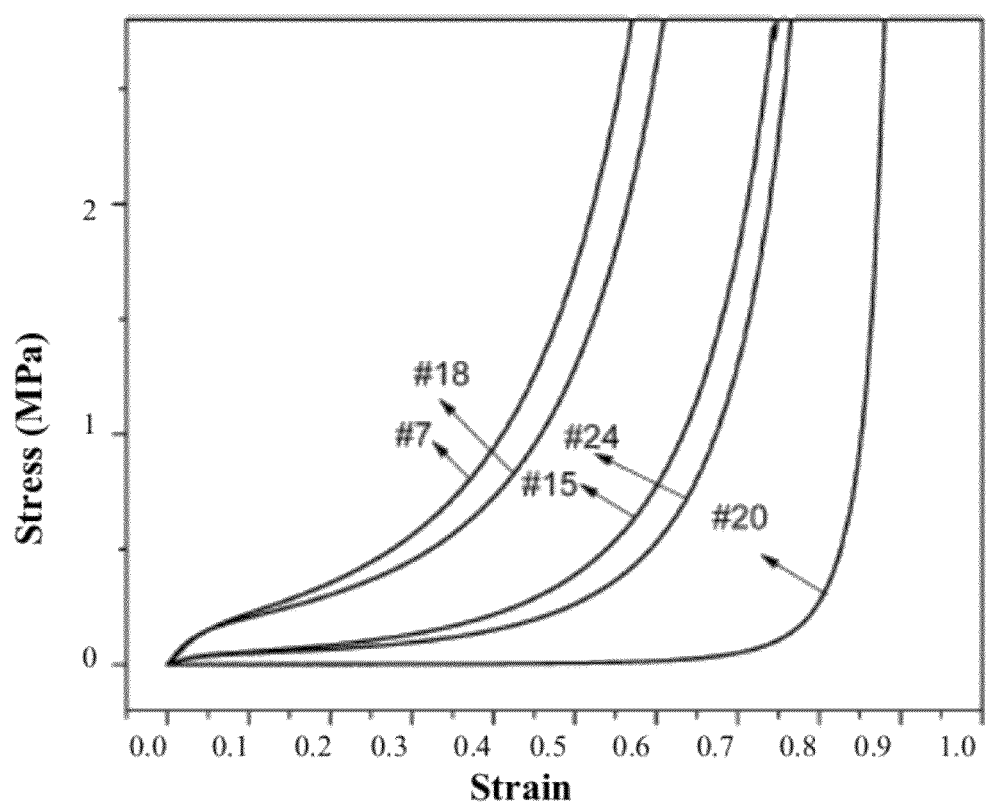
FIG. 34 shows typical stress strain curve of samples 7, 15, 18, 20 and 24 from Table 6 prepared in accordance with Example 6, having different modulus.
Figure 35:
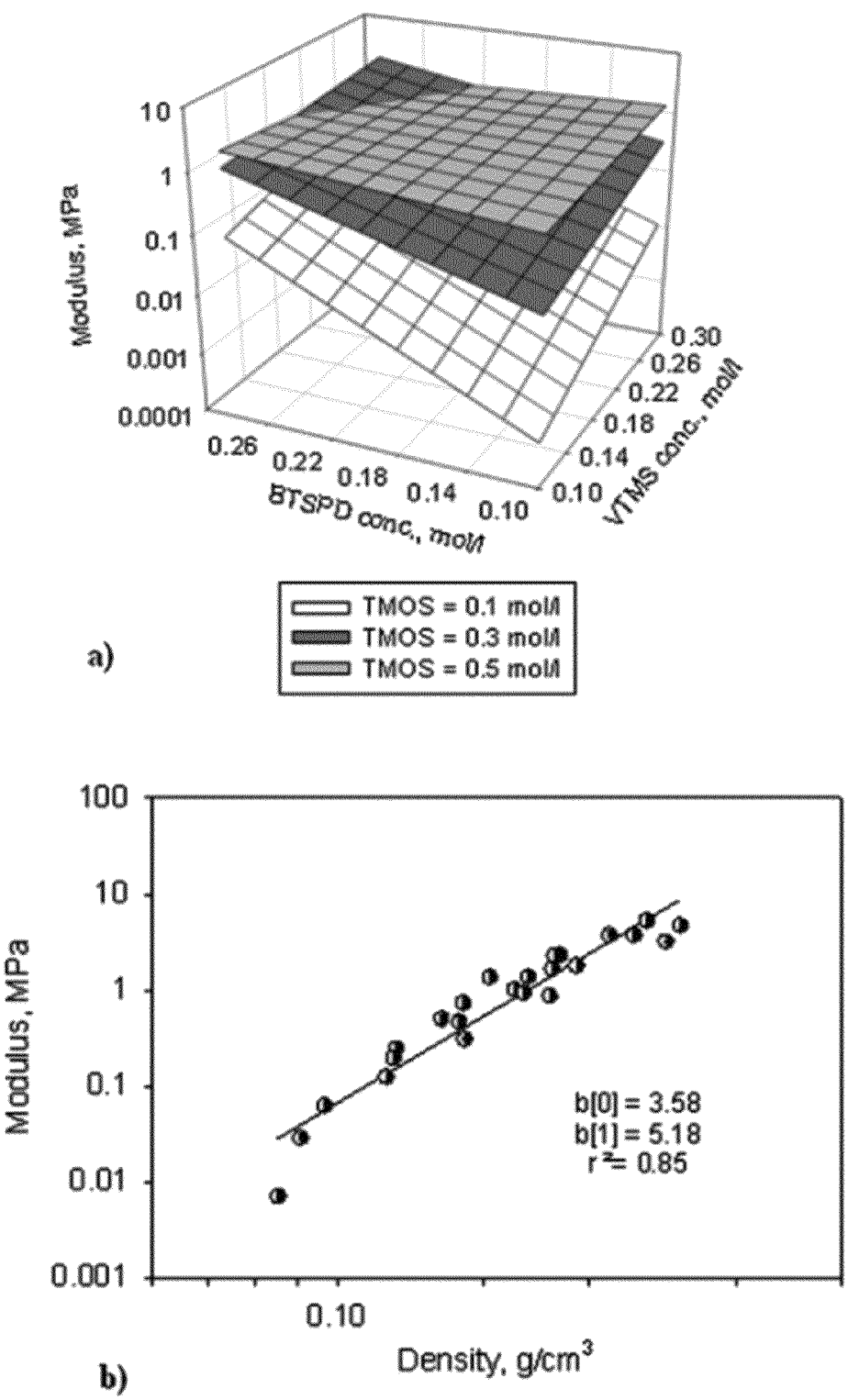
FIG. 35 shows graphs of a) an empirical model for compressive modulus vs. BTSPD and VTMS concentration based on compositions of silica aerogels prepared in accordance with Example 6, and b) power law relationship between density and modulus for those compositions.

Compression tests were run on all monoliths from Table 6, except sample 19, since this formulation was very fragile. Typical stress strain curves from selected samples produced in this example are shown in FIG. 34. Young's modulus taken from the initial slope of the stress strain curve was modeled using multiple linear regression analysis. Graphs of the empirical model for Young's modulus (log transformed before analysis, standard error=0.33, R$^2$=0.97) are shown in FIG. 35a. It is evident from the graph that TMOS concentration has the largest effect on modulus, with modulus increasing with increasing TMOS concentration. In fact, at high TMOS concentration, there is very little effect of VTMS or BTSPD concentration on modulus (the response surface is very flat). At lower concentrations of TMOS, modulus is seen to increase with increasing BTSPD and VTMS concentration, in response to a greater change in density over the range of samples.

The power law relationship between density and modulus is graphed in FIG. 35b with an exponent b (1) of 5.18 (R$^2$=0.85) similar to that reported for styrene reinforced aerogels derived from TMOS, VTMS and BTMSH. Power law relationships between modulus and density for native silica aerogels (TMOS or TEOS alone) are typically reported with an exponent of 3 to 3.7 depending of the synthesis route, Pekala et al. *Mater. Res. Soc. Symp. Proc.* 1991, 207, 197-200, and have been shown to depend most on the connectivity between particles. Woigner et al. *J. Non-Cryst. Solids* 1998, 241, 45-52. The greater increase in the exponent for aerogels made using a mixture of TMOS, VTMS and organically linked bis(alkoxysilanes) is most likely due to molecular structure variations possible with these systems which contribute to differences in the skeletal structures that are observed by SEM.

Figure 36:
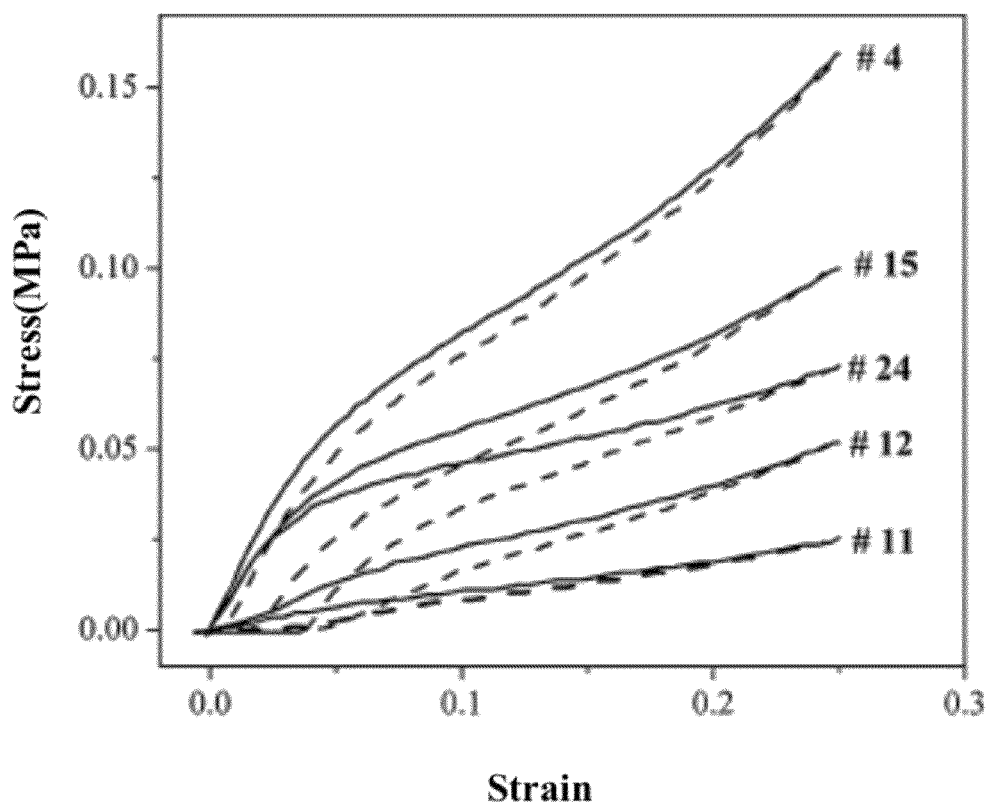
FIG. 36 shows stress strain curves from tests of a variety of monoliths from Example 6 (referring to sample numbers from Table 6) compressed to 25% strain twice (solid line: first compression; dashed line: second compression).

To assess the elastic recovery of the monoliths from this example, repeat compression tests were performed where the samples were compressed to 25% strain twice and allowed to recover for thirty minutes. Typical stress strain curves for repeat compression tests are shown in FIG. 36 for a variety of samples of differing modulus. In each case, the solid line is the first compression and the dashed line is the second compression. The closer the two lines overlap, the better the recovery. The unrecovered strains reported in Table 6 are calculated as the difference between their final and initial length 30 minutes after the second compression to 25% strain. After 30 minutes, no change is observed in the final length. With few exceptions, the monoliths reported in Table 6 exhibited not more than 3% unrecovered strain following the two cyclic compressions 30 minutes after the force from the second compression was removed.

Figure 37:
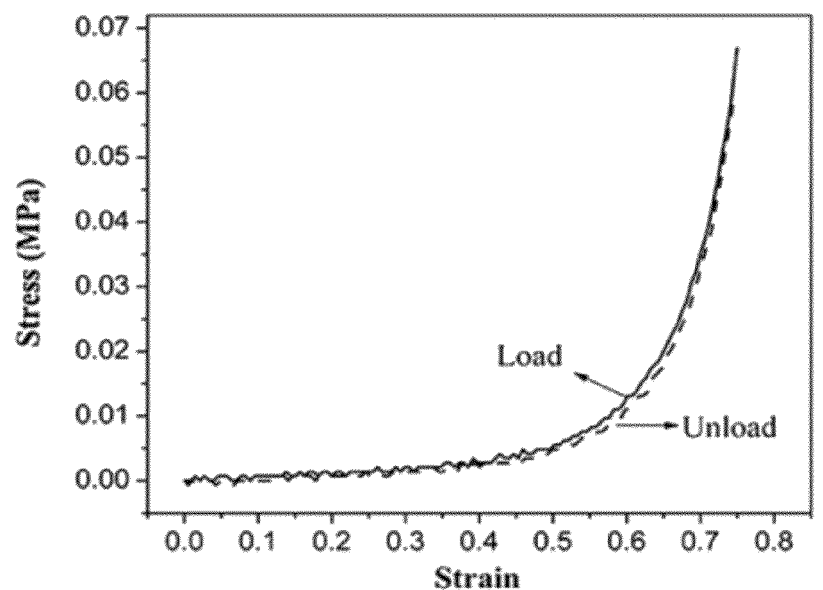
FIG. 37 shows a) stress strain curves of sample 20 from Table 6 prepared in accordance with Example 6 compressed to 75% strain twice (solid line: first compression; dashed line: second compression); b) the same sample 20 compressed by finger pressure demonstrating full recovery; c) recovery after compression of the same sample 20 vs. time.
Figure 37:
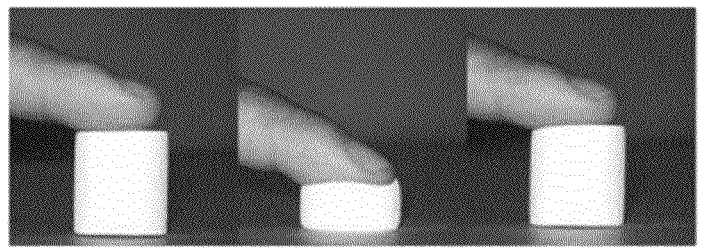
Figure 37:
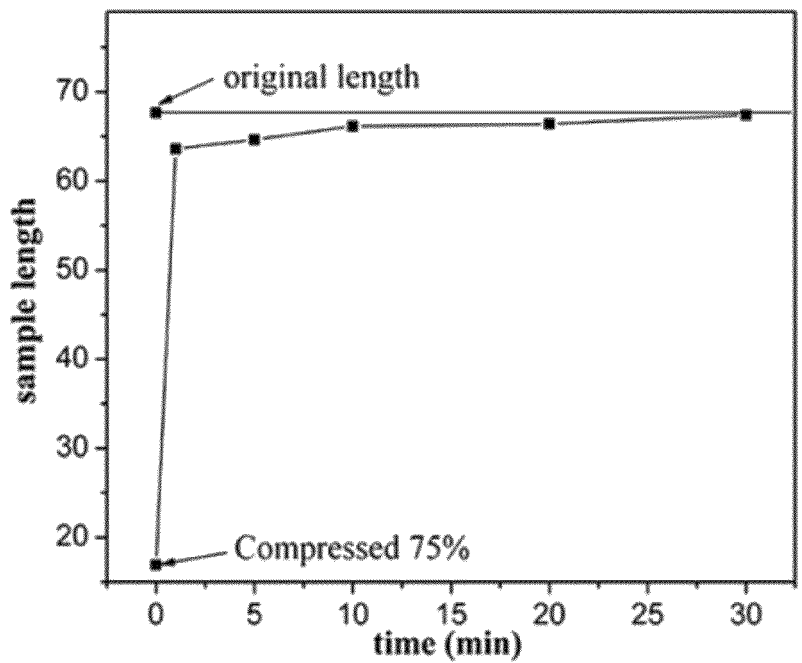

All of the monoliths in this example with BTSPD concentration of at least 0.2 mol/l exhibit low unrecovered strain (or high elastic recovery). The best recovery after compression is from samples made using formulation 20 in Table 6 (0.1 mol/l TMOS, 0.2 mol/l BTSPD and 0.1 mol/l VTMS). This sample recovers almost completely even after compressing to 75% strain as illustrated in the stress strain curve in FIG. 37a. FIG. 37b shows a sample of 20 before, during and after compressing the sample with finger pressure. As seen in FIG. 36c, sample 20 recovers 98% of their original length during the first ten minutes after compression. After thirty minutes, the recovery is 99.6%.

Figure 38:
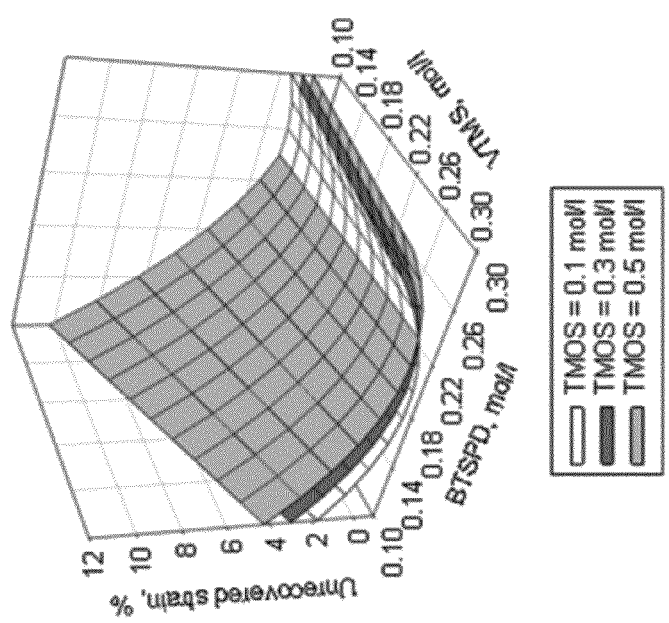
FIG. 38 shows an empirical model for unrecovered strain vs. BTSPD and VTMS concentration used to prepare silica aerogels in accordance with Example 6.

A graph of the empirical model for unrecovered strain is shown in FIG. 38, illustrating that BTSPD concentration has the largest effect on elastic recovery. Unrecovered strain greatly decreases with increasing BTSPD concentration, reaching an optimum (highest recovery) at about 0.21-0.25 mol/l BTSPD depending on TMOS concentration. Increasing TMOS concentration slightly increases unrecovered strain, when BTSPD concentration is lower. Increasing VTMS concentration also decreases unrecovered strain (increases recovery) when BTSPD concentration is low. This is expected since it has a similar structure to MTMS (three siloxy bonding sites and an unreactive aliphatic group). MTMS derived aerogels are highly flexible and recover from compression (vide supra). Surprisingly, increasing VTMS concentration does not improve elastic recovery when BTSPD is at a higher concentration, suggesting that including bis(alkoxysilanes) linked with organic groups is a more effective way to introduce elastic recovery to the aerogels.

At the optimum BTSPD concentration, elastic recovery is good (unrecovered strain is low) for all levels of TMOS concentration. This is an important finding since there is a trade off in some properties when using BTSPD (e.g., extremely low BET surface areas which are a strong predictor for insulation quality). However, good recovery in formulations with both high TMOS concentration and optimum BTSPD means that it is possible to make stronger aerogels with a combination of higher modulus, good recovery, high BET surface areas and good hydrophobicity. In fact, as predicted by the model, a combination of 0.5 mol/l TMOS, 0.3 mol/l VTMS concentration, and 0.22 mol/l BTSPD should lead to optimized aerogels with a density of 0.21 g/cm3, porosity of 85.5%, Young's modulus of 2.1 MPa, a water contact angle of 138° and near complete recovery after compression (1.3% unrecovered strain). Using this combination of silanes, an authentic aerogel sample was synthesized and measured to have density 0.20 g/cm$^3$, porosity of 85.3%, Young's modulus of 2.4 MPa, 1.4% unrecovered strain after compression to 25% strain and water contact angle of 142°, all in good agreement with the model prediction.

In summary, this example presents a new series of porous, hydrophobic materials consisting of silica linked with organic bridges and vinyl surface groups. The vinyl groups render the monoliths hydrophobic, with water contact angles comparable to that seen for aerogels fabricated from 100% MTMS. Unlike MTMS, however, VTMS does not improve the elastic recovery of the aerogels as much when used in combination with other silanes. The organic linking groups from BTSPD are more effective at improving elastic behaviour, allowing the monoliths to recover nearly completely after compression. Using statistical experimental design methodology and empirical modelling, the concentrations of BTSPD, VTMS and TMOS were varied in the production of the monoliths and found to also have a significant effect on their bulk density, porosity, and BET surface areas. Increasing TMOS concentration significantly increases surface area and Young's modulus while utilizing too high a concentration of BTSPD causes a collapse of the gel structure, greatly reducing mesoporosity and surface area. Aerogels produced using optimum BTSPD concentrations lead to excellent elastic recovery for all levels of TMOS concentration, making it possible to design an aerogel with a combination of high strength, high surface area and good elastic recovery. Reinforcing the aerogel structure by co-reacting styrene or other -ene moieties with the surface vinyl groups supplied by VTMS may provide even higher strengths, analogous to other polymer reinforced aerogels.

As the above Examples demonstrate, the silica aerogels (and the corresponding wet gels) exhibit various physical properties (e.g., elastic modulus) that can be tuned through judicious selection of appropriate starting concentrations of the silane species used to synthesize the gels. In addition, the degree of additional strength and aerogel density can be varied by the degree of polymer cross-linking, which in turn may be regulated by the concentration of non-native functional groups incorporated at the secondary-particle surfaces as cross-link anchors, depending on the selected cross-linking chemistry. Based on the foregoing teachings, a person of ordinary skill in the art will be led to numerous alternative embodiments not expressly disclosed herein but which fall within the scope of the invention and the present teachings. For example, it is expected that other aerogels besides those based on silica could be used, with flexible versions thereof prepared according to analogous methods as those disclosed herein. In addition, alternative flexible linkages may be selected, having varying degrees of chain length, functionality, etc., all of which may be used to tune the degree of flexibility or other desirable properties of a finished aerogel. The concentrations of the silane starting materials (both functionalized and unfunctionalized ceramic oxide precursors, as well as the flex link precursor species) also can be varied to achieve varying degrees of resulting physical properties. It is also contemplated that multiple (i.e. more than one) species of flex link precursor species may be incorporated, which will introduce flexible linkages of different chemistry and structure. These and other variations from the embodiments disclosed herein will be apparent to the person having ordinary skill in the art.

Although the hereinabove described embodiments of the invention constitute the preferred embodiments, it should be understood that modifications can be made thereto without departing from the scope of the invention as set forth in the appended claims.

What is claimed is:
1. A ceramic-oxide network comprising:
 (a) the structure -M-L-M-, wherein:
  M is a metallic or semi-metallic element common to the ceramic-oxide network; and

L comprises a linkage between the opposing M atoms in said structure, L having the form —[X(R²)₂]ₙ—, wherein:
X is a carbon atom,
each R² is independently selected from the group consisting of hydrogen, substituted or unsubstituted alkyl groups, and substituted or unsubstituted aryl groups, and
n is a positive integer between 2 and 10; and
(b) a three dimensional structure comprising individual nanoparticles comprising atoms of said metallic or semimetallic element linked to one another via interposed oxygen atoms.

2. The ceramic-oxide network of claim 1, said metallic or semi-metallic element being silicon, and n being an integer in the range of 2-6.

3. The ceramic-oxide network of claim 2, at least a portion of said R² groups comprising non-hydroxyl functional groups, said network being cross-linked via organic polymer chains that are attached to said network via reaction with at least a portion of said non-hydroxyl functional groups.

4. The ceramic-oxide network of claim 1, comprising first particles of ceramic oxide and a plurality of said -M-L-M- structures linking adjacent ones of said first particles to form interconnected first-particle strands that are segmented by said -M-L-M- structures.

5. The ceramic-oxide network of claim 4, said first particles having an average particle size greater than 5 nm and being made up of agglomerations of relatively smaller, tightly-packed second particles of said ceramic-oxide having a particle size less than 2 nm.

6. A method of preparing a ceramic-oxide network, comprising copolymerizing a reaction mixture comprising at least one ceramic-oxide precursor species and at least one flexible-linkage precursor through one or a series of chemical reactions to produce said ceramic-oxide network, said at least one ceramic-oxide precursor species comprising a metallic or semimetallic element bound to at least one moiety through a bond that is labile under conditions of said one or a series of chemical reactions, said at least one flexible-linkage precursor having the form (R)<sub>y</sub>(R¹)<sub>x</sub>-M-L-M-(R¹)<sub>x'</sub>(R)<sub>y'</sub> wherein:
M is a metallic or semi-metallic element;
each R is attached to the associated M atom via a bond that is labile under the conditions of said reaction(s) and is individually selected to be an alkoxy or other group that will not prevent said reaction(s);
each R¹ is attached to the associated M atom via a bond that is not labile under the conditions of said reaction(s) and can be individually selected to be an alkyl group;
L comprises a chain linkage between the opposing M atoms that has the form

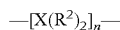

wherein X is a carbon atom;
each R² is independently selected from the group consisting of hydrogen, substituted or unsubstituted alkyl groups, and substituted or unsubstituted aryl groups; and
n is a positive integer in the range of 2-10 ;
x and y are both integers with y being not less than 1, wherein the sum x+y is equal to the valence of M minus 1; and x' and y' are both integers with y' being not less than 1, wherein the sum x'+y' is equal to the valence of M minus 1;
said ceramic-oxide network comprising a three dimensional structure comprising individual nanoparticles comprising atoms of said metallic or semimetallic element linked to one another via interposed oxygen atoms.

7. The method of claim 6, said at least one ceramic-oxide precursor species comprising an unfunctionalized ceramic-oxide precursor species, wherein all moieties attached to a metallic or semi-metallic atom thereof are attached via bonds that are labile under conditions of said reaction(s).

8. The method of claim 7, said at least one ceramic-oxide precursor species further comprising a functionalized ceramic-oxide precursor species, wherein at least one moiety comprising a non-hydroxyl functional group is attached to a metallic or semi-metallic atom thereof via an M-carbon bond.

9. The method of claim 6, said at least one ceramic-oxide precursor species comprising Si as the metallic or semi-metallic element, said flexible-linkage precursor having the form:

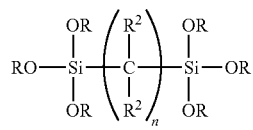

wherein each R is as described in claim 6, and each R² is individually selected to be hydrogen or a substituted or unsubstituted alkyl group.

10. The method of claim 6, said at least one flexible-linkage precursor comprising 1,6-bis(trimethoxysilyl)hexane.

11. The method of claim 6, wherein n is an integer in the range of 2-6.

12. A ceramic-oxide network prepared from co-polymerization of a ceramic-oxide precursor species and bi-silyl linking groups having the form (RO)₃—Si—R²—Si—(OR)₃, wherein:
R is an alkyl group, and
R² is selected from the group consisting of:
a) substituted and unsubstituted C₂₋₆ alkyl groups, and
b) —R³—X—R³—, wherein each R³ is independently selected to be a substituted or unsubstituted C₂₋₆ alkyl group, and X is a functional group selected from the group consisting of amines, vinyls, thiols, acrylates, and halides;
said ceramic-oxide network comprising a three dimensional structure comprising individual nanoparticles comprising atoms of said metallic or semimetallic element linked to one another via interposed oxygen atoms.

13. The ceramic-oxide network of claim 12, said bi-silyl linking groups comprising bis(trimethoxysilylpropyl)amine.

14. The ceramic-oxide network of claim 13, said network being cross-linked via polymer chains that are attached to amines of said linking groups.

15. The ceramic-oxide network of claim 14, said polymer chains comprising polyurethane chains.

16. The ceramic-oxide network of claim 14, said ceramic-oxide precursor species comprising alkyl(trialkoxy)silane.

17. The ceramic-oxide network of claim 16, said alkyl (trialkoxy)silane comprising methyl(trimethoxy)silane.

18. The ceramic-oxide network of claim 17, comprising at least 40 mol % bis(trimethyloxysilylpropyl)amine-derived Si based on total silicon in said network.

19. The ceramic-oxide network of claim 17, comprising at least 80 mol % bis(trimethyloxysilylpropyl)amine-derived Si based on total silicon in said network.

20. The ceramic-oxide network of claim 13, said ceramic-oxide precursor species comprising alkyl(trialkoxy)silane.

21. The ceramic-oxide network of claim 20, said alkyl(trialkoxy)silane comprising methyl(trimethoxy)silane.

22. The ceramic-oxide network of claim 12, said bi-silyl linking groups comprising 1,6-bis(trimethoxysilyl)hexane.

23. The ceramic-oxide network of claim 12, said ceramic-oxide precursor species comprising alkyl(trialkoxy)silane.

24. The ceramic-oxide network of claim 23, said alkyl(trialkoxy)silane comprising methyl(trimethoxy)silane.

25. A monolith comprising the ceramic-oxide network of claim 12, said monolith having a Young's modulus of at least 1 MPa and a stress at break of at least 2 MPa.

26. The monolith of claim 25, said monolith exhibiting not more than 3% unrecovered strain following a compression to 25% strain 30 minutes after release of the compression force.

27. The monolith of claim 26, having a toughness of at least 300 kJ/m$^3$.

28. The monolith of claim 26, having a porosity of at least 90%.

29. A monolith comprising the ceramic-oxide network of claim 12, said monolith exhibiting not more than 1% unrecovered strain following a compression to 25% strain 30 minutes after release of the compression force, and having a Young's modulus of at least 10 MPa and a stress at break of at least 2 MPa.

30. The monolith of claim 29, said Young's modulus being at least 100 MPa.

31. A method of making a monolith comprising the ceramic-oxide network of claim 12, the ceramic-oxide precursor species comprising an alkyl(trialkoxy)silane, the method comprising:
   a) combining said alkyl(trialkoxy)silane with said bi-silyl linking groups in an organic solvent to form a reaction mixture; and
   b) co-polymerizing said alkyl(trialkoxy)silane and said bi-silyl linking groups to form a silica wet gel.

32. The method of claim 31, wherein at least 40 mol % of the total Si in said reaction mixture are derived from the bi-silyl linking groups.

33. The method of claim 32, said organic solvent comprising acetonitrile.

34. The method of claim 32, said organic solvent comprising acetone.

35. The method of claim 32, said reaction mixture having a Si concentration of 0.75-1.65 mol/l based on total Si from both said alkyl(trialkoxy)silane and said bi-silyl linking groups.

36. The method of claim 32, said alkyl(trialkoxy)silane being methyl(trimethoxy)silane, said bi-silyl linking groups comprising bis(trimethoxysilylpropyl)amine.

37. The method of claim 36, said organic solvent being selected from the group consisting of acetone and acetonitrile, and at least 40 mol % of the total Si in said reaction mixture being derived from bis(trimethoxysilylpropyl)amine.

38. The method of claim 37, said reaction mixture having a Si concentration of 0.75-1.65 mol/l based on total Si from both said methyl(trimethoxy)silane and said bis(trimethoxysilylpropyl)amine.

39. The method of claim 37, further comprising polymer-reinforcing said wet gel followed by removal of said solvent from the reinforced wet gel to produce a reinforced silica aerogel.

40. The method of claim 37, further comprising reacting polyisocyanate with secondary amines derived from said bis(trimethoxysilylpropyl)amine in said wet gel, thereby forming a polyurethane cross-linking structure linked to said wet gel.

41. The method of claim 40, further comprising removing the solvent from said wet gel to produce a polyurethane-reinforced silica aerogel.

42. The method of claim 32, further comprising adding water to said reaction mixture to provide a water:silane ratio of 2-5 therein prior to said co-polymerization step.

43. The method of claim 42, further comprising polymer-reinforcing said wet gel followed by supercritical $CO_2$-extraction to remove said solvent from the reinforced wet gel to produce a silica aerogel.

44. A silica network prepared from co-polymerization of vinyl(trialkoxy)silane and at least one of bis[3-(trialkoxysilyl)alkyl]disulfide and bis[3-(trialkoxysilyl)alkyl]tetrasulfide linking groups.

45. The silica network of claim 44, said bis[3-(trialkoxysilyl)alkyl]disulfide linking groups being bis[3-(triethoxysilyl)propyl]disulfide.

46. The silica network of claim 45, said network being prepared by copolymerizing said vinyl(trialkoxy)silane and bis[3-(trialkoxysilyl)alkyl]disulfide linking groups with tetraalkylorthosilicate.

47. The silica network of claim 46, said tetraalkylorthosilicate comprising tetramethylorthosilicate.

48. The silica network of claim 44, prepared via co-polymerization from a solution comprising 0.1 to 0.5 mol/l tetramethylorthosilicate, 0.1 to 0.3 mol/l vinyl(trimethoxy)silane and 0.1 to 0.3 mol/l bis[3-(triethoxysilyl)propyl]disulfide.

49. The silica network of claim 48, said solution comprising 0.21-0.25 mol/l bis[3-(triethoxysilyl)propyl]disulfide.

50. A monolith comprising the silica network of claim 49, said monolith being hydrophobic and exhibiting not more than 3% unrecovered strain following two cyclic compressions to 25% strain 30 minutes after the compression force for the second compression is removed.

51. The monolith of claim 50, exhibiting a water contact angle of at least 120°.

* * * * *

UNITED STATES PATENT AND TRADEMARK OFFICE
CERTIFICATE OF CORRECTION

| | | |
|---|---|---|
| PATENT NO. | : 8,258,251 B2 | |
| APPLICATION NO. | : 12/776088 | |
| DATED | : September 4, 2012 | |
| INVENTOR(S) | : Mary Ann B. Meador, Baochau N. Nguyen and Haiquan Guo | |

It is certified that error appears in the above-identified patent and that said Letters Patent is hereby corrected as shown below:

At Col. 5, Line 26, replace "Table" with "Table 5".

At Col. 9, Line 1, delete the "." after "supercritical".

At Col. 9, Line 35, replace "re" with "are".

At Col. 12, Line 21, replace "is a positive integer" with "n is a positive integer".

Signed and Sealed this
Twenty-seventh Day of November, 2012

David J. Kappos
*Director of the United States Patent and Trademark Office*